United States Patent [19]
Yabe et al.

[11] Patent Number: 5,573,494
[45] Date of Patent: Nov. 12, 1996

[54] ENDOSCOPE COVER-SHEATHED ENDOSCOPE IN WHICH AN ENDOSCOPE-COVER COVERABLE ENDOSCOPE TO BE SHEATHED WITH AN ENDOSCOPE COVER IS STRUCTURED TO SHUT OUT WATER TIGHTLY

[75] Inventors: Hisao Yabe, Hachioji; Yoshihiro Iida, Tama; Akira Suzuki; Hideo Ito, both of Hachioji; Yoshio Tashiro, Hino; Minoru Yamazaki; Osamu Tamada, both of Hachioji; Takahiro Kishi, Yokohama, all of Japan

[73] Assignee: Olympus Optical Co., Ltd., Tokyo, Japan

[21] Appl. No.: 412,848

[22] Filed: Mar. 29, 1995

Related U.S. Application Data

[63] Continuation of Ser. No. 36,175, Mar. 23, 1993, abandoned.

[30] Foreign Application Priority Data

Feb. 23, 1993 [JP] Japan .................... 5-6274 U
Feb. 23, 1993 [JP] Japan .................... 5-6275 U
Feb. 23, 1993 [JP] Japan .................... 5-6276 U

[51] Int. Cl.⁶ .................................................. A61B 1/00
[52] U.S. Cl. ................. 600/121; 600/104; 600/106; 600/123
[58] Field of Search ......................... 128/4, 6, 844; 600/121, 122, 123, 124, 125, 104, 106, 107

[56] References Cited

U.S. PATENT DOCUMENTS

| | | | |
|---|---|---|---|
| 4,347,204 | 8/1982 | Takagi et al. | 128/4 X |
| 4,527,551 | 7/1985 | Ishii | 128/4 |
| 4,574,783 | 3/1986 | Kazuhiro et al. | 128/4 |
| 4,593,680 | 6/1986 | Kubokawa | 128/4 |
| 4,721,097 | 1/1988 | D'Amelio | 128/4 |
| 4,860,732 | 8/1989 | Hasegawa et al. | 128/6 |
| 4,867,138 | 9/1989 | Kubota et al. | 128/6 |
| 4,869,238 | 9/1989 | Opie et al. | 128/6 |
| 4,991,564 | 2/1991 | Takahashi et al. | 128/4 |
| 5,237,984 | 8/1993 | Williams, III et al. | 128/4 |

FOREIGN PATENT DOCUMENTS

| | | | |
|---|---|---|---|
| 2235786 | 2/1973 | Germany | 128/4 |

*Primary Examiner*—Richard J. Apley
*Assistant Examiner*—Beverly M. Flanagan
*Attorney, Agent, or Firm*—Armstrong, Westerman, Hattori, McLeland & Naughton

[57] ABSTRACT

In an endoscope cover-sheathed endoscope which is used for endoscopic examination with an insertional part of an endoscope sheathed with an endoscope cover, the surfaces of the insertional part, operational part, and universal cord of the endoscope are all structured to tightly shut out water. Even when contaminated, the endoscope can be immersed in chemical and thus disinfected effortlessly.

16 Claims, 51 Drawing Sheets

STENOTIC REGION

510

SECRETA

5,573,494

ENDOSCOPE COVER-SHEATHED ENDOSCOPE IN WHICH AN ENDOSCOPE-COVER COVERABLE ENDOSCOPE TO BE SHEATHED WITH AN ENDOSCOPE COVER IS STRUCTURED TO SHUT OUT WATER TIGHTLY

This application is a continuation of application Ser. No. 08/036,175 filed Mar. 23, 1993, now abandoned.

BACKGROUND OF THE INVENTION

1. Field of the Invention

The present invention relates to an endoscope cover-sheathed endoscope in which an endoscope-cover coverable endoscope to be sheathed with an endoscope cover is structured to shut out water tightly.

2. Description of the Related Art

In recent years, endoscopes have been widely adopted in medical and other fields. As for endoscopes employed in the field of medicine, when an endoscope is inserted into a living body, thorough observation may be disabled due to body fluid or the like adhering to an observation window formed in the distal part of an insertional part of the endoscope. An air supply channel and a water supply channel are provided so that fluid can be sprayed onto the observation window by manipulating the proximal portion of the endoscope in attempts to remove the body fluid or the like adhering to the observation window. In some endoscopes, a suction channel is mounted to suck and drain unnecessary body fluid or the like.

In other endoscopes, a forceps (treatment adaptor) channel is mounted so that tissues can be collected using biopsy forceps or treatment can be given using a treatment adaptor.

When an endoscope having the foregoing air supply channel, a forceps channel, or other channel is applied to a patient, cleaning or sterilization is carried out to prevent infectious diseases reliably. It takes, however, excessive time to perform cleaning or sterilization perfectly. This presents such a problem that the use efficiency of an endoscope deteriorates or the work of sterilization is a nuisance.

In efforts to solve this problem, an endoscope cover-sheathed endoscope has been proposed. In this endoscope cover-sheathed endoscope, an endoscope itself is sheathed with an endoscope cover for use so as not to get dirty even after use. The prior art includes, for example, U.S. Pat. No. 4,646,722.

In an endoscope system comprising an endoscope cover and a (endoscope cover) coverable endoscope to be sheathed with the endoscope cover, an insertional part cover having access to a patient's body cavity, and an operational part cover and other components that may be contaminated with a hand which has touched mucus adhering to the insertional part cover are all disposed of after every examination of a patient.

The endoscope-cover coverable endoscope need not be cleaned because it will not be contaminated. Efforts have been made to reduce the load an operator must incur by improving operability through downsizing and weight cutting of an operational part, or to minimize the prime cost by simplifying structures. The endoscope-cover coverable endoscope has not been structured to tightly shut out water.

In actual clinical sites, when a cover is removed from a coverable endoscope after examination, the coverable endoscope may sometimes be broken, or contaminated because it is held with a contaminated hand carelessly.

In this case, the endoscope must be disinfected to protect a doctor from being infected through the endoscope. However, since the endoscope has not been structured to shut out water, the endoscope has not been able to be immersed in disinfectant for disinfection.

An object of the present invention is to provide an endoscope cover-sheathed endoscope capable of being immersed deeply in disinfectant when contaminated because of carelessness or for other reasons, and of being handled easily.

Another object of the present invention is to provide an endoscope cover-sheathed endoscope offering high use efficiency.

The endoscope-cover coverable endoscope to be sheathed with an endoscope cover for use is structured to tightly shut out water, so that even when contaminated because of carelessness or for other reasons, the endoscope can be immersed in disinfectant and thus disinfected effortlessly.

BRIEF DESCRIPTION OF THE DRAWINGS

FIGS. 1 to 24 relate to the first embodiment of the present invention;

FIG. 1 is a general view showing a configuration of an endoscope cover-sheathed endoscope system in which the first embodiment is implemented;

FIG. 2 is a cross-sectional view showing a structure of an endoscope cover-sheathed endoscope;

FIG. 3 shows an insertional part cover and a coverable endoscope separately;

FIG. 4 is an oblique view showing a distal part of a coverable endoscope;

FIG. 5 is an oblique view showing a distal part of a cover;

FIG. 6 is an oblique view showing a coverable endoscope;

FIG. 7 is an oblique view showing an operational part of a coverable endoscope;

FIG. 8 is a cross-sectional view showing a joint between an operational part and an insertional part;

FIG. 9 is a cross-sectional view showing a joint between an operational part and a universal cord;

FIG. 10a is a cross-sectional view showing a structure for mounting a switch in an operational part;

FIG. 10b is a plan view of the switch of FIG. 10a.

FIG. 12 is a cross-sectional view showing a water leakage sensor base;

FIG. 13 is a plan view of FIG. 12;

FIG. 14 is a side view of a water leakage sensor base, showing a lock receiver and a notch;

FIG. 15 is a cross-sectional view of a high-pressure air supply connector;

FIG. 16 is a side view showing an elongated hole of the high-pressure air supply connector of FIG. 15;

FIG. 17 is a cross-sectional view showing a high-pressure air supply connector fitted into a water leakage sensor base;

FIG. 18 is a cross-sectional view of a plane containing a first lock, showing a state that a high-pressure air supply connector is fitted into a water leakage sensor base and a connection cylinder is pushed in;

FIG. 19 shows a 19—19 cross section of FIG. 17;

FIG. 20 is a development of a cam hole;

FIG. 21 is a development of a lock ditch;

FIG. 22 is a cross-sectional view showing a state that a high-pressure air supply connector is tightly fitted into a water leakage sensor base;

FIG. 23 is an explanatory diagram showing a configuration of a fluid control apparatus;

FIG. 24 is an explanatory diagram associating the operations to be actuated with the on or off states of an air supply switch and other switches;

FIGS. 25 to 33 relate to the second embodiment of the present invention;

FIG. 26 is a cross-sectional view showing a structure of an eyepiece unit of a fiberscope;

FIG. 28 is a cross-sectional view showing a diopter adjustment mechanism mounted in a fiberscope;

FIG. 30 is a cross-sectional view showing a diopter adjustment mechanism using the diopter adjustment motor shown in FIG. 29;

FIG. 31 is a block diagram showing a motor control/drive control system;

FIG. 32 is an explanatory diagram showing the sequence of operations of FIG. 31;

FIG. 33 is a block diagram showing a control system of an ultrasonic motor;

FIG. 36 is a general view showing a configuration of a covered endoscope system in which the third embodiment is implemented;

FIG. 37 is an oblique view showing a distal part of an insertional part cover;

FIG. 38 is a cross-sectional view showing a structure of a covered endoscope with an insertion aid attached;

FIG. 45 is a cross-sectional view showing a structure of the portion of a covered endoscope of the fifth embodiment in the vicinity of an operational part;

FIG. 46 is an oblique view showing the distal end of a first endoscope cover in the fifth embodiment;

FIG. 47 is an oblique view showing the distal end of a second endoscope cover in the fifth embodiment;

FIG. 48 is an oblique view showing the distal end of a coverable endoscope used in FIG. 46 or 47;

FIG. 49 is a cross-sectional view of FIG. 46;

FIG. 50 is a cross-sectional view of FIG. 47;

FIG. 51 is a cross-sectional view showing a structure of a coverable endoscope sheathed with a second endoscope cover;

FIG. 52 is a general configurational diagram of a covered endoscope system of the sixth embodiment;

FIG. 53 is a cross-sectional view showing a structure of a covered endoscope;

FIG. 54 is a side view showing an appearance of a coverable endoscope;

FIG. 55 is an oblique view showing a distal part of a coverable endoscope;

FIG. 56 is an oblique view showing a distal cover part;

FIG. 57 is a cross-sectional view of FIG. 56;

FIG. 58 is an oblique view showing a state that the gear in a coverable endoscope is engaged with the gear in a cover;

FIG. 59 is a longitudinal cross-sectional view of FIG. 56;

FIG. 60 is a block diagram showing a configuration of a motor control system;

FIG. 61 is a flowchart showing the contents of control in FIG. 60;

FIG. 63 is an oblique view showing a distal part of a cover in the seventh embodiment;

FIG. 64 is an enlarged oblique view showing part of FIG. 63;

FIG. 65 is an oblique view showing a distal part of a coverable endoscope;

FIG. 66 is an explanatory diagram showing the operation of the seventh embodiment;

DESCRIPTION OF THE PREFERRED EMBODIMENTS

Figure 1:
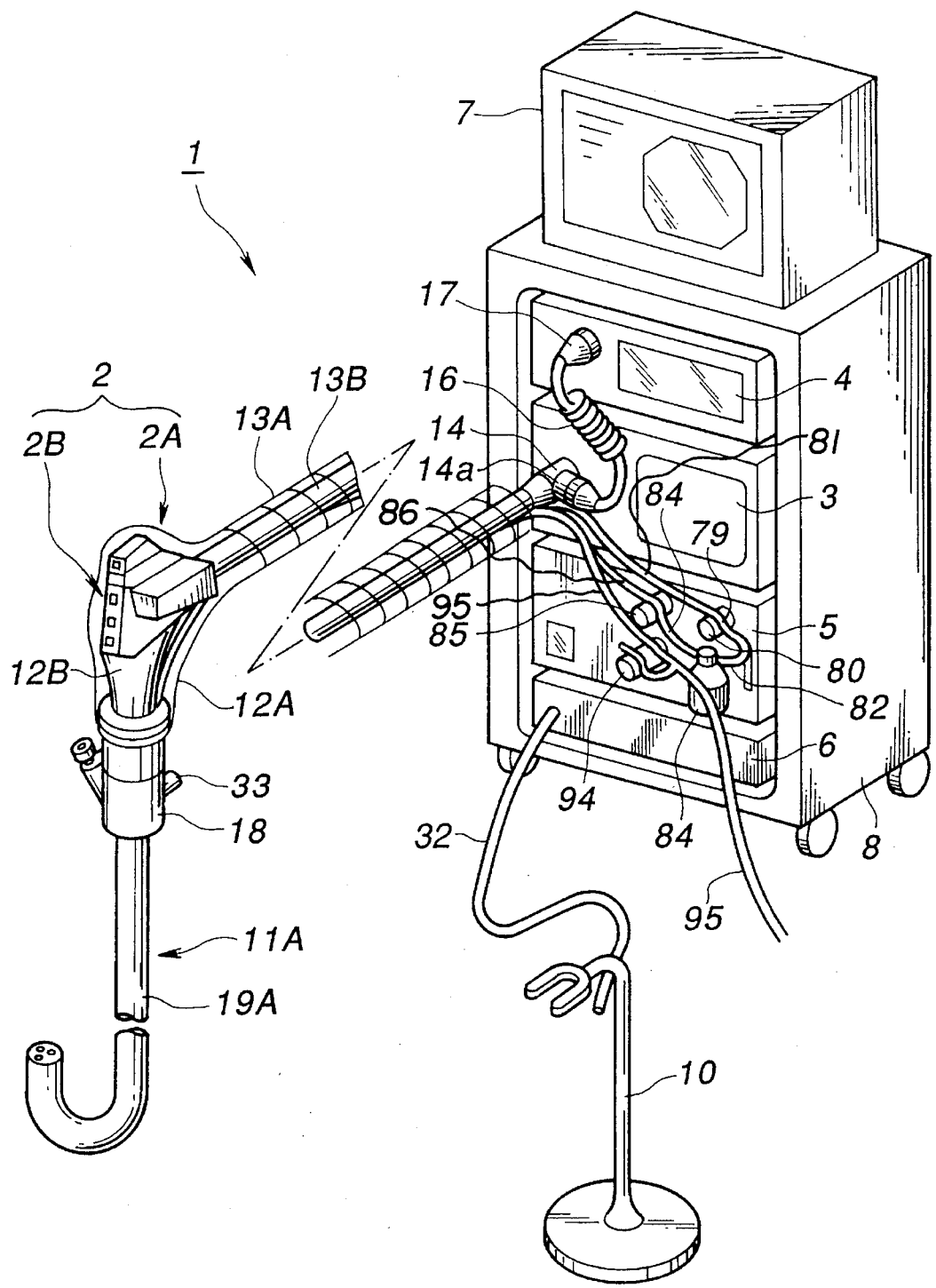

As shown in FIG. 1, ah endoscope cover-sheathed endoscope system 1 comprises a channeled endoscope cover-sheathed endoscope (hereinafter, covered endoscope) made up of a channeled endoscope cover (hereinafter, cover) 2A and a coverable endoscope 2B to be sheathed with the cover 2A, a light source apparatus 3 for supplying illumination light to the coverable endoscope 2B, a video processor 4 for processing signals acquired by an imaging means incorporated in the coverable endoscope 2B, a fluid control apparatus 5 for supplying air or water via a tube in the cover 2A, a channeled endoscope cover dilator (hereinafter, cover dilator) for use in sheathing the coverable endoscope 2B with the cover 2A, and a monitor for displaying video signals processed by the video processor 4. The light source apparatus 3, video processor 4, fluid control apparatus 5, and cover dilator 6 are stored in a cart 8. The monitor 7 is placed on the top of the cart 8.

Figure 2:
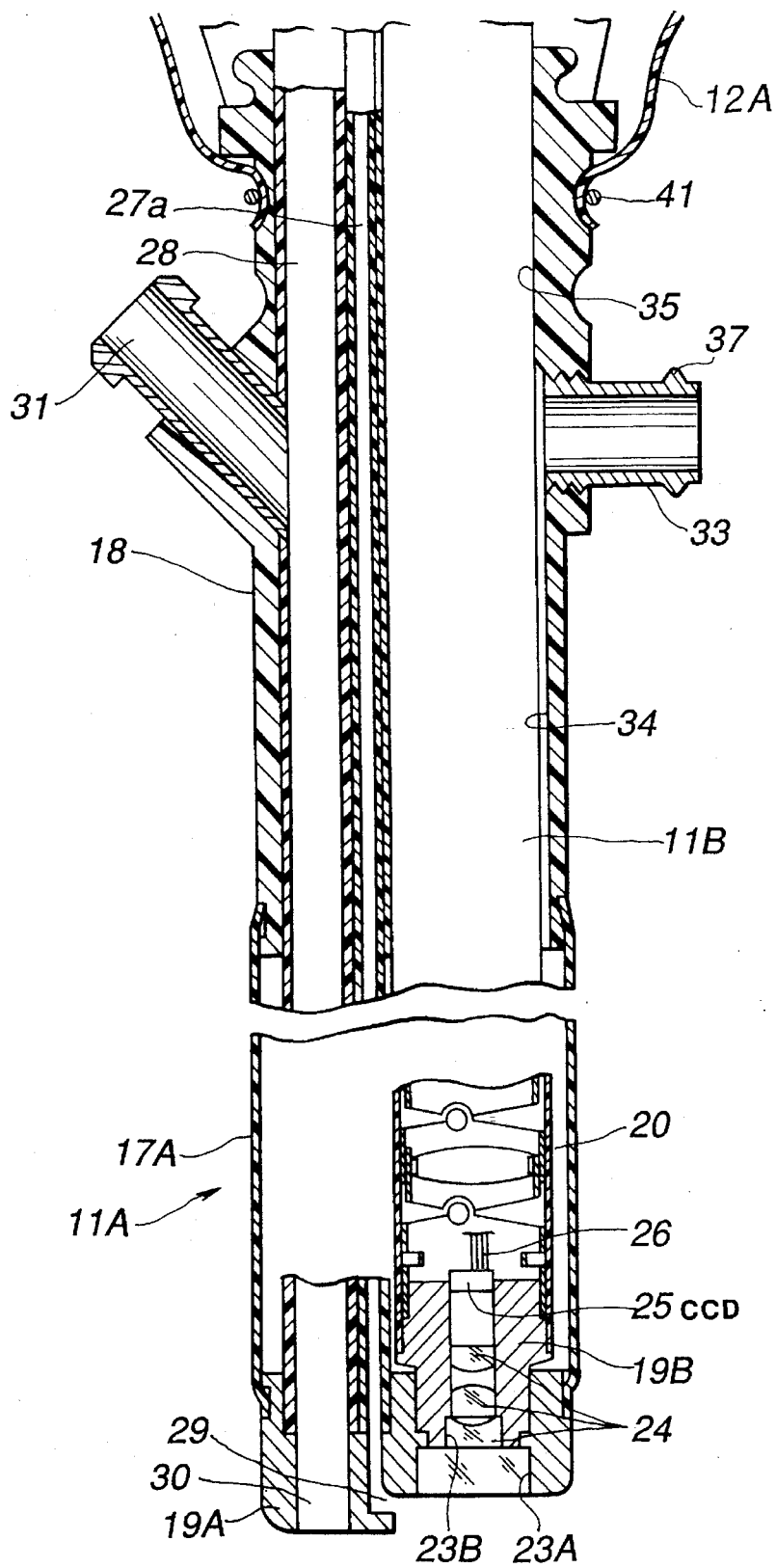

FIG. 2 is an enlarged view of the covered endoscope 2 shown in FIG. 1. When endoscopic examination is conducted, the clean coverable endoscope 2B is sheathed with the clean cover 2A. After the examination is completed, the cover 2A is disposed of, while the coverable endoscope 2B is sheathed with a new clean cover 2A and reused.

When the coverable endoscope 2B is sheathed with or unsheathed from an insertional part cover 11A that is part of the cover 2A, a cover holding instrument 10 shown in FIG. 1 is employed. For example, the proximal end of the cover 2A is hooked on the cover holding instrument 10, and then an insertional endoscope part 11B of the coverable endoscope 2B is sheathed or unsheathed.

Figure 3:
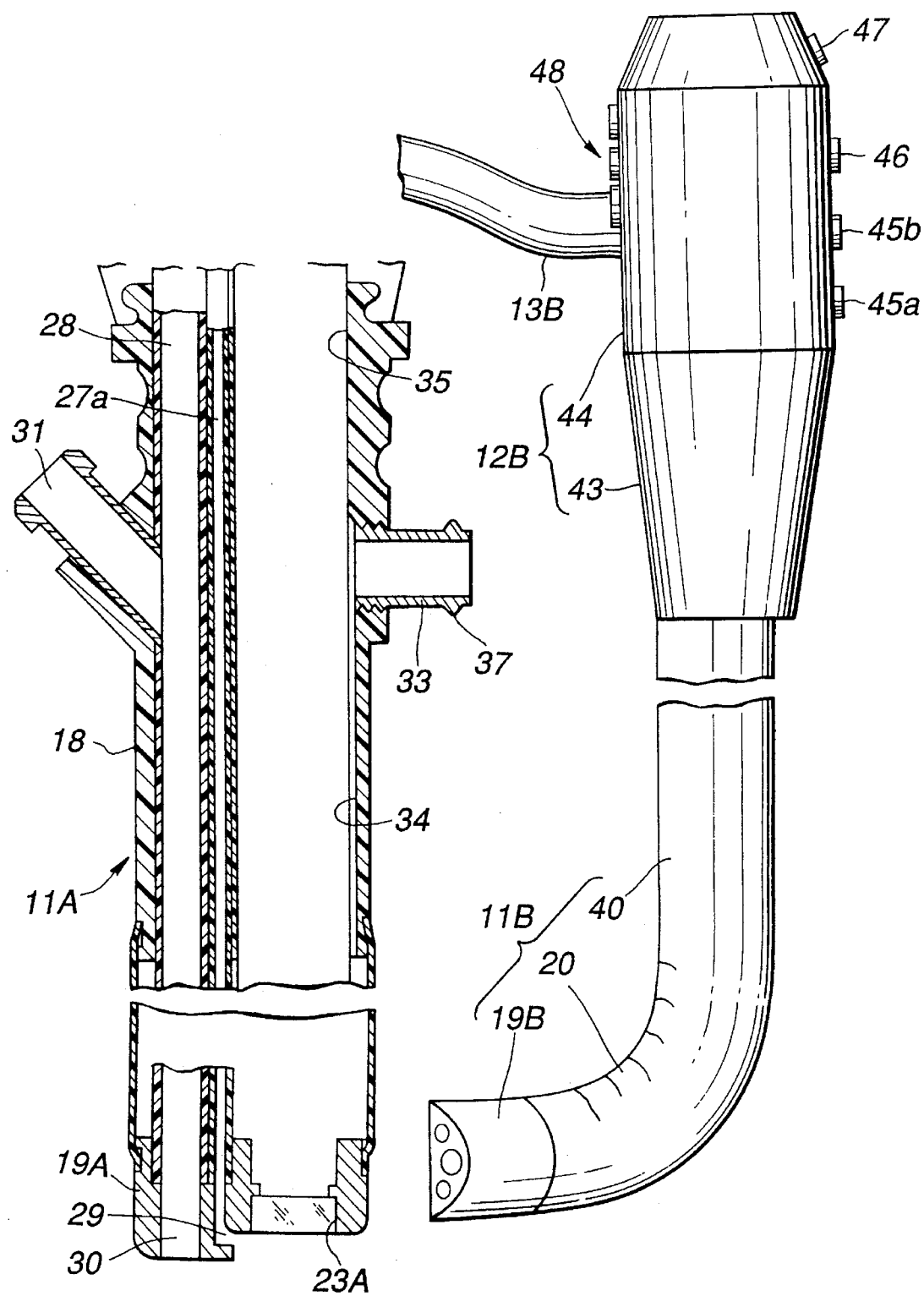

FIG. 3 shows a structure of the insertional part cover 11A separately from the coverable endoscope 2B whose insertional part 11B is inserted in the insertional part cover 11A.

Figure 6:
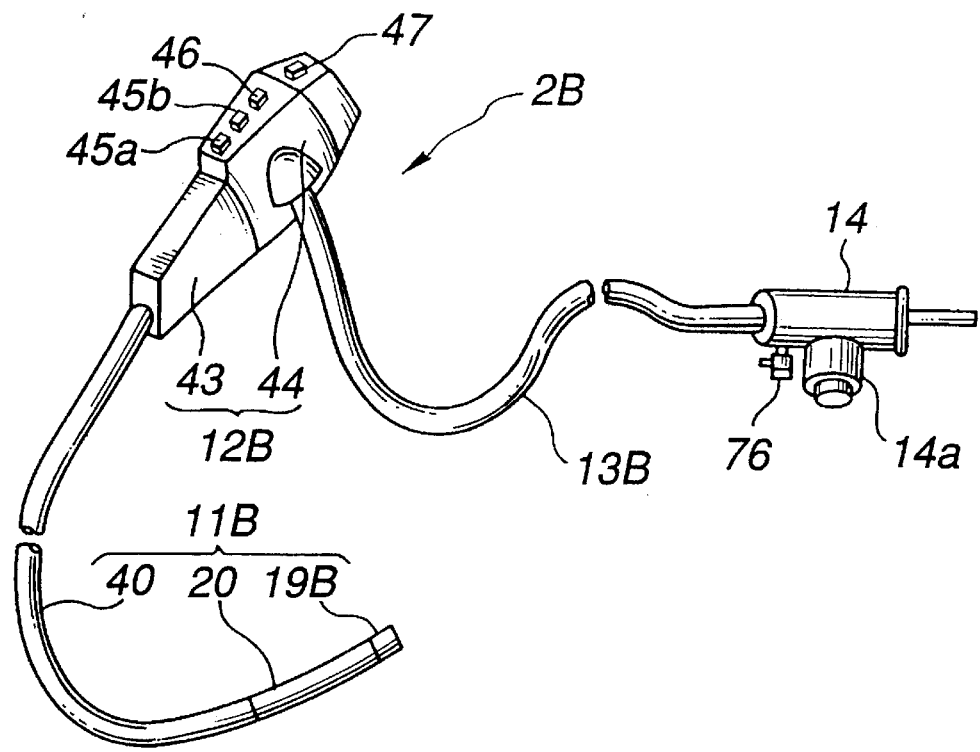

As shown in FIG. 3 or 6, the coverable endoscope 2B comprises the insertional endoscope part (hereinafter, insertional part) 11B that is elongated and flexible, an operational endoscope part (hereinafter, operational part) 12B mounted at the proximal end of the insertional part 11B, and a universal cord 13B extending from the side of the operational part 12B. A connector 14 mounted at the terminal of the universal cord 13B can be coupled with the light source apparatus 3 so as to be freely detachable.

The insertional part 11B and universal cord 13B have flexibility and are shielded with tubes made of a synthetic resin that is characteristic of tightly shutting out air and water. The operational part 12B is also shielded with an armoring member made of a synthetic resin, and capable of tightly shutting out air and water. The joint between the insertional part 11B and operational part 12B is, as described later, also structured to tightly shut out air and water.

When the connector 14 is coupled with the light source apparatus 3, illumination light originating from a lamp in the light source apparatus 3 is supplied to the terminal of a light guide.

The connector 14 has an electric contact 14a. A signal connector 17 mounted at the terminal of a signal cable 16 linked with the electric contact 14a can be plugged into the video processor 4 so as to be freely detachable.

The cover 2A comprises the insertional cover part 11A, an operational part cover 12A, and a universal cord cover 13A for shielding the insertional part 11B, operational part 12B, and universal cord 13B.

The insertional part cover 11A comprises an insertional part cover skin 17A for shielding the insertional part 11B, an operational part locking cap 18 formed at the proximal end of the insertional part cover skin 17A so as to tightly shut out air and water, and a distal cover part 19A formed at the terminal of the insertional cover skin 17A so as to tightly shut out air and water.

The insertional part cover 11A, operational part cover 12A, and universal cord cover 13A of the cover 2A are made of a thin synthetic resin; such as, polyurethane, polyester, or silicon. The operational part cover 12A may be made of a thermoplastic resin having rigidity; such as, polysulfone, polycarbonate, polyetherimide, or denatured polyphenylene oxide, so that the operational part cover 12A can be detached, operated, and gripped easily.

Figure 4:
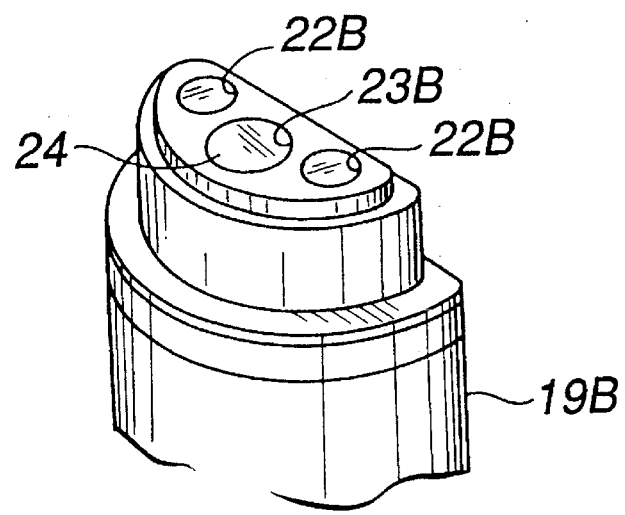

Illumination light supplied from a lamp, which is not shown, in the light source apparatus 3 into one end of a light guide travels along the light guide, and passes through illumination optical systems attached to illumination windows 22B (See FIG. 4) in a distal part 19B of the insertional part 11B and transparent plates of cover illumination windows 22A (See FIG. 5) formed to shield the illumination optical systems. The illumination light is then emitted toward a forward subject.

Light reflected from the illuminated lesion or other subject passes through the transparent plate of a cover observation window 23A formed between the cover illumination windows 22A and an objective optical system 24 (See FIG. 2) opposed to and located inside the cover observation window 23A. The light then forms an optical image on the focal plane of the objective optical system 24.

The distal cover part 19A having the cover illumination windows 22A and cover observation window 23A is coupled with the distal end of a soft operational part cover skin 17A so as to tightly shut out air and water.

A CCD 25 is arranged on a focal plane of the objective optical system 24. An optical image undergoes photoelectric transfer, passes over signal cords 26 lying through the insertional part 11B and universal cord 13B and over the signal cable 16 linked with the connector 14, and then enters the video processor 4. Signal processing is then performed to provide a standard video signal. The video signal is then input to the monitor 7 and displays an image of the subject on the display screen.

Figure 5:
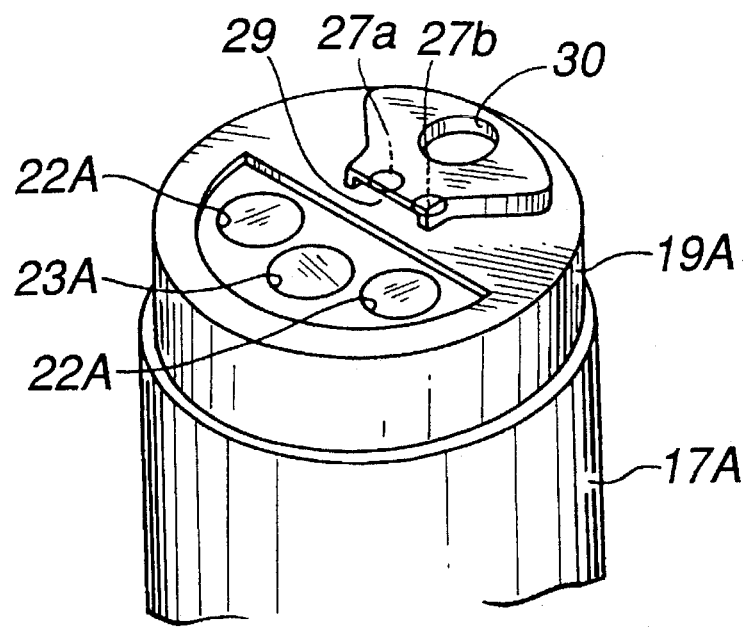

An air supply tube shown in FIG. 2, a water supply (not shown in FIG. 2), and a suction tube shown in FIG. 2 are mounted in the insertional part cover 11A, forming an air supply channel 27a, a water supply channel 27b, and a suction channel 28 respectively. As shown in FIG. 5 the distal ends of the air supply channel 27a and water supply channel 27b communicate with a nozzle 29 formed in the distal cover part 19A. The distal opening of the nozzle 29 is located on the outer surface of the cover observation window 23A.

As described above, the proximal end of the distal cover part 19A is fixed to the terminal of the insertional part cover skin 17A so as to tightly shut out air and water.

The proximal portions of the air supply tube and water supply tube are extending upstream of the operational part locking cap 18, and further extending toward the fluid control apparatus 5 while being shielded with the universal cord cover 13A together with the universal cord 13. The proximal ends of the air supply tube and water supply tube are linked with the fluid control apparatus 5. When body fluid or the like adheres to the cover observation window 23A, air or water can be supplied through the air supply channel 27a or water supply channel 27b, thus removing the body fluid or the like.

A forceps insertion port 31, and a dilation tube cap 33 with which a dilation tube 32 linked with the cover dilator 6 is coupled are formed on the side of the operational part locking cap 18. As shown in FIG. 2, the forceps insertion port 31 merges into the suction channel 28 and opens onto a forceps outlet 30, which also has a capability of a suction port, in the distal cover part 19A.

Figure 23:
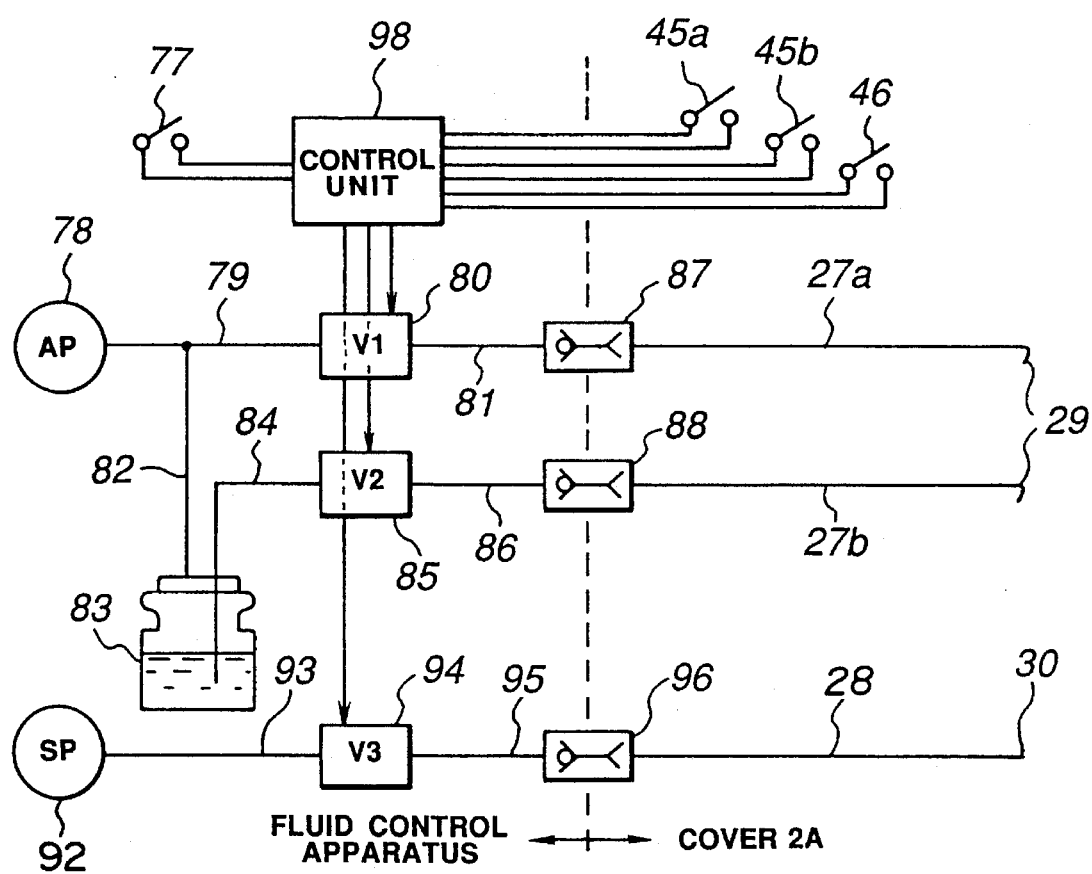

The fluid control apparatus 5 controls air supply, water supply, and suction using electromagnetic valves. As shown in FIGS. 1 and 23, an air control valve 80, a water control valve 85, and a suction control valve 94 are mounted and coupled respectively with an air pipe 81, a water pipe 86, and a suction pipe 95 which are linked with the air supply channel 27a, water supply channel 27, and suction channel 28 lying through the insertional part cover 11B. The suction control valve 94 is coupled with a suction tube 93 whose end is linked with a suction pump 92 which is shown in FIG. 23.

The water control valve 85 is coupled with a water tube 84 which is linked with a water tank 83. Two air tubes 79 and 82 are extending from the fluid control apparatus 5 and linked with the air control valve 80 and water tank 83 respectively.

As shown in FIGS. 3 and 6, the operational part 12B has a grip 43 an operator grips. An air control switch 45a, a water control switch 45b, and a suction control switch 46, and a photographic function switch 47 are arranged upstream of the grip 43. By operating these switches, air supply, water supply, suction, and photography can be carried out.

Figure 7:
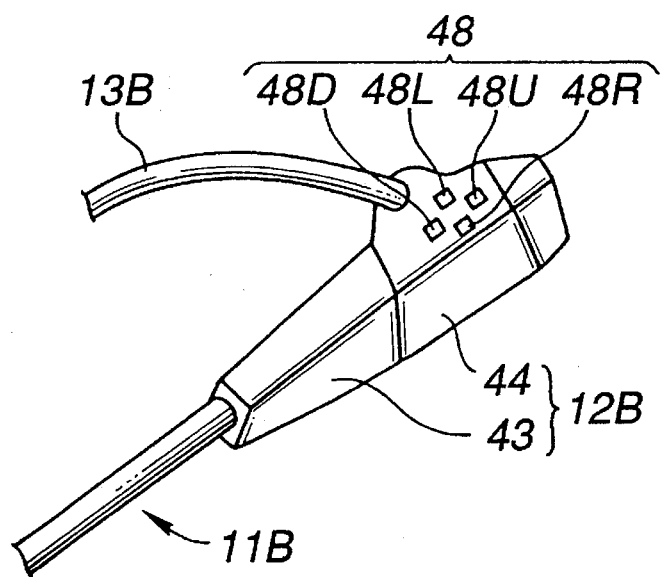

On the opposite side of the switches 45a, 45b, and 46 on the operational part 44, as shown in FIG. 7, an angulation switch 48 is present. The angulation switch 48 is made up of bending instruction switches 48U, 48D, 48R, and 48L for instructing up, down, right, and left bending. A bending section 20 formed behind the distal part 19B of the insertional part 11B can be bent by operating the angulation switch 48.

The insertional part 11B consists of the rigid distal part 19B, the bending section 20 capable of bending freely, and a flexible tube 40 having flexibility. The bending section 20 is linked with an operation wire which is not shown, and can be freely bent up, down, right, and left by pulling the operation wire using a bending drive electric motor, which is not shown, mounted in the operational part 12B. Thus, an operator can set an intended bending angle.

As shown in FIG. 2, an opening 35 of an endoscope insertion channel 34 for inserting (sheathing) the insertional part 11B of the coverable endoscope 2B is bored on the top of the operational part locking cap 18. The opening 35 communicates with the dilation tube cap 33 that opens onto the side of the operational part locking cap 18.

A projection 37 is formed on the outer circumferential surface of the dilation tube cap 33. The projection 37 prevents the attached dilation tube 32 from coming off. The endoscope insertion channel 34 occupies the portion of an internal space defined by the distal part 19A, insertional part cover skin 17A, and operational part locking cap 18 excluding the air supply channel 27a, water supply channel 27b, and suction channel 28. The coverable endoscope 2B is inserted into the endoscope insertion channel 34.

The endoscope insertion channel 34 opens onto outside at the opening 35 that is formed at the distal end thereof and through which the insertional part 11B is inserted, and at the dilation tube cap 33 with which the dilation tube 32 is coupled. Any other part of the endoscope insertion channel 34 is not exposed to outside. When inserted, the insertional part 11B is shielded with a channel formation member (for example, operational part cover skin 17A) forming the endoscope insertion channel 34 except the proximal end thereof, but not exposed to outside. The operational part 12B formed at the proximal end of the insertional part 11B is also shielded with the operational part cover 12A. As shown in FIG. 2, one of the openings of the operational part cover 12A is secured with a rubber ring 41 having elasticity below a flange of the operational part locking cap 18, so that the operational part 12B will not be contaminated.

When used for endoscopic examination, the insertional part 11B of the coverable endoscope 2B remains uncontaminated. However, since the cover 2A is contaminated, the cover 2A is available as a disposable cover that is disposed of after every use.

Figure 8:
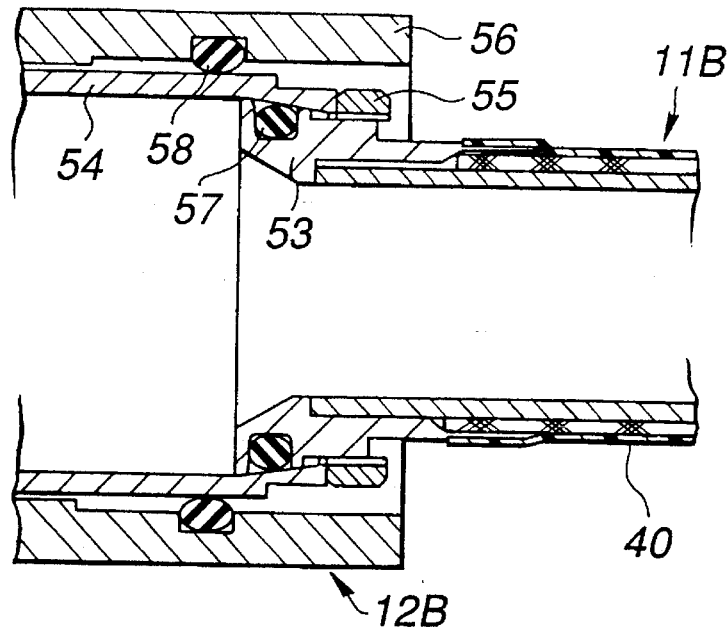

FIG. 8 shows a cross section of a joint between the operational part 12B and insertional part 11B, revealing a structure permitting tight shutout of air and water.

A base 53 fixed to the proximal end of the flexible tube 40, which is part of the insertional part 11B, so as to tightly shut out water is fixed to a frame 54 formed in the operational part 12B with setscrews 55.

O rings 57 and 58 are placed between the base 53 and frame 54, and between the frame 54 and a casing 56 of the operational part. Thus, the joint between the operational part 12B and insertional part 11B is structured to tightly shut out air and water.

The flexible tube 40 has a laminated structure in which a mesh tube and a spiral tube are laminated on a tube made of a synthetic resin.

Figure 9:
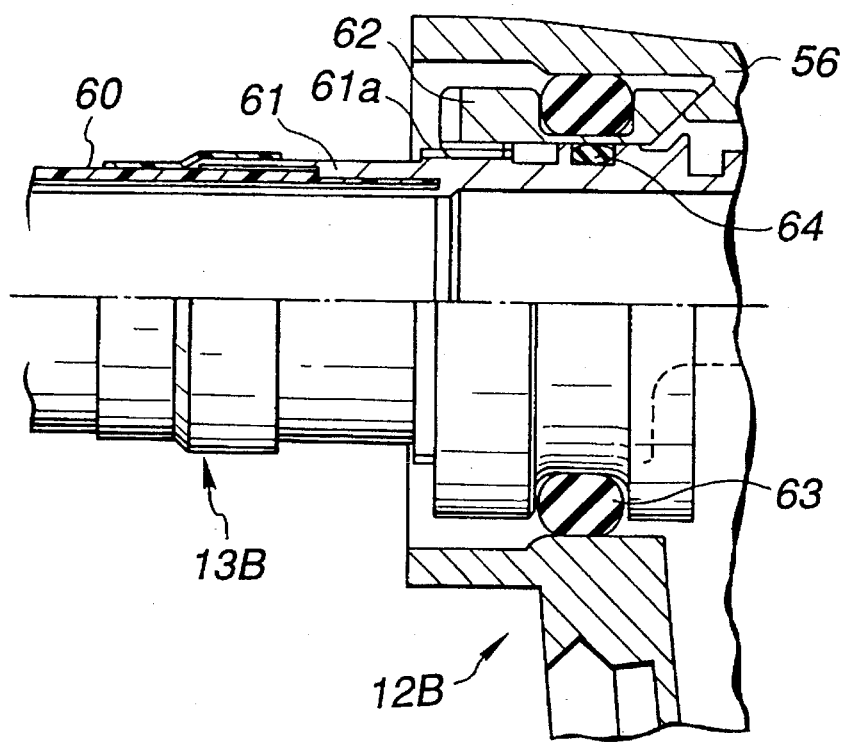

FIG. 9 shows a cross section of a joint between the operational part 12B and universal cord 13B, revealing a structure permitting tight shutout of air and water. A base 61 attached with adhesive to the proximal end of a flexible tube 60 (for example, a tube made of a flexible synthetic resin) forming the universal cord 13B is screwed to the frame (not shown) in the operational part 12B.

An O-ring receiver 62 is engaged with a thread 61a of the base 61. An O ring 63 is placed between the O-ring receiver 62 and the casing 56 of the operational part. An O ring 64 is placed between the O-ring receiver 62 and the base 61. Thus, the joint between the operational part 12B and universal cord 13B is structured to tightly shut out air and water.

Figure 10:
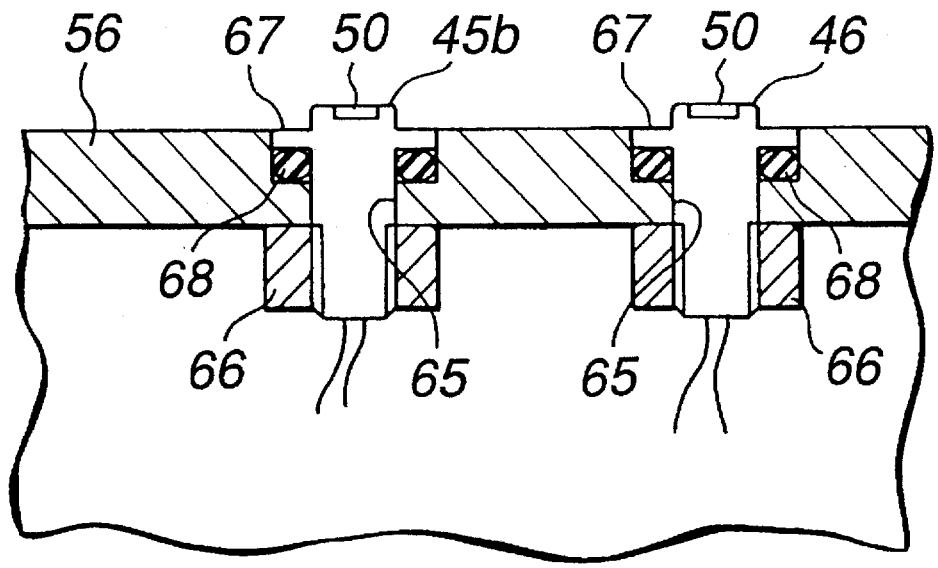
Figure 10:
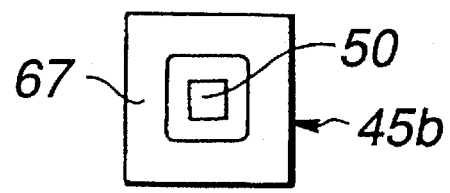

FIG. 10a shows a cross section of areas in which the control switches 45a, 45b, 46, 47, and 48 of the operational part 12B are embedded in the operational part 12B (45b and 46 alone are shown). As illustrated, each of the switches 45b and 46 is inserted into a switch embedding hole 65 bored on the casing 56 of the operational part, and secured with a setscrew 66 from inside the operational part 12B.

The switches 45a, 45b, 46, 47, and 48 have flanges 67. The casing 56 has fit holes into which the flanges 67 are fitted. An O ring 68 is attached to each of the fit holes. As a result, the areas in which the the switches 45a, 45b, 46, 47, and 48 are embedded are structured to tightly shut out air and water.

Figure 24:
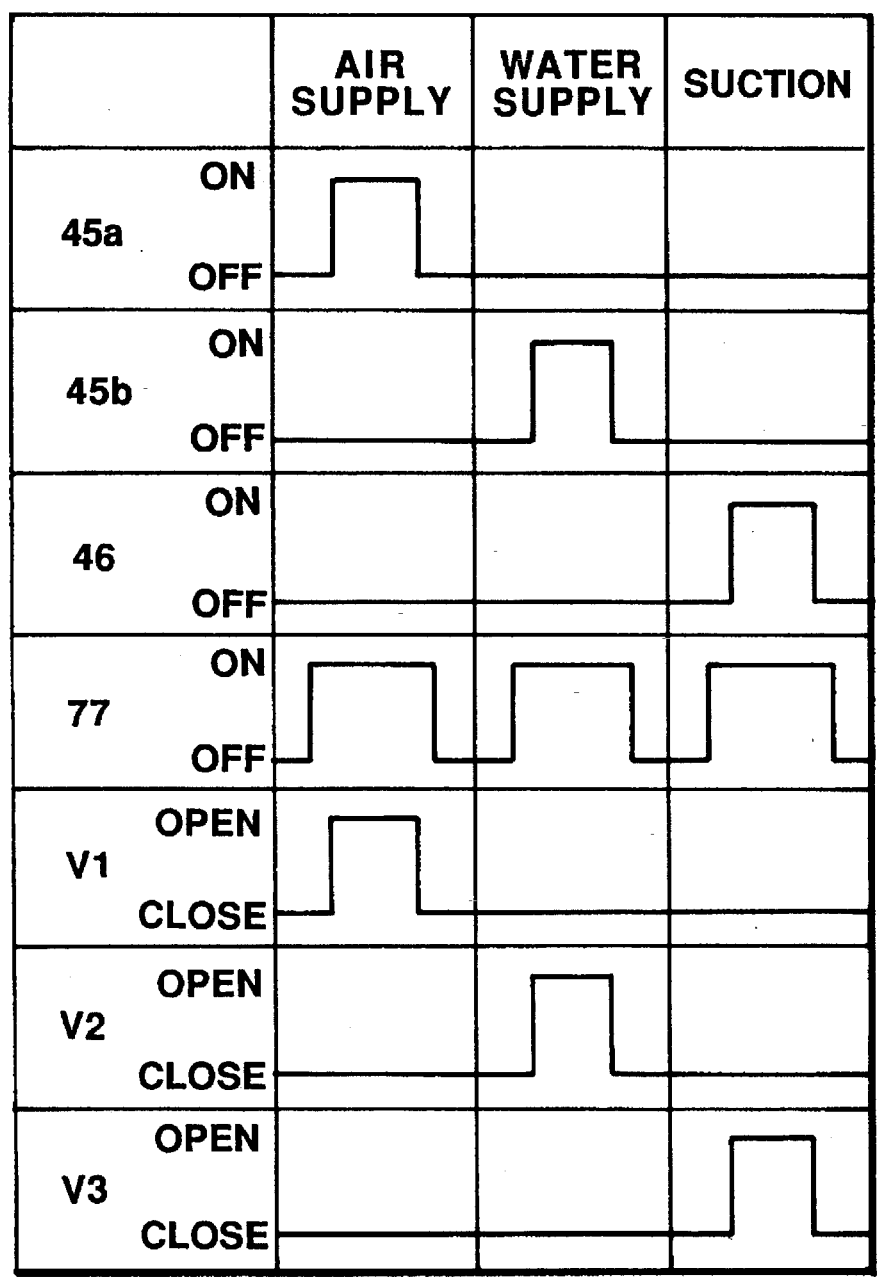

As shown in FIG. 10b, each of the switches has a light receiver 50 on the top thereof. When light is falling on the light receiver 50, the switch is off. When light is intercepted, the switch is turned on. This function will be described in more detail in conjunction with FIGS. 23, 24, and 31.

Figure 11A:
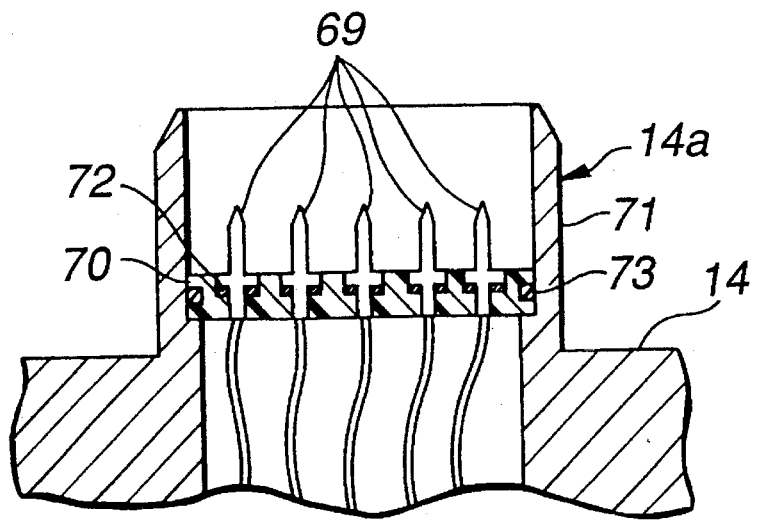
FIGS. 11a and 11b are cross-sectional views showing a structure of an electric contact.

FIG. 11a shows a cross section of the electric contact 14a formed on the side of the connector 14, revealing a structure permitting tight shutout of air and water.

The electric contact 14a has contact pins 69 for communicating image information or the like. The contact pins 69 are locked in a locking section 71 of the electric contact 14a using a contact pin receiver 70.

O rings 72 and 73 are placed between the contact pins 69 and the contact pin receiver 70, and between the contact pin receiver 70 and the locking section 71. Thus, a structure permitting tight shutout of air and water is realized.

Figure 11B:
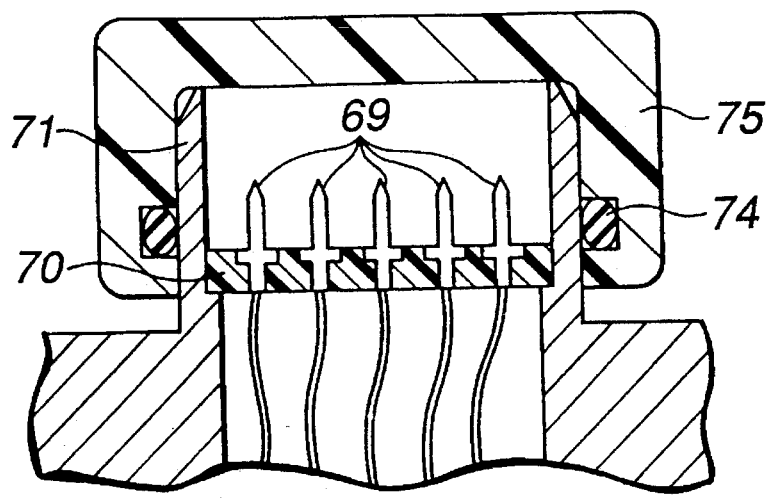

A structure shown in FIG. 11b may be adopted as the structure of the electric contact 14a for tightly shutting out water. Specifically, a cap 75 having an O ring 74 on a surface abutting on the locking section 71 is attached to the locking section 71. With this structure, for example, when the coverable endoscope 2B is to be immersed in disinfectant, the cap 75 is attached to the locking section 71 so that water will be tightly shut out of the electric contact 14a.

The light guide connector of the connector 14 to be coupled with the light source apparatus 3 is also structured to tightly shut out air and water.

As described above, not only the armors of the insertional part 11B, operational part 12B, and universal cord 13B are structured to tightly shut out air and water, but also all the joints including the joint between the insertional part 11B and operational part 12B, and the switch embedding areas are structured with seals so as to tightly shut out air and water. The coverable endoscope 2B is entirely structured to tightly shut out air and water. The coverable endoscope 2B can be entirely immersed in disinfectant to achieve perfect disinfection and sterilization.

In the above structure, a member for coating the outer surface of the coverable endoscope 2B exposed to disinfectant is made of a chemicalproof material; such as, polyurethane, polyester, polysulfone, denatured polyphenylene oxide, fluoro rubber, stainless steel, and aluminium coated with oxide film.

By the way, if a user drops the coverable endoscope 2B or hits it on an examination table, invisible minor cracks or pinholes may be created. The cracks or pinholes cause disinfectant to leak into the coverable endoscope 2B, which triggers a failure. In the coverable endoscope 2B of the first embodiment, a water leakage sensor base 76 (See FIG. 6) to be connected to a water leakage sensor which is not shown is mounted as a means for checking beforehand if water is tightly shut out.

Figure 12:
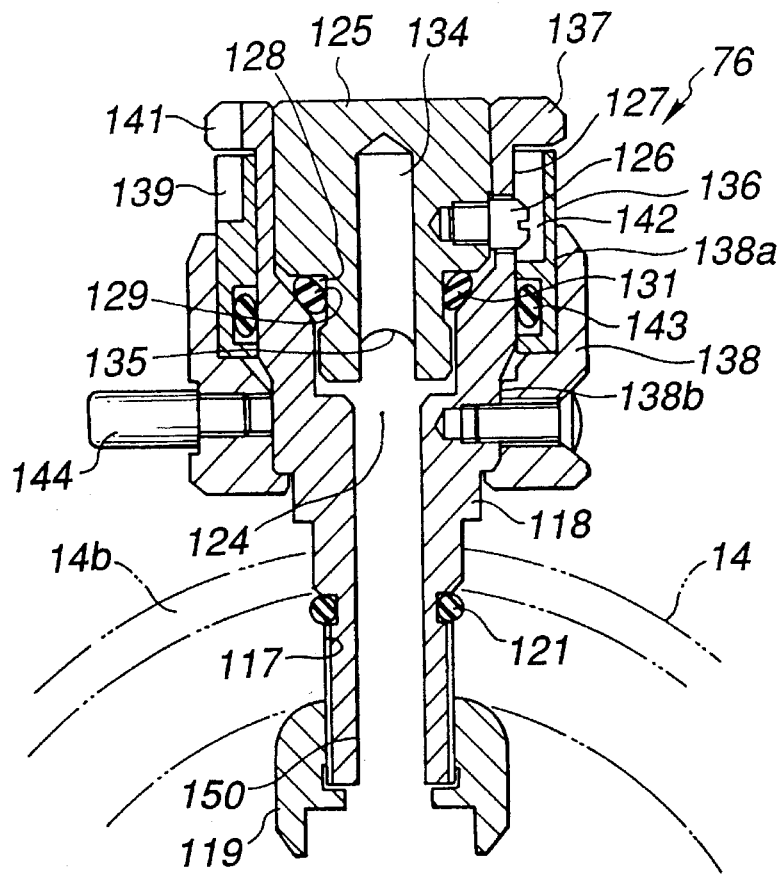

The water leakage sensor base 76 has a structure shown in FIG. 12. Specifically, the proximal portion of a communicating pipe 118 is embedded in a mounting hole 117 bored on an external wall 14b of the connector 14, and secured with a locking nut 119. An O ring 121 is interposed between the outer circumference of the proximal portion and the mounting hole 117. Thus, the proximal portion of the communicating pipe 118 is mounted airtightly.

The distal portion of the communicating pipe 118 projecting outward has larger inner and outer diameters than the proximal portion. A valve 125 is fitted into a valve chamber 124 or the inside of the communicating pipe 118 so as to be movable vertically and rotatable. A cam receiver pin 126 is screwed on the side wall of the valve 125. The cam receiver pin 126 is caged in a cam hole 127 formed on the wall of the communicating pipe 118.

Figure 20:
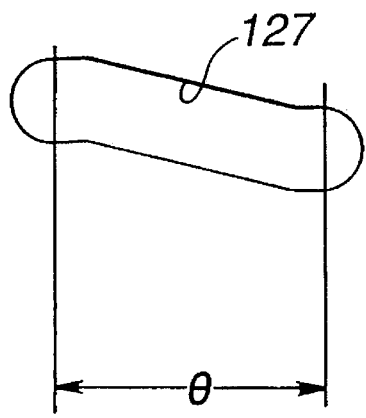

The cam hole 127 is inclined at an angular distance of θ=90° with respect to the axis of the communicating pipe 118 as shown in FIG. 20. When the cam receiver pin 126 moves along the cam hole 127, the valve 125 rotates and moves along the axis of the communicating pipe 118. An annular ring receiver ditch 128 is formed on the outer circumference of the internal end of the valve 125. An O ring 129 is embedded in the ring receiver ditch 128.

When the valve 125 lies at the lowest position as shown in FIG. 12, the O ring 129 is pressed to a seat 131 of the valve chamber 125 and blocks the communicating pipe 118.

Figure 13:
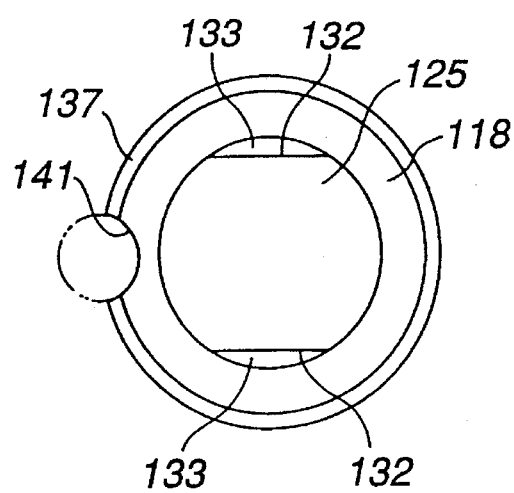
Figure 14:
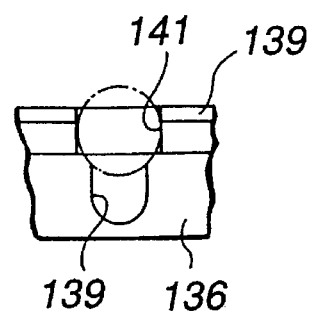
Figure 22:
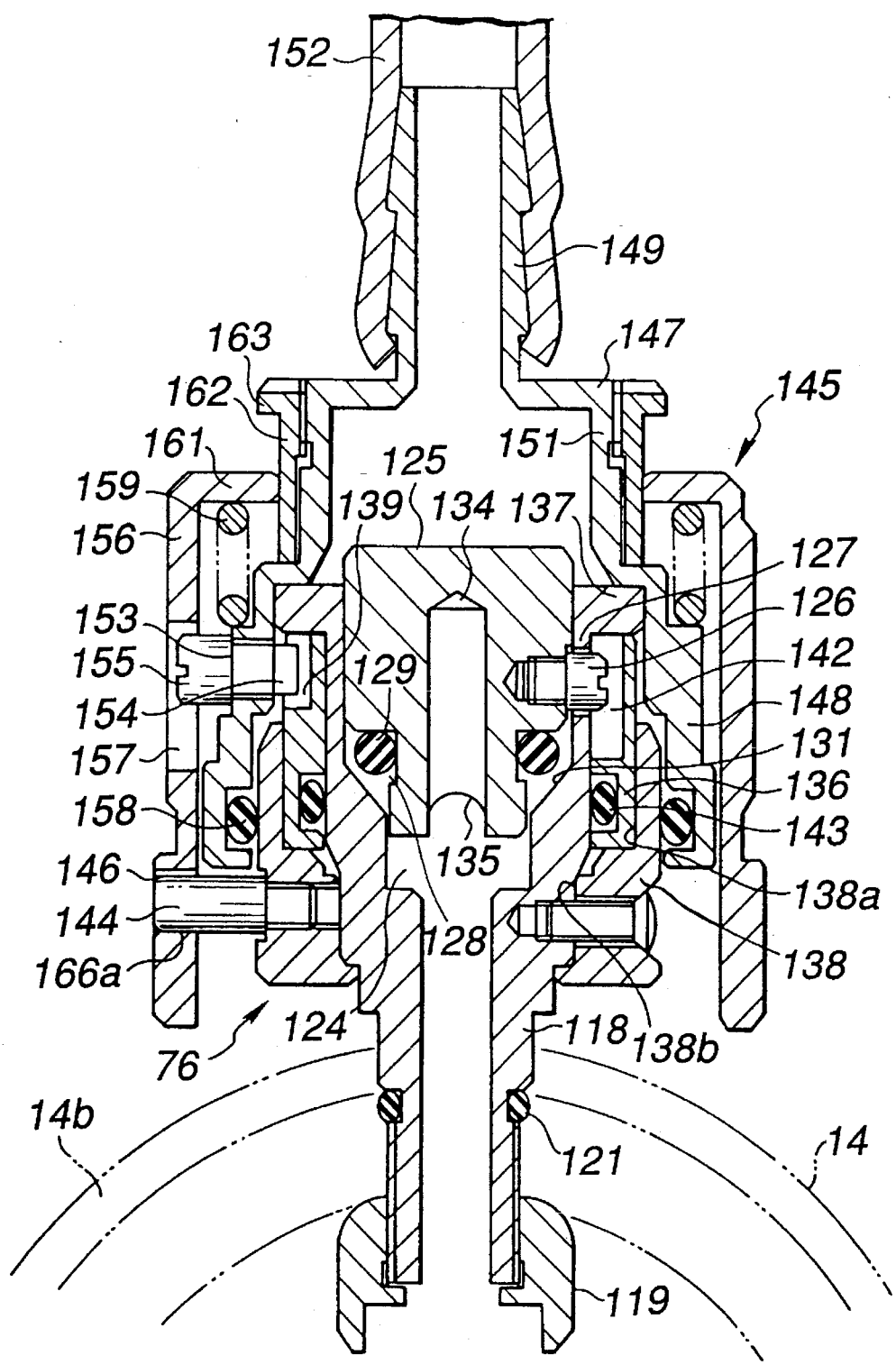

When the valve 125 rises to a position shown in FIG. 22, as described later, the O ring 129 departs from the seat 131 to canalize the communicating pipe 118. A pair of notches 132 are formed as shown in FIG. 13 on the outer circumference of the large-diameter external portion of the valve 125 beyond the O ring 129. Thus, air paths 133 are created between the notches 132 and the inner circumferential surface of the valve chamber 124.

The valve 125 has a hole 134 that opens onto the internal end. An evasion notch 135 is formed on the side wall of the hole 134 at the opening end thereof, and provides a path when the valve 125 rises to the position shown in FIG. 22. A cylindrical rotator 136 is attached to the outer circumference of the external portion of the communicating pipe 118. The rotator 136 is supported by a collar 137 formed at the external end of the communicating pipe 118 and by a cover ring 138 screwed to the communicating pipe 118. The rotator 136 does not move along the axis of the communicating pipe 118 but rotates about the communicating pipe 118 at the fixed position. The cover ring 138 covers the outer circumference of the rotator 136 except a portion thereof near the collar 137.

A recess is formed on the exposed outer circumferential surface of the rotator 136 as a lock receiver 139. The collar 137 has a notch 141 that will align with the lock receiver 139. As described later, when the valve 135 is blocked as shown in FIG. 12, the lock receiver 139 aligns with the notch 141.

The rotator 136 has an elongated hole 142 in which the cam receiver pin 126 is caged. The elongated hole 142 is elongated along the axis of the communicating pipe 118. The valve 125 and rotator 136 rotate as a united body due to the cam receiver pin 126. The valve 125 can move only in the axial direction with respect to the rotator 136. An airtight O ring 143 is interposed between the communicating pipe 118 and the rotator 136.

A pin-type first lock 144 is fixed to the cover ring 138 and projecting laterally outward. A lock ditch 146 of a high-pressure air supply connector 145, which will be described later, engages with the stopper 144.

Figure 15:
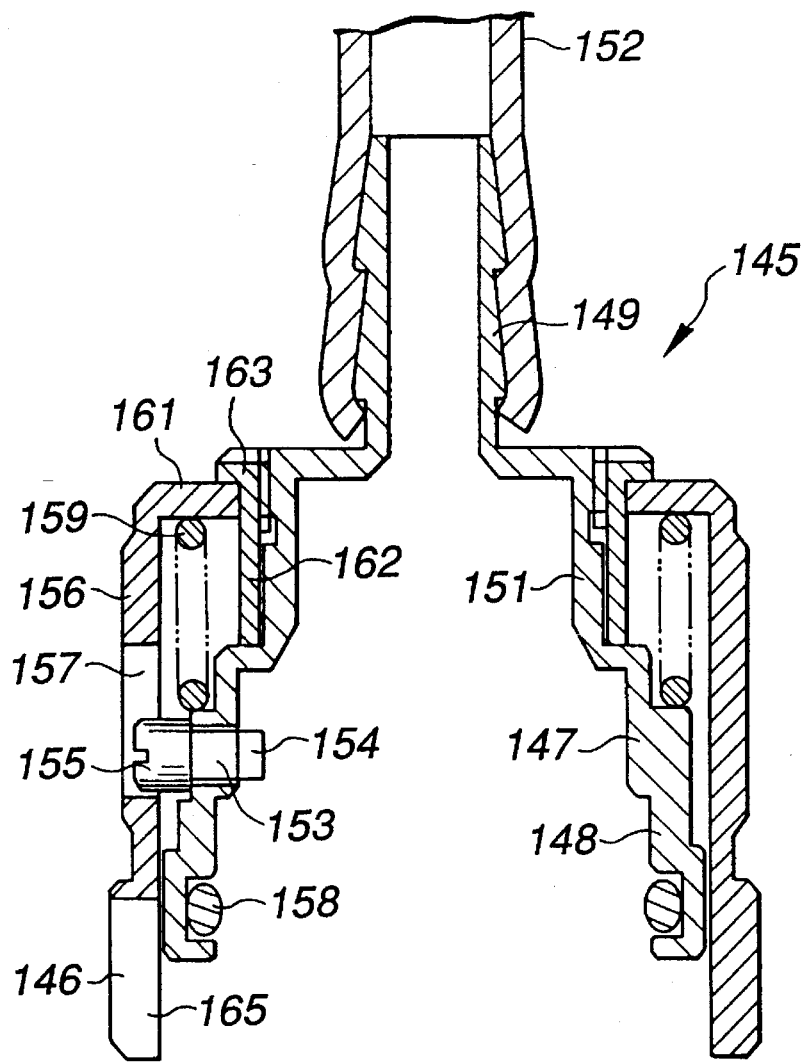

The high-pressure air supply connector 145 shown in FIG. 15 is coupled with a supply port 115 so as to be freely detachable. Specifically, a connection base 147 shown in FIG. 15 is made up of a large-diameter section 148 and small-diameter section 149, which fit the outer circumference of the supply port 115 and have a middle-diameter section 151 between them. A hose 152 communicating with a high-pressure air source, which is not shown, is fitted into the small-diameter section 149.

The large-diameter section 148 has a second lock 153 that is inserted and locked in the lock receiver 139 when the connector 145 is coupled with the supply port 115. The second lock 153 is a screw member penetrating through the wall of the large-diameter section 148. A projecting part 154 of the second lock 153 projecting inward is locked in the lock receiver 139. A head 155 of the second lock 153 projecting outside the screw member is caged in an elongated hole 157 formed on a connection cylinder 156 which will be described later. A sealing O ring 158 is attached to the inner circumference of the opening end of the large-diameter section 148, which seals the cover ring 138 of the supply port 115.

Figure 16:
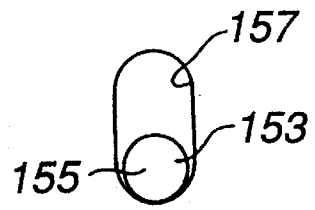

The connection cylinder 156 is attached to the outer circumference or the connection base 147 so as to be freely movable along the axis thereof. As shown in FIG. 16, when the head 155 of the second lock 153 is inserted into the elongated hole 157 formed on the connection cylinder 156, the connection cylinder 156 becomes movable within the length of the elongated hole 157 only in the axial direction thereof.

The connection cylinder 156 is pressed outward along the axis thereof by a coil spring 159 placed between the connection cylinder 156 and connection base 147. The connection cylinder 156 is aligned as shown in FIG. 15 when a spring receiver collar 161 formed at the upper end thereof abuts on a collar 163 of a presser ring 162 that is screwed to the connection base 147.

Figure 21:
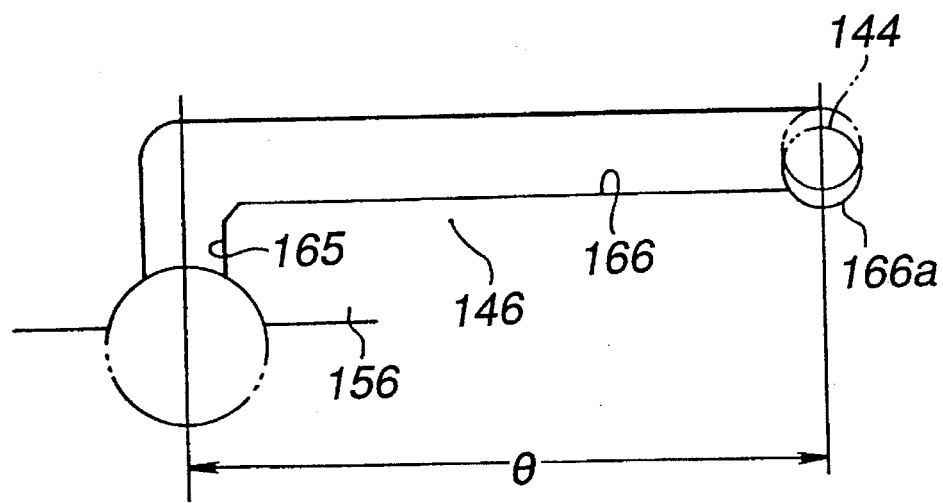

A lock ditch 146 shown in FIG. 21 is formed on the circumferential wall of the distal part of the connection cylinder 156. The lock ditch 146 is made up of a longitudinal ditch 165 and a lateral ditch 166. The longitudinal ditch 165 opens onto the distal end of the connection cylinder 165. When the connection cylinder 156 is coupled with the supply port 115, the first lock 144 is inserted into the longitudinal ditch 165. The lateral ditch 166 is elongated along the circumference of the connection cylinder 156. The rotation width Θ of the lateral ditch 166 is the same as the rotation angular distance Θ of the cam hole 127.

Next, the operation of the aforesaid system will be described. The water leakage sensor base 76 of the coverable endoscope 2B is usually positioned as shown in FIG. 12 with the cam receiver pin 126 of the valve 125 at one lower end of the cam hole 127. At this set position, the valve 125 is pushed into the valve chamber 124, and the O ring 129 is pressed forcibly to the seat 131. In short, the supply port 115 is blocked.

Figure 17:
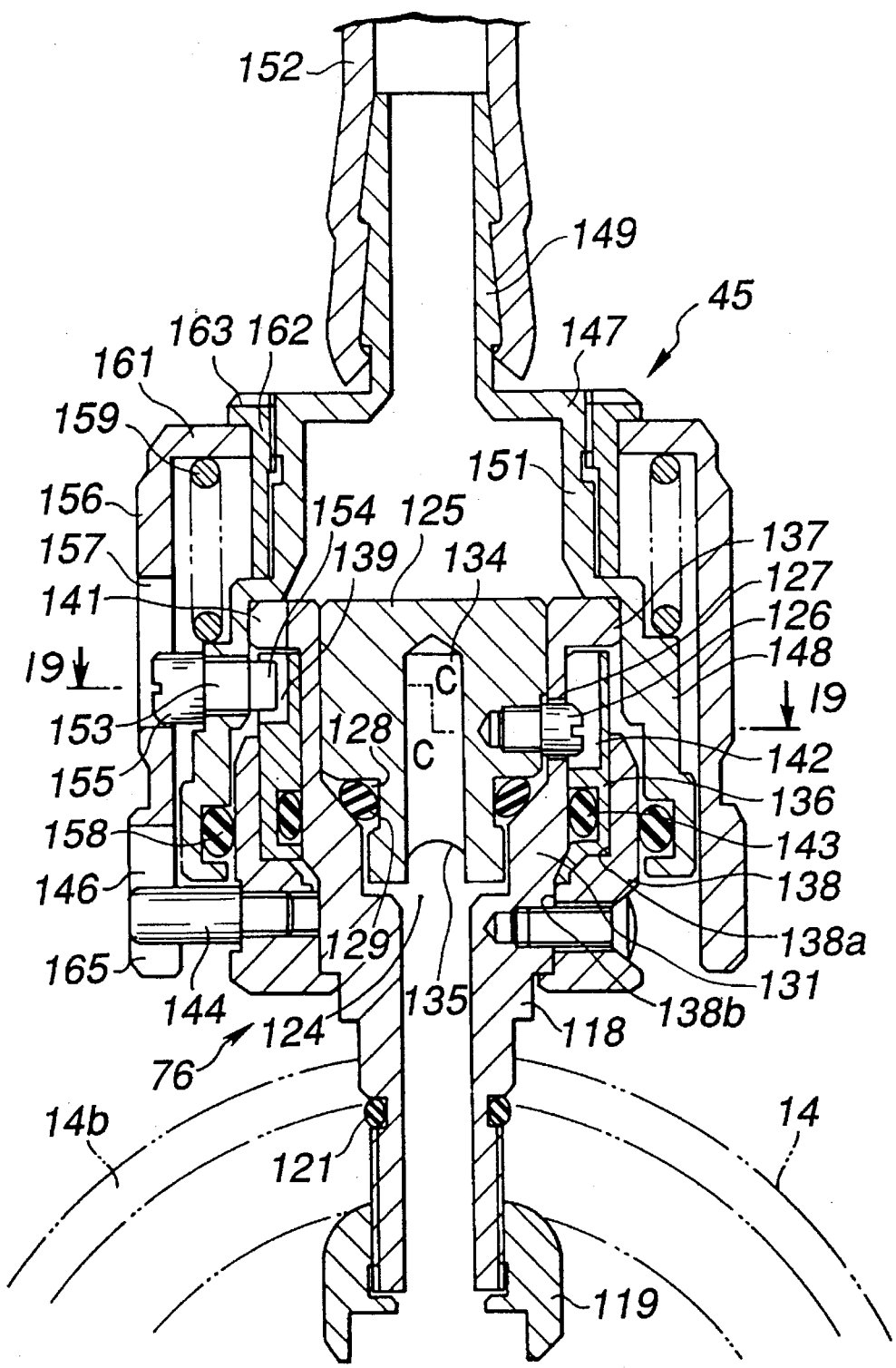
Figure 18:
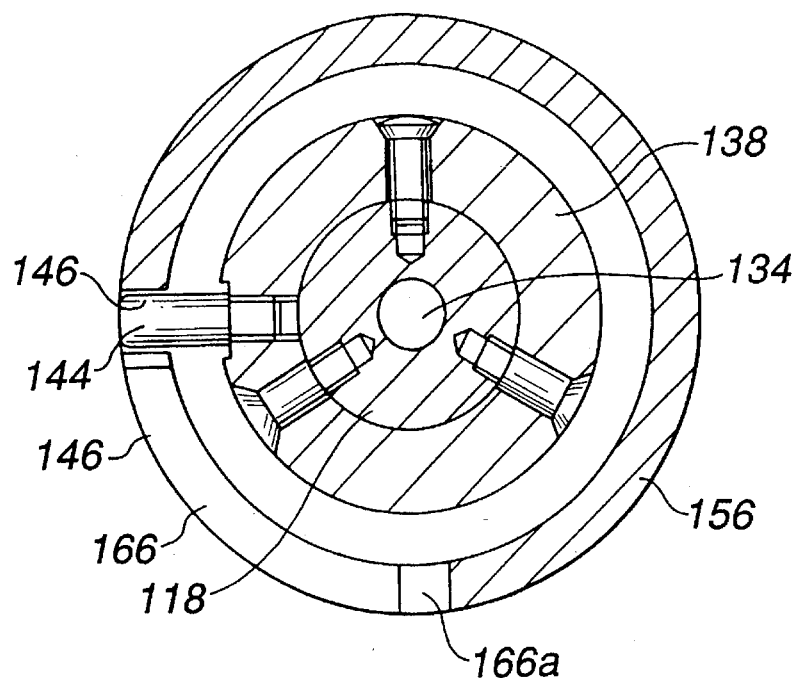
Figure 19:
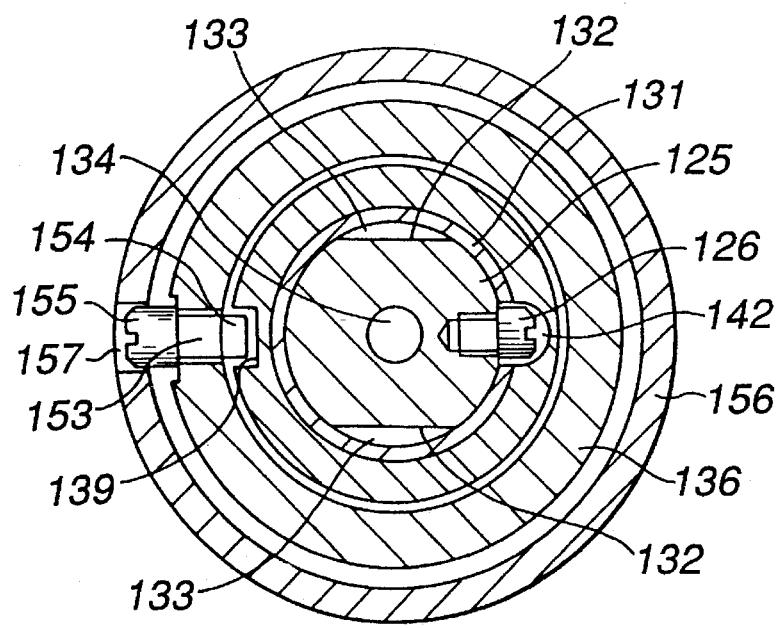

When the coverable endoscope 2B is checked for water leakage, first, the high-pressure air supply connector 145 is coupled with the supply port 115 according to the following procedure: the connection base 147 is mated with the supply port 115 so that the first lock 144 will be put in the longitudinal ditch 165 of the lock ditch 146 on the connection cylinder 156 as shown in FIG. 17.

At this time, the projecting part 154 of the second lock 153 is inserted and locked in the lock receiver 139 on the rotator 136 after trespassing on the notch 141. Then, the connection cylinder 156 is pushed down to a position shown in FIG. 22 against the restoration force of the coil spring 159, so that the first lock 144 will enter the lateral ditch 166 of the lock ditch 146. At this stage, the entire connector 145 is rotated 90° clockwise to assume the state shown in FIG. 22. That is to say, the first lock 144 comes to the deep end 166a of the lateral ditch 166, and then falls and locks into the the deep end 166a.

When the connector 145 rotates, the rotator 136 engaging with the second lock 153 rotates simultaneously due to the second lock 153. Since the cam receiver pin 126 screwed to the valve 125 is caged in the cam hole 127 of the rotator 136, the valve 125 also rotates together with the rotator 136.

Since the cam receiver pin 126 is caged in the cam hole 127, the valve 125 is raised together with the cam receiver pin 126 along the axis thereof during rotation. While the valve 125 is ascending spirally, the O ring 129 of the valve 125 departs from the seat 131. In an initial stage, the O ring 129 merely restores its original undeformed shape but does not depart from the seat 131 completely.

In a final stage, the O ring 129 departs from the seat 131 completely and is released, whereby the communicating pipe 118 is canalized through the air paths 133, the space between the O ring 129 and seat 131, and the evasion notch 135. Thus, the connection base 147 communicates with the inside of the coverable endoscope 2B.

High-pressure air is then supplied using the hose 152 and routed into the coverable endoscope 2B. The components of the coverable endoscope 2B are then pressurized. If a pinhole or a crack is present in any place of the coverable endoscope 2B, air leaking out of the pinhole or crack can be identified as bubbles in water. Consequently, the leaking place can be located. Thus, it can be checked before immersion in water if water is tightly shut out.

Even an uncovered endoscope is provided with a water leakage sensor base, which is not shown, having the same structure as the aforesaid water leakage sensor base 76.

The outer diameter and height of the rotator 136, the outer diameter and thickness of the collar 137, the outer diameter of the cover ring 138, the inner diameter and depth of a first insertion hole 138a into which the rotator 136 mounted on the cover ring 183 is inserted, the inner diameter and depth of a second insertion hole 138b into which the communicating pipe 118 is inserted, the shape and position of the lock receiver 139, the relative position in the direction of rotation between the lock receiver 139 and the lock 144, and the mounting position of the lock 144 on the cover ring 138 are identical to those of the foregoing water leakage sensor base in an uncovered endoscope.

The water leakage sensor base in an uncovered endoscope and the water leakage sensor base 76 of this embodiment are interchangeable.

The on or off operations of switches on an uncovered endoscope have been controlled with the pressing of them in the past. However, in a covered endoscope, sheathing with a cover makes it hard to press switches, or turns on switches accidentally and actuates them incorrectly. This has long been found as a great drawback. Moreover, the operational part cover must be designed exclusively to enable the pressing of switches.

This embodiment provides a switching mechanism permitting reliable switching operations, preventing incorrect actuation of switches, and offering excellent operability.

The control switches 45a, 45b, 46, 47, and 48 on the coverable endoscope 2B are realized with switches that need not be pressed but can be turned on or off, so that all switching operations including those for air supply, water supply, suction, and bending can be performed reliably. The switching operations for air supply, water supply, and suction will be described as an example in conjunction with FIGS. 23 and 24.

Each control switch has the light receiver 50 shown in FIG. 9 on the top thereof. While light is falling on the light receiver 50, the switch is off. When the light receiver 50 is hidden with a finger and light is intercepted, the switch is turned on.

As shown in FIG. 23, the fluid control apparatus 5 has a main switch 77 for controlling air supply, water supply, and suction. Only when the switch 77 is on, the switches 45a, 45b, and 46 function. When the air supply, water supply, and suction functions are unnecessary, the switch 77 should be turned off so that even if light is accidentally intercepted from the light receiver 50 of the switch 45a, 45b, or 46, air supply, water supply, or suction will not be carried out.

The first air tube 79 is coupled with an air pump 78 in FIG. 23. The first air tube 79 is linked with the second air pipe 81 via the first electromagnetic valve 80. The first water tube 82 branches out from the middle of the first air tube 79, and communicates with the water tank 83. The first water tube 82 is further linked with the second water pipe 84 via the water tank 83.

The second water pipe 84 is linked with the second water pipe 86 via the second electromagnetic valve 85. The second air pipe 81 and second water pipe 86 are provided with quick-disconnect couplings 87 and 88. The quick-disconnect couplings 87 and 88 enable one-touch connection of the second air pipe 81 and second water pipe 86 to the air supply channel 27a and water supply channel 27b mounted in the cover 2A. The terminals of the air supply channel 27a and water supply channel 27b join at the nozzle 29. The air supply channel 27a and water supply channel 27b may join in their terminals to form an air/water supply channel, and the terminal of the air/water supply channel may be provided with a nozzle.

The suction pump 92 is coupled with the first suction tube 93. The first suction tube 93 is linked with the second suction pipe 95 via the electromagnetic valve 94. The second suction pipe 95 is provided with a quick-disconnect coupler 96. The quick-disconnect coupler 96 enables one-touch connection to the suction channel 28 mounted in the cover 2A.

The first electromagnetic valve 80, second electromagnetic valve 85, and third electromagnetic valve 94 are electrically coupled with a control unit 98. The control unit 98 is connected to the switches 45a, 45b, and 46 formed on the operational part 44 of the coverable endoscope 2B and to the main switch 77 formed on the fluid control apparatus 5.

Normally, air supply, water supply, and suction are carried out by turning on or off the main switch 77 formed on the fluid control unit 5 and the switches 45a, 45b, and 46 formed on the operational part 44. When air is to be supplied with the main switch on, the light receiver 50 of the switch 45a is hidden with a finger to intercept light. The switch 45a is then turned on. Consequently, the control unit 98 opens the electromagnetic valve 80 to supply air. Similarly, when the switch 45b is turned on, water is supplied. When the switch 46 is turned on, suction is carried out.

As described above, since the control switches are realized with switches that need not be pressed but can be turned on or off, even when the operational part cover 12A is attached, the switches can be turned on or off reliably. Consequently, such functions as air supply, water supply, and suction can be executed.

If a switch 48 capable of being turned on or off without a touch is employed, bending can also be performed reliably. At least the portion of the operational part cover 12A coinciding with the control switches is made of a material that is so transparent that even when the operational part is covered, the control switches will not be turned on.

According to the first embodiment, the entire surface of the coverable endoscope 2B including the insertional part 11B is structured to tightly shut out water (which, however, is realized by capping the electric contact 14a in FIG. 11). Therefore, after endoscopic examination is completed, when the coverable endoscope 2B is removed from the contaminated cover 2A, even if the coverable endoscope 2B is contaminated, the coverable endoscope 2B can be immersed in chemical solution and thus disinfected easily.

The coverable endoscope 2B, which is not channeled, can be immersed in chemical solution and thus disinfected for a short period of time. Thus, an endoscope system offering excellent use efficiency can be materialized.

In the aforesaid first embodiment, the coverable endoscope 2B is an electronic endoscope. The first embodiment can apply in substantially the same manner to an optical coverable endoscope (that is, a coverable fiberscope) in which an image guide is used instead of an imaging device and an eyepiece is employed for observation.

Figure 25A:
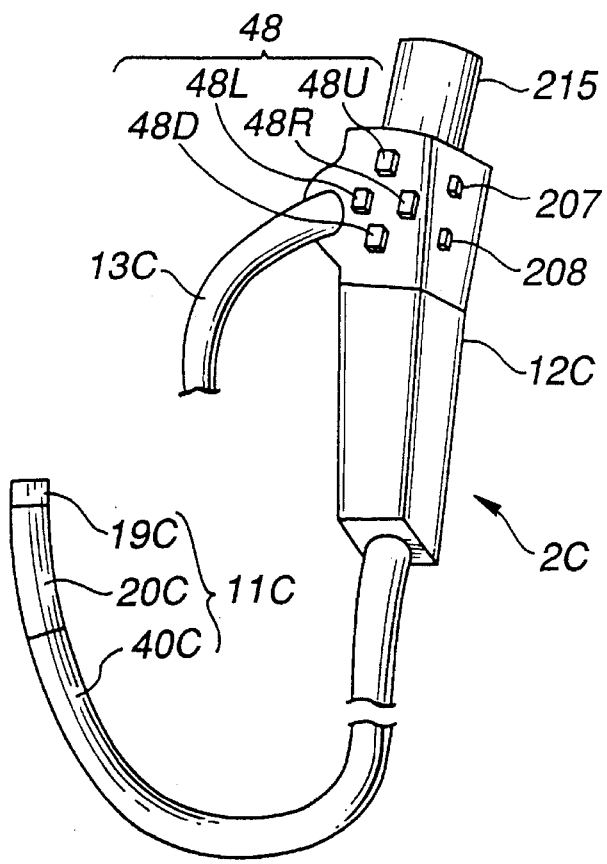
FIGS. 25a and 25b are oblique views showing a fiberscope.
Figure 25B:
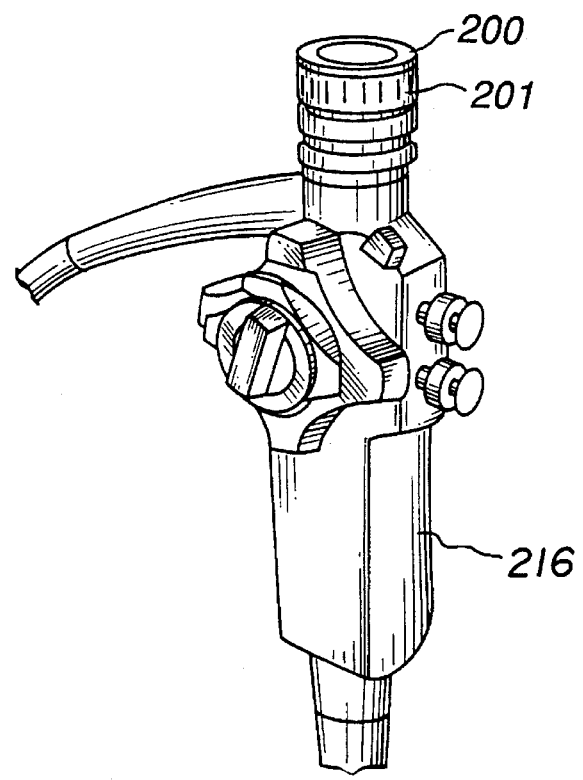

In a fiberscope type covered endoscope using a fiberscope, the image forming position of an eyepiece must be varied to adjust the diopter depending on an operator's eyesight. In a conventional uncovered endoscope 216, when the image forming position is to be varied, the position of the eyepiece in the direction of the optical axis thereof must be moved by adjusting an adjustment ring 201, which is shown in FIG. 25b, mounted on the outer circumference of an eyepiece frame 200 and interlocked with the eyepiece.

In a covered endoscope, however, the presence of the cover 2A makes it impossible or hard to move an adjustment ring. A covered endoscope 2C of the second embodiment has a configuration shown in FIGS. 25a and 26 so that the image forming position of an eyepiece can be varied freely despite the presence of the cover 2A.

The covered endoscope 2C comprises an insertional part 11C made up of a distal part 19C, a bending section 20C, and a flexible section 40C, an operational part 12C formed at the proximal end of the insertional part 11C, an eyepiece unit 215 formed on the top of the operational part 12C, and a light guide cord 13C extending from the side of the operational part 12C.

Figure 26:
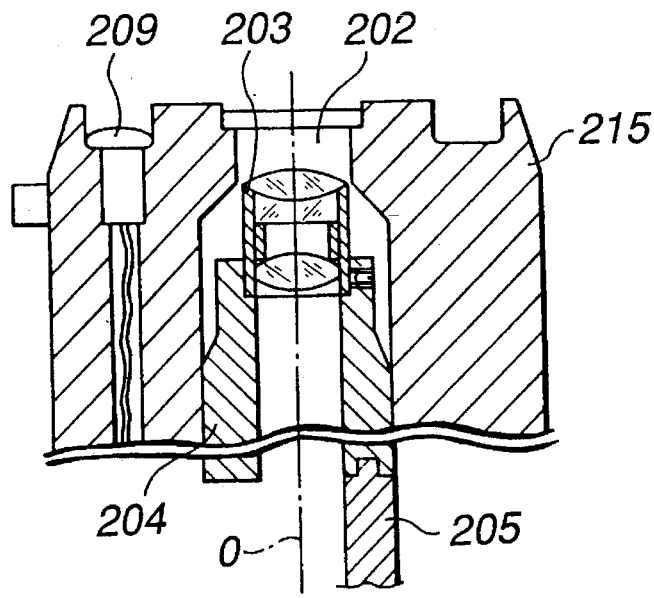

As shown in FIG. 26, an eyepiece 202 mounted in the eyepiece unit 215 is locked in an eyepiece frame 203 with adhesive. The eyepiece frame Is fixed to an adjustment base 204.

The adjustment base 204 is coupled with a connecting rod 205. The connecting rod 205 is linked with an ultrasonic motor, which is not shown, in an operation unit 206. The ultrasonic motor is of the type that when energized, triggers an axial movement. As shown in FIG. 25a, when a diopter adjustment switch 207 or 208 formed on the external wall of the operational part 12C is pressed to energize the ultrasonic motor, the ultrasonic motor provides an axial output. Consequently, the eyepiece frame 203 connected to the ultrasonic motor via the connecting rod 205 and adjustment base 204 moves along the optical axis O thereof. Thus, the image forming position of the eyepiece 202 can be varied.

When the switch 208 is turned on, the eyepiece 202 moves up above the middle position. When the switch 209 is turned on, the eyepiece 202 moves down below the middle position.

When an endoscopic camera (not shown) is connected, a contact in the camera and a contact 209 in the eyepiece frame communicate with each other. A signal indicating that a camera has been mounted is then sent to a light source apparatus (not shown). According to the signal, the image forming position of the eyepiece 205 is varied so as to align the eyepiece 202 with the film in the endoscopic camera.

With the aforesaid arrangement, the image forming position of the eyepiece 202 can be varied freely despite the presence of a cover 2A, and the diopter can be adjusted. The control sequence of the ultrasonic motor will be described later.

In FIG. 25a, the lower portion of the operational part 12C is joined with the insertional part 11C, and the light guide cord 13C is extending from the side of the operational part 12C.

A method for providing a driving force for moving the eyepiece frame 203 along the optical axis of the eyepiece is not limited to the aforesaid arrangement using an ultrasonic motor. Another method will be described.

Figure 27A:
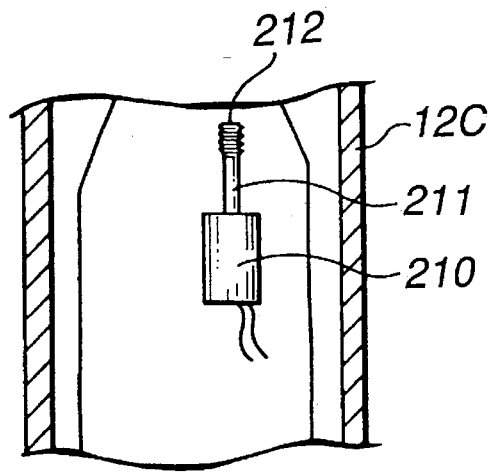
FIGS. 27a and 27b show a diopter adjustment motor mounted in an operational part of a fiberscope.

A screw 212 is attached to, as shown in FIG. 27a, a transmission axis 211 one of whose ends is fixed to an electric motor 210 mounted in the operational part 12C.

Figure 27B:
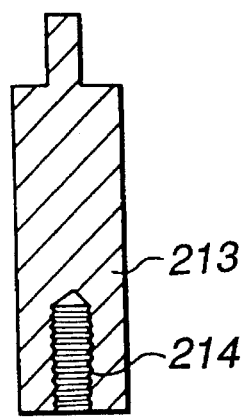
Figure 28:
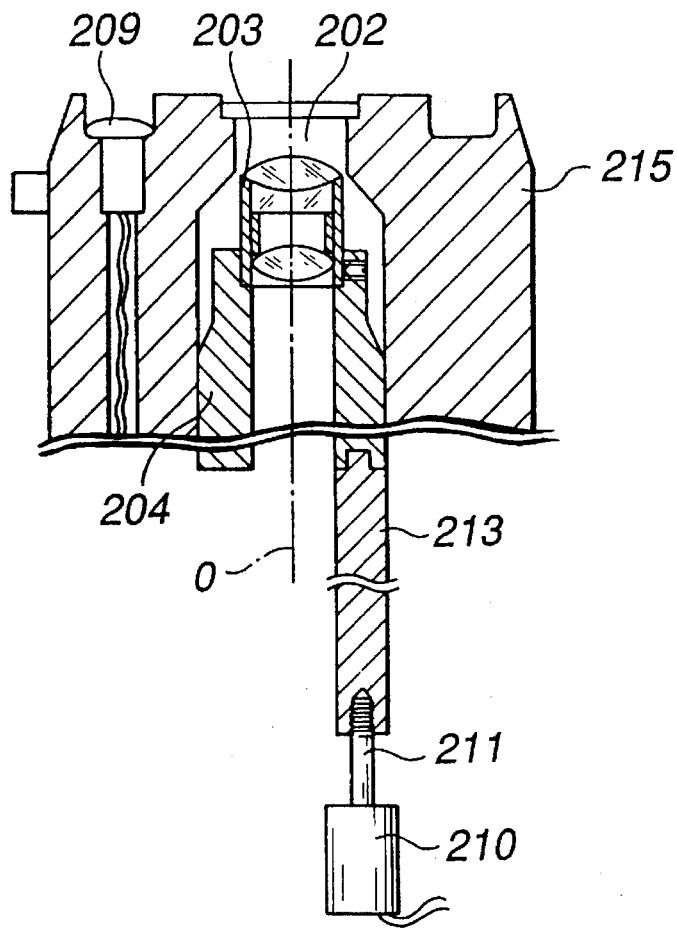

A connecting rod 213 has, as shown in FIG. 27b, a screw 214 that engages with the screw 212 attached to the transmission axis 211. The transmission axis 211 is, as shown in FIG. 28, engaged with the screw 214.

When the electric motor is energized using the diopter adjustment switch 207 or 208 to rotate the electric motor, the connecting rod 213 moves in the axial direction along the screw ditches of screws 212 and 214. As a result, the eyepiece frame 203 connected via the adjustment base 204 moves along the optical axis O in FIG. 28.

Figure 29A:
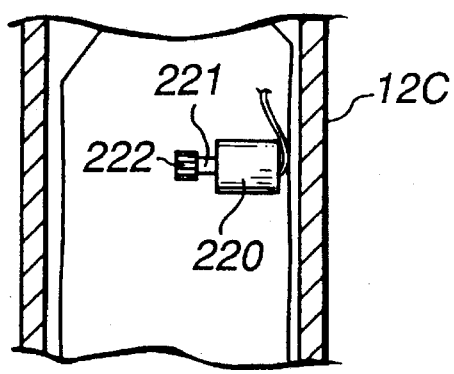
FIGS. 29a and 29b show a diopter adjustment motor different from that shown in FIG. 27.
Figure 29B:
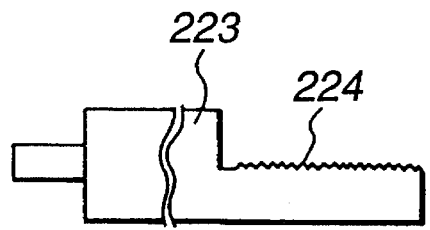

Another method will be described below. A gear 222 is fixed to the other end of a transmission axis 221 whose one end is fixed to an electric motor 220 mounted in the operational part 12C. In FIG. 29b, a rack 224 that engages with the gear 222 is formed on part of a connecting rod 223.

Figure 30:
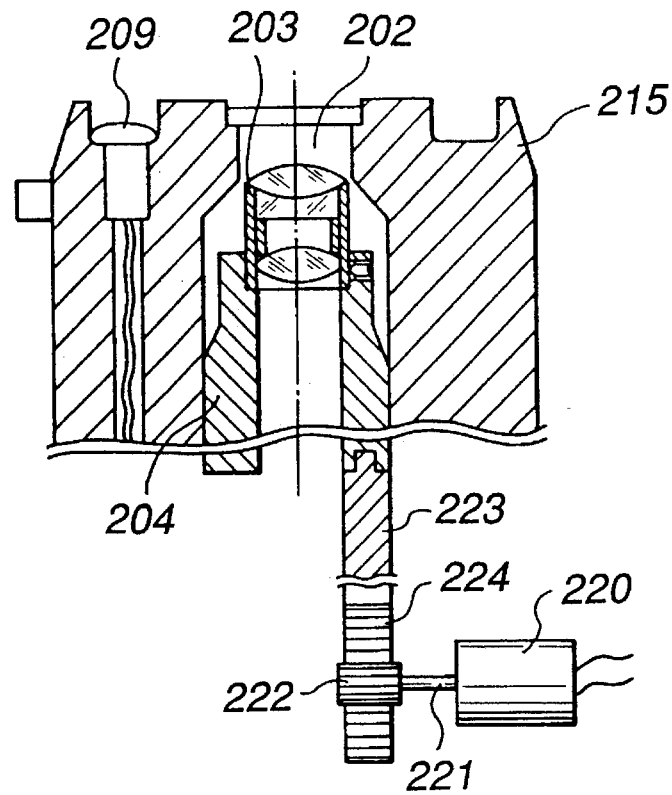

In FIG. 30, the gear 222 is engaged with the rack 224 formed on the connecting rod 223.

When the electric motor is energized using the diopter adjustment switch 207 or 208 to rotate the electric motor 220, the interaction between the gear 222 and rack 224 causes the connecting rod 223 to move along the axis thereof. As as result, the eyepiece frame 203 connected via the adjustment base 204 moves along the optical axis O in FIG. 30. The control sequence of the electric motor 210 or 220 will be described later.

The control sequence of an ultrasonic motor or electric motor mentioned above will be described.

Figure 31:
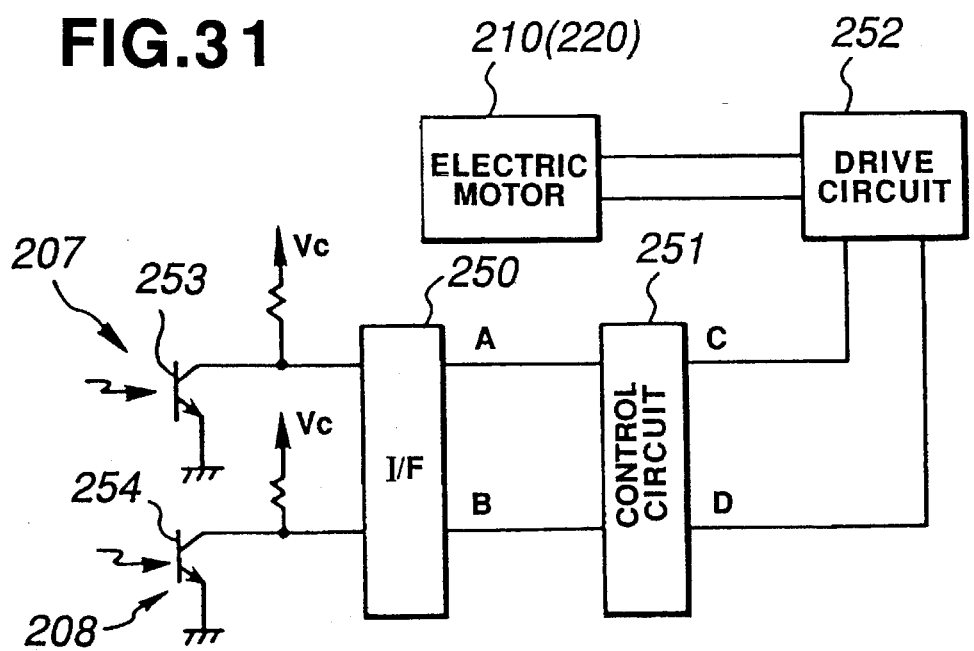

First, the control sequence of the electric motor 210 (220) will be described in conjunction with FIGS. 31 and 32. FIG. 31 is a block diagram.

The diopter adjustment switch 207 or 208 formed on the operational part 12C is connected to an interface 250. Outputs A and B of the interface 250 are input to a control circuit 251. Outputs C and D of the control circuit 251 are input to a drive circuit 252.

The output A or B of the interface 250 assumes a high level or low level depending on the quantity of light input to a phototransistor 253 or 254 mounted in the light receiver of the switch 207 or 208.

The high level represents an on state, while the low level represents an off state. As shown in FIG. 32, the control circuit 251 checks the levels of the outputs A and B of the interface 250, and provides outputs C and D, which have been binary-coded according to the results of the check, to the drive circuit 252.

Figure 32:
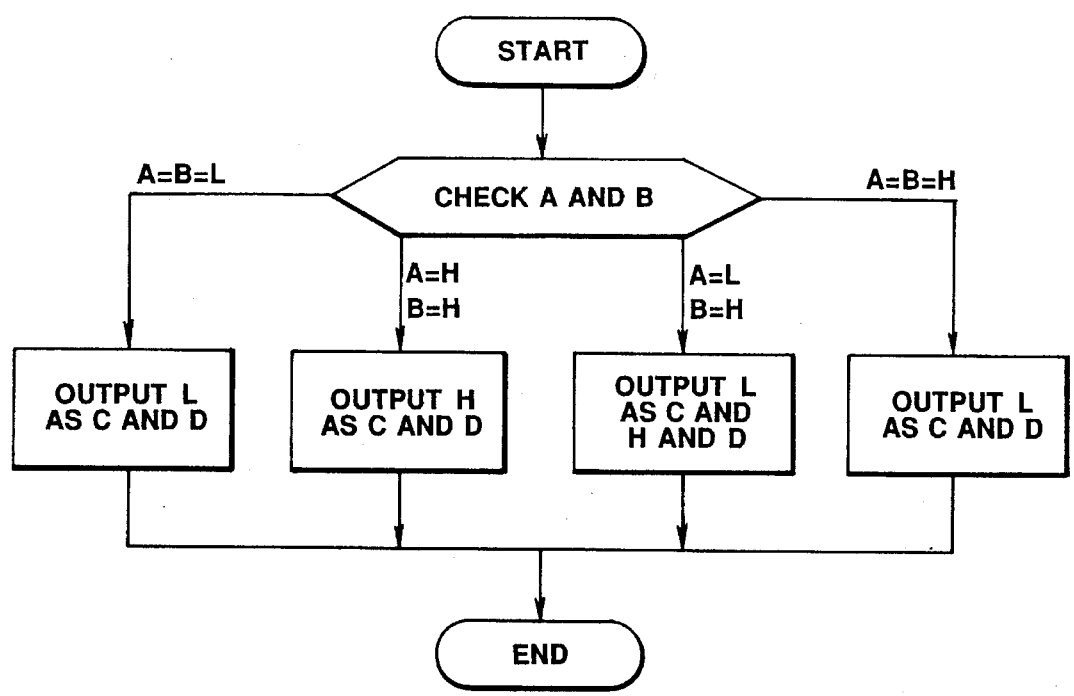

The control circuit 252 receives low or high-level outputs from the control circuit 251 according to the results of the check shown in FIG. 32. At this time, a signal defining the direction of rotation; that is, rotation or reversion is provided as the output C, while a signal defining an on or off state is provided as the output D.

The control circuit 252 controls the motor 210 (220) in such a manner that:

when the outputs C and D are high, the connecting rod will move up above the middle position in FIG. 28 or 30;

when the output C is low and the output D is high, the connecting rod will move down below the middle position; and when the outputs C and D or low, the motor will stop.

Figure 33:
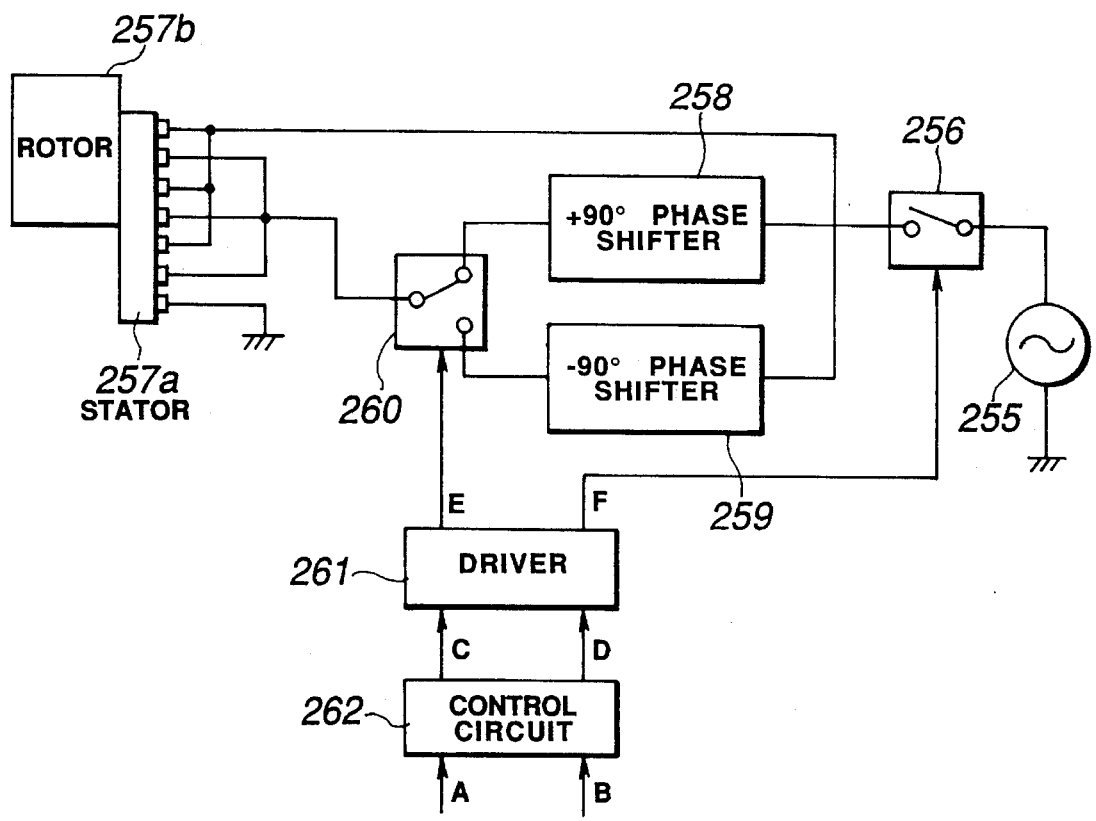

Next, the control sequence of an ultrasonic motor will be described. FIG. 33 is a block diagram. A sine-wave generator 255 is connected to a first set of electrodes adhering to a stator 257a via a first relay 256. The sine-wave generator 255 is also connected to a second set of electrodes adhering to the stator 257a via a +90° phase shifter 258, −90° phase shifter 259, and a second relay 260 which are connected in parallel with the sine-wave generator 255. Herein, the first set of electrodes and the second set of electrodes are arranged in a row and in turn.

A driver 261 provides outputs according to the outputs C and D of the control circuit 262 in such a manner that:

when the output C is low, the output E will be low;

when the output C is high, the output E will be high;

when the output D is low, the output F will be low; and when the output D is high, the output F will be high.

The relays 256 and 260 are turned on with high inputs, but turned off with low inputs.

The inputs A and B of the control circuit 262, and the outputs C and D of the control circuit 262 are identical to those shown in FIGS. 31 and 32. The description will be omitted.

Due to the aforesaid configuration, switching provides the stator 257a with an output of the sine-wave generator 255 and with a signal +90° out of phase with the output. The stator 257a then generates progressive waves triggering an up or down movement. With the progressive waves, a rotor 257b moves up or down. The rotor 257b may be fixed to or used in conjunction with the aforesaid connecting rod 205.

The coverable endoscope 2A or 2C in the aforesaid first or second embodiment is of a type that when switching is performed, the bending section is bent using an electric motor. The first or second embodiment is not limited to this type of endoscope, but may apply to a covered endoscope 2C' of a variant shown in FIG. 34 in which angulation knobs 230 and 231 are manipulated to pull an operation wire linked with the bending section 20C, and thus the bending section is bent.

The covered endoscope 2C' consists of, similarly to the covered endoscope 2C shown in FIG. 25a, an insertional part 11C made up of a distal part 19C, a bending section 20C, and a flexible part 40C, an operational part 12C formed at the proximal end of the insertional part 11C, an eyepiece unit 215 formed on the top of the operational part 12C, and a light guide cord 13C extending from the side of the operational part 12C. The covered endoscope 2C" differs from the covered endoscope 2C in the angulation mechanism of the operational part 12C.

Figure 35:
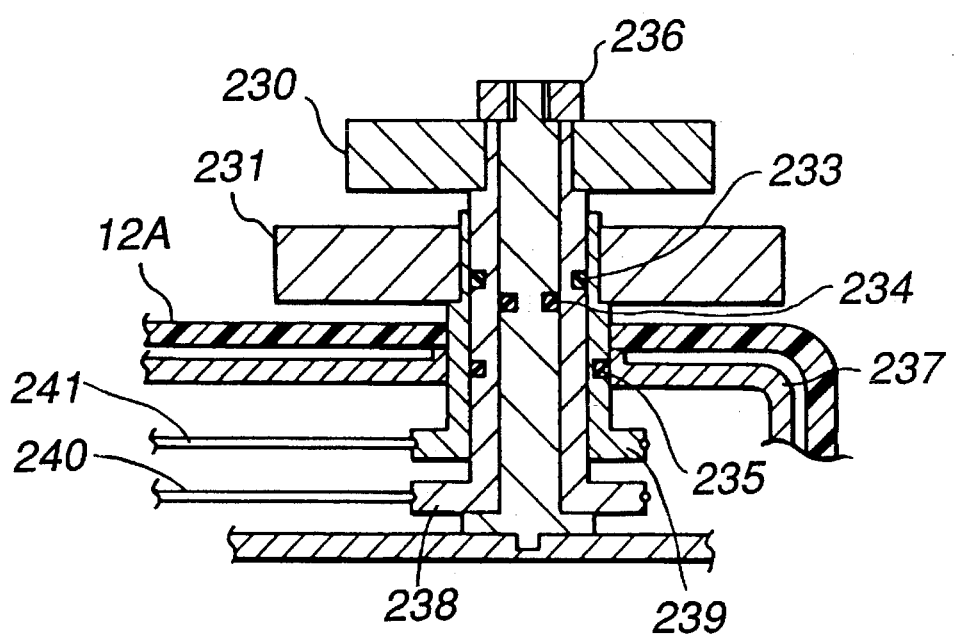
FIG. 35 is a cross-sectional view of the angulation knobs of FIG. 34.

As shown in FIG. 35, seals 233, 234, and 235 are attached to the areas of the angulation knobs 230 and 231 for activating up, down, right, and left bending which border on the inside of the operational part 12C and on the outside, thus providing a structure permitting tight shutout of water. The angulation knobs 230 and 231 can be detached by removing a setscrew 236.

Figure 34:
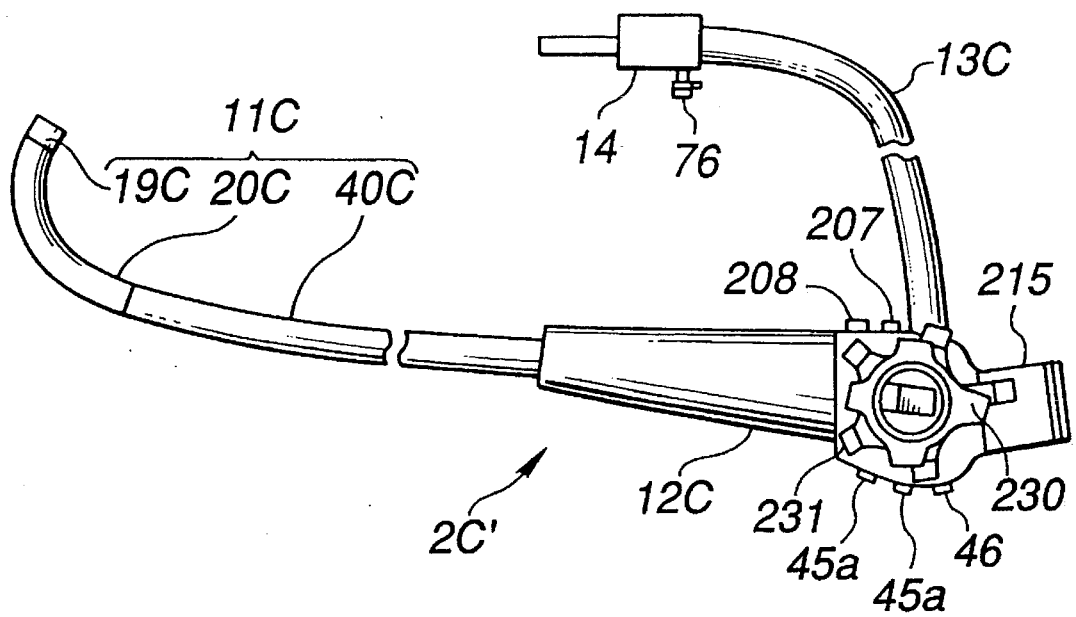
FIG. 34 shows a fiberscope in a variant of the second embodiment in which angulation knobs are used for manual bending.

When the above mechanism is employed, the aforesaid diopter adjustment switches 207 and 208 are arranged as shown in FIG. 34.

237 in FIG. 35 denotes an armor of the operational part. 240 and 241 denote bending wires. When the angulation knob 230 (or 231) is rotated, a pulley 238 (or 239) rotates. With the rotation, a bending wire 240 (or 241) advances or withdraws. Thus, the bending section 20C can be bent.

The aforesaid first and second embodiments, and variant may be combined to form different embodiments.

Next, a covered endoscope that permits excellent insertional operability even when an insertion aid is used will be described.

When an endoscope is to be inserted into the large intestine or other luminal organ, an insertion aid is sometimes attached to the insertional part in a bid to upgrade the insertional smoothness.

The insertion aid is not used from the beginning of examination. For example, after an insertional part reaches the vicinity of a certain region in a body cavity, for example, the surface-density area of the large intestine, when the sigmoid colon is stretched substantially linearly, an insertion aid is advanced along the insertional part to the body cavity. Thus, the insertion aid is used to hold the sigmoid colon substantially linearly and upgrade insertional smoothness.

In this case, the insertion aid is attached to the insertional part from the distal end of the insertional part. The insertion aid must be attached to the insertional part before examination is started. For a period from the start of examination until the start of using the insertion aid, the insertion aid is present outside a patient's body and put on the insertional part that has not been inserted.

The insertion aid is not fixed to either an endoscope cover or an endoscope-cover coverable endoscope. The insertion aid moves freely along the axis of the insertional part.

The free movement of the insertion aid cripples an operator's inserting maneuver. This greatly deteriorates operability and weights an operator's load. An increase in an inserting time span resulting from the deteriorated operability causes a patient excessive pain.

Embodiments to be described below attempt to solve the foregoing drawbacks and realizes an endoscope cover-sheathed endoscope that even when an insertion aid is put on the insertional part, enables reduction of an operator's load and alleviation of a patient discomfort without impairing the operability.

Figure 36:
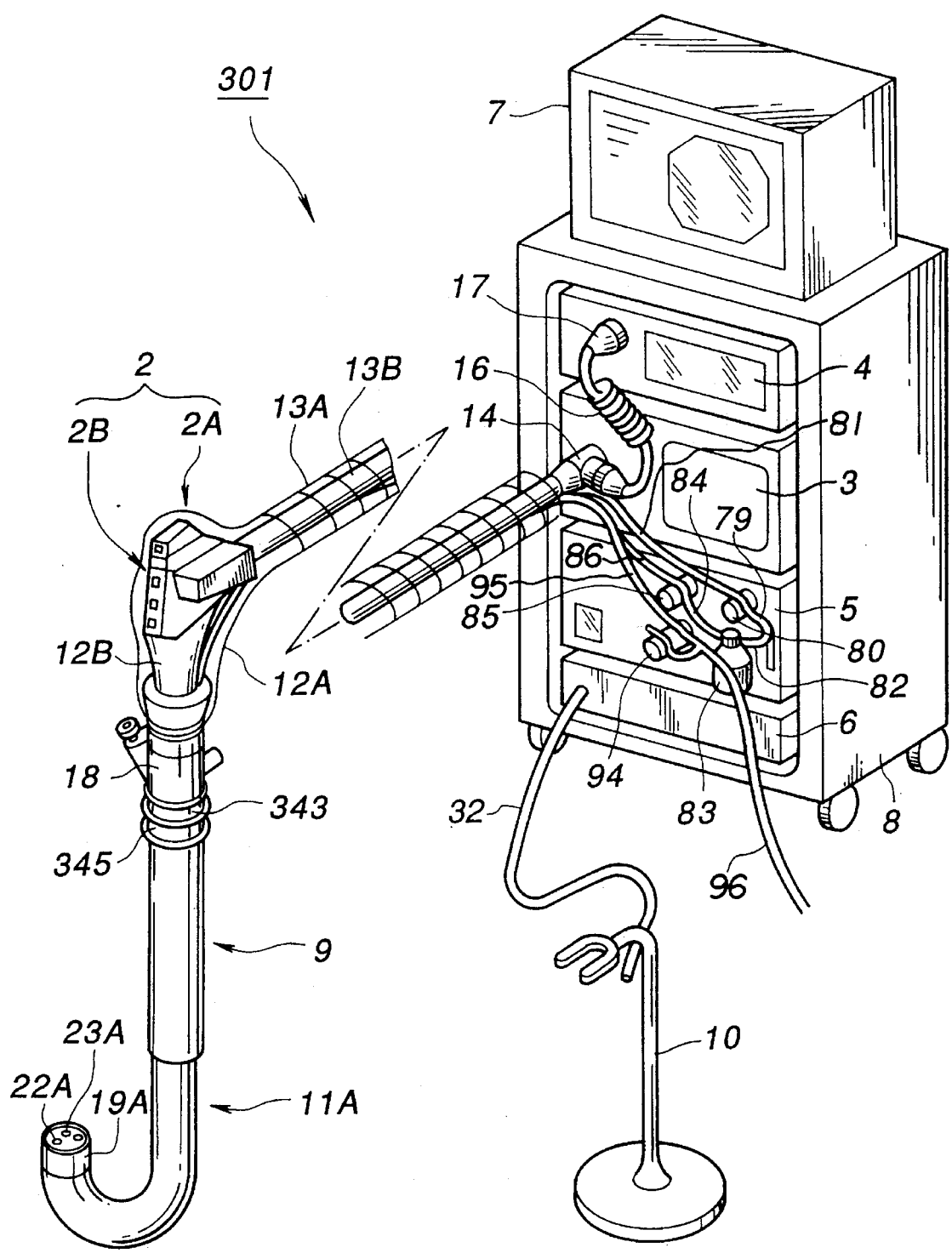
FIGS. 36 to 38 relate to the third embodiment of the present invention.
Figure 37:
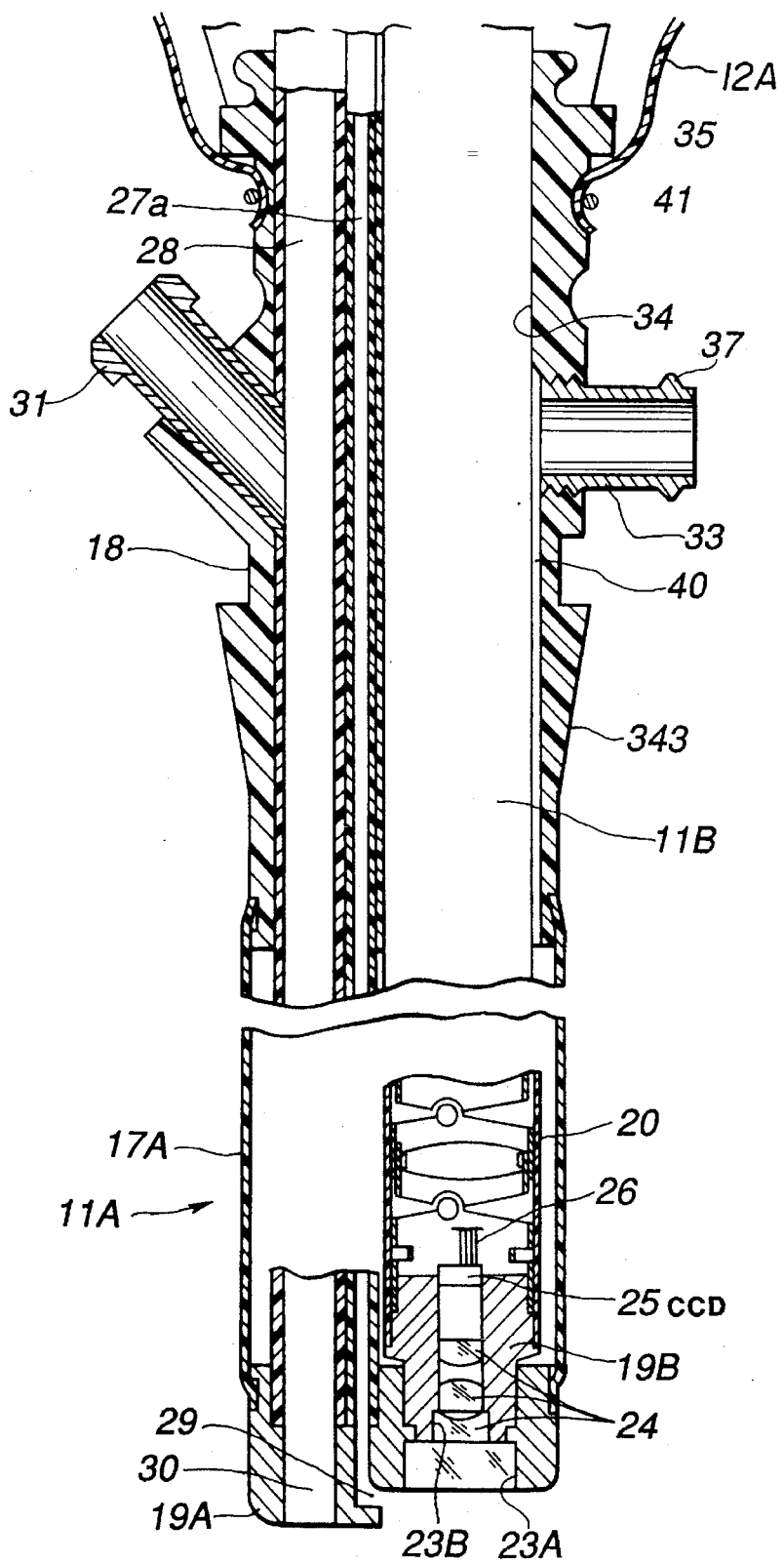

In FIG. 36, an endoscope cover-sheathed endoscope system 301 in which the third embodiment of the present invention is implemented comprises a coverable endoscope 2 made up of a cover 2A and a coverable endoscope 2B to be sheathed with the cover 2A, a light source apparatus 3 for supplying illumination light to the coverable endoscope 2B, a video processor 4 for processing signals acquired by an imaging means incorporated in the coverable endoscope 2B, a fluid control apparatus 5 for supplying air or water through a tube in the cover 2A, a cover dilator 6 for use in sheathing the coverable endoscope 2B with the cover 2A, a monitor 7 for displaying video signals processed by the video processor 4, and an insertion aid 9 to be put on the insertional part cover 11A of the cover 2A for use. The light source 3, video processor 4, fluid control apparatus 5, and cover dilator 6 are stored in a cart 8, and the monitor 7 is placed on the top of the cart 8.

One of the features the endoscope system 301 has is that the insertion aid 9 put on the cover 2A is included in the endoscope system 1 (See FIG. 1) having the first embodiment. The other feature is that the cover 2A has an immobilization mechanism for immobilizing the proximal end of the insertion aid 9 on the cover 2A. The other components are almost identical to those in the first embodiment, and will therefore bear the same numerals. The description will be omitted.

The coverable endoscope 2B is structured to tightly shut out water.

This embodiment is characterized by the cover 2A having the immobilization mechanism for immobilizing the proximal end of the insertion aid 9 on the cover 2A, which will be described below.

As shown in FIG. 36, the distal end of the operational part locking cap 18 has a tapered section 343 whose diameter grows gradually larger from the distal end toward the proximal end. The tapered section 343 is tapered so that the outer diameter thereof will be smaller in the distal portion thereof than the inner diameter of a cylindrical grip 345 which is formed at the proximal end of a flexible tube member 344, and be larger at the proximal end thereof.

When the insertion aid 9 such as a mouthpiece and sliding tube, which is put on an insertional part cover 11A for use, is moved from the distal end of the insertional part cover 11A toward the operational part locking cap 18, which is the proximal part of the insertional part cover 11A, along the axis of the insertional part cover 11A, the inner surface of a back end 346 of the grip 345 of the insertion aid 9 abuts on the tapered section 343. The insertion aid 9 is then substantially attached to the tapered section 343.

The frictional force occurring in the area to which the insertion aid 9 is attached restricts the movement of the back end 346 of the grip 345 of the insertion aid 9. As a result, the insertion aid 9 is immobilized by the tapered section 343 so as not to move freely or becomes stationary. During an operator's maneuver, since the insertion aid 9 does not move unexpectedly, it can be held in a state not interrupting with the operator's maneuver.

Figure 38:
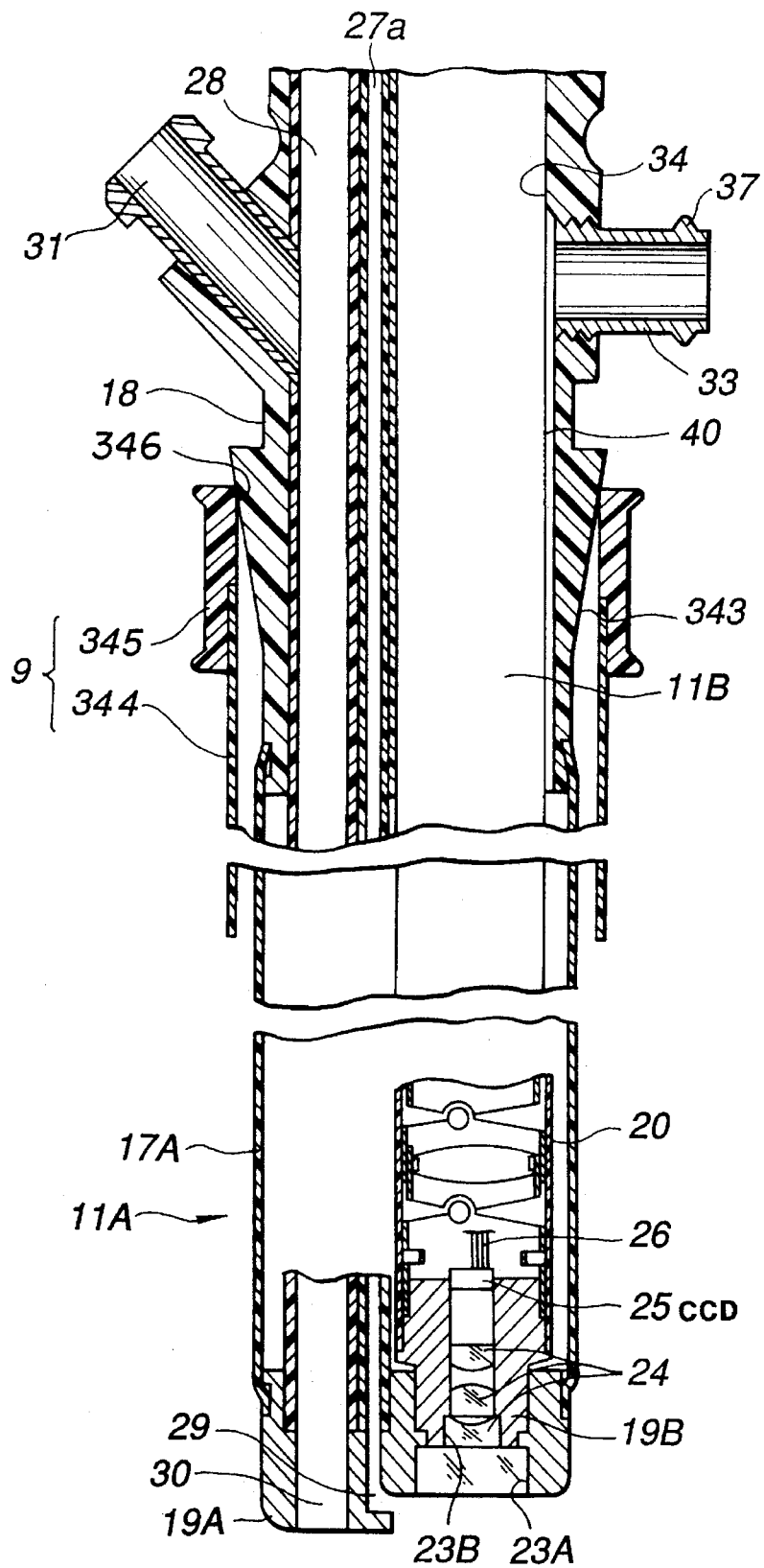
Figure 39:
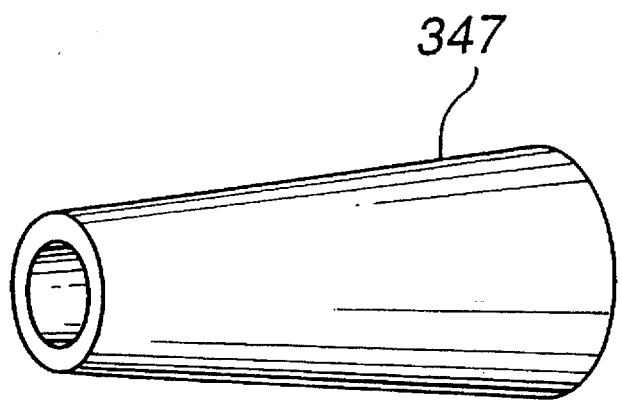
FIG. 39 is an oblique view showing a tapered member in a variant of the third embodiment of the present invention.
Figure 40:
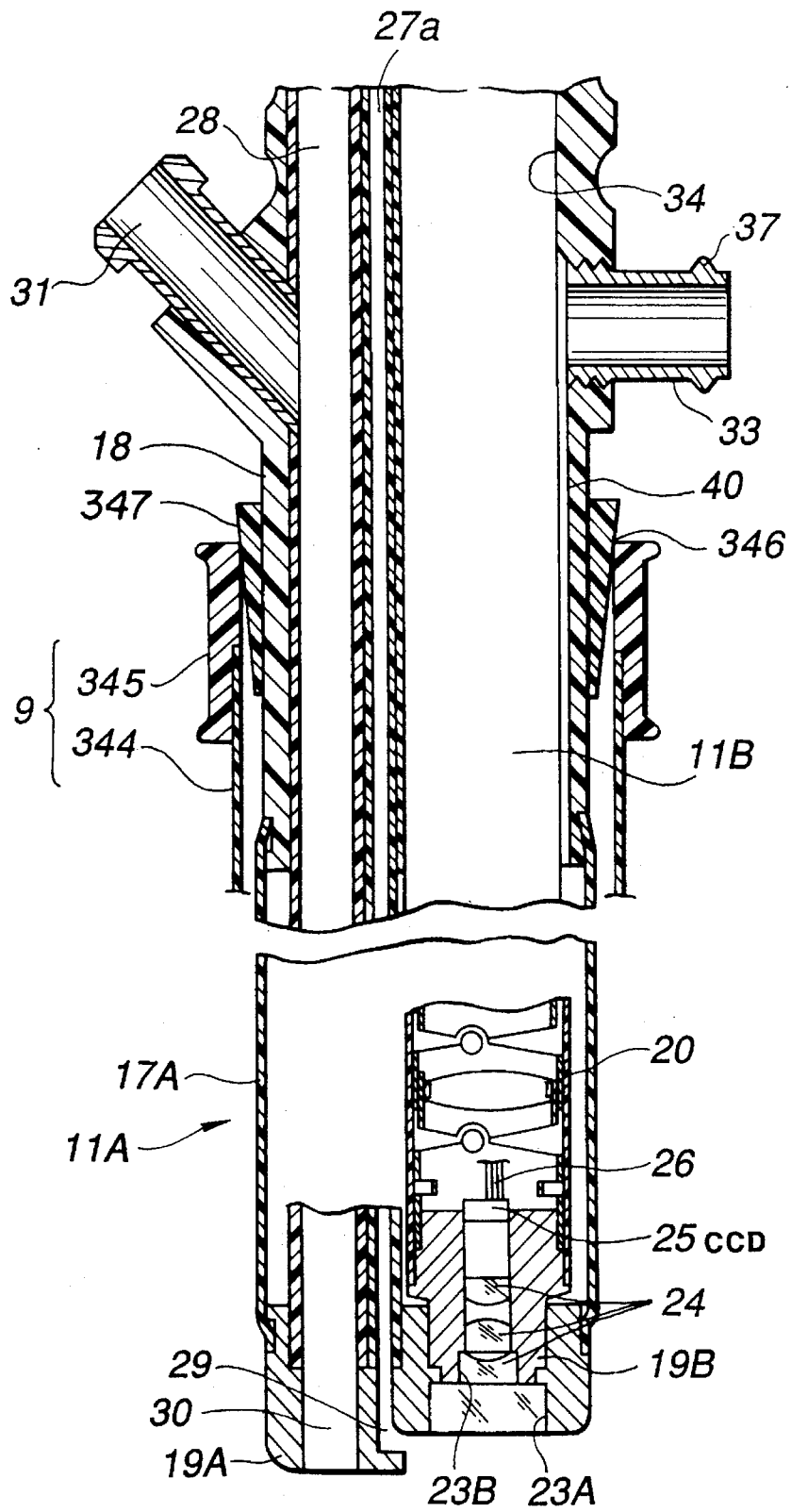
FIG. 40 is a cross-sectional view showing a structure of a covered endoscope with an insertion aid attached using the tapered member shown in FIG. 39.

In the above description, the tapered section 343 and operational part locking cap 18 are united. A tapered member 347 tapered as shown in FIG. 39 may be attached to the distal end of the operational part locking cap 18 by applying adhesive or pressure. This provides a structure shown in FIG. 40 and thus forms a mechanism for immobilizing the insertion aid 9 similarly to that shown in FIG. 38.

The tapered member 347 and operational part locking cap 18 may be made of, for example, an elastic material such as fluoro rubber, which will further improve the capacity for immobilizing the insertion aid 9.

Due to the tapered shape, the durability of the tapered member 347 against a bending force varies along the axis thereof. Even when a bending force is applied to the distal portion of the operational part locking cap 18, the force will not converge. This means that the insertional part cover 11A and insertional part 11B will be prevented from buckling.

Next, the fourth embodiment of the present invention will be described with reference to FIGS. 41 to 44.

This embodiment differs from the third embodiment in only the shape of an operational part locking cap. Components identical to those in the third embodiment will bear the same numerals. The description will be omitted.

Figure 41:
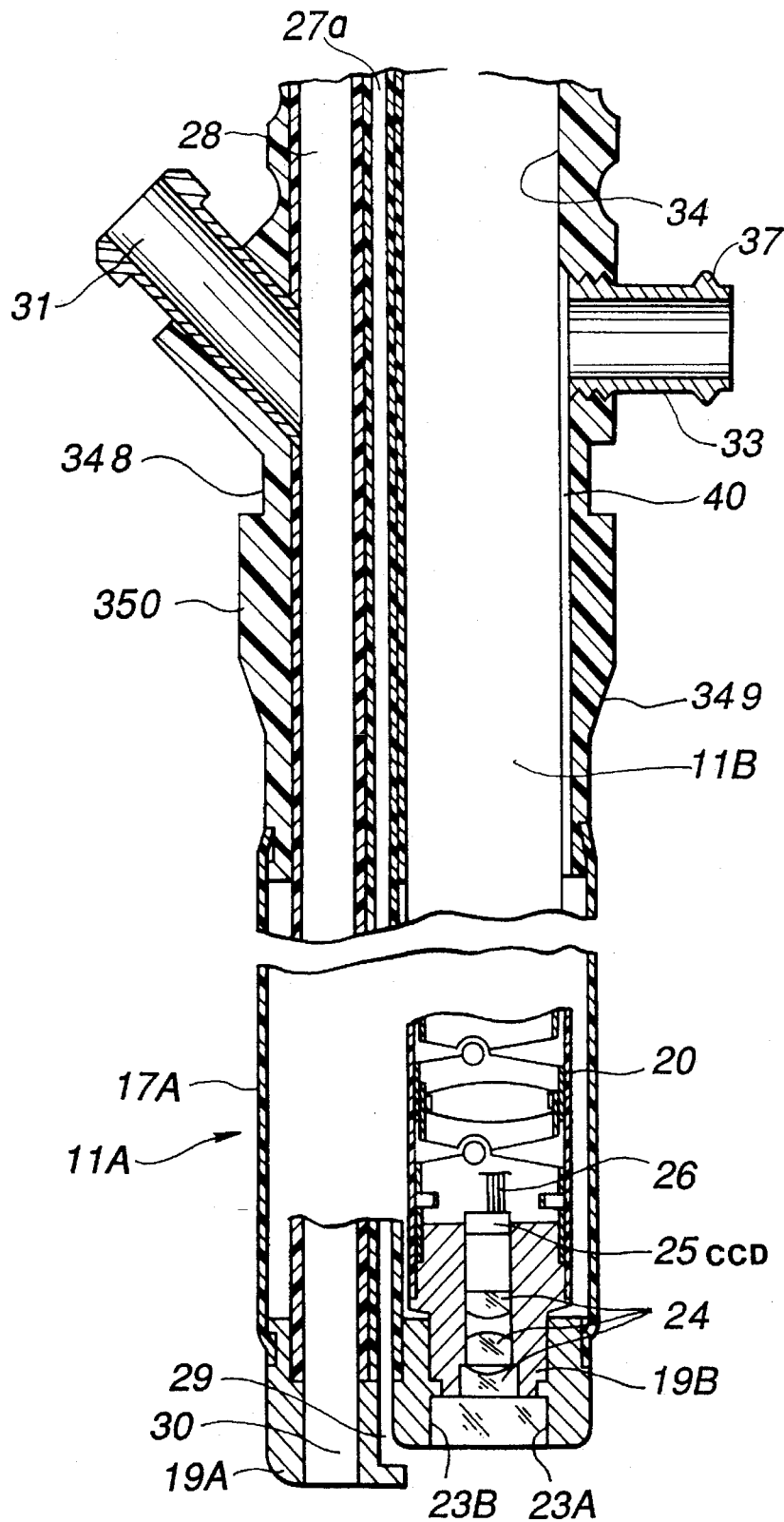
FIG. 41 is a cross-sectional view showing a structure of a covered endoscope in the fourth embodiment of the present invention.

As shown in FIG. 41, the distal portion of the operational part locking cap 348 includes a tapered section 349 whose diameter grows larger from the distal end of the locking cap 348 toward the proximal end thereof. The proximal portion of the locking cap 348 beyond the tapered section 349 has a cylindrical section 350. The outer diameter of the cylindrical section 350 is substantially the same as the inner diameter of the grip 345 of the insertion aid 9.

Figure 42:
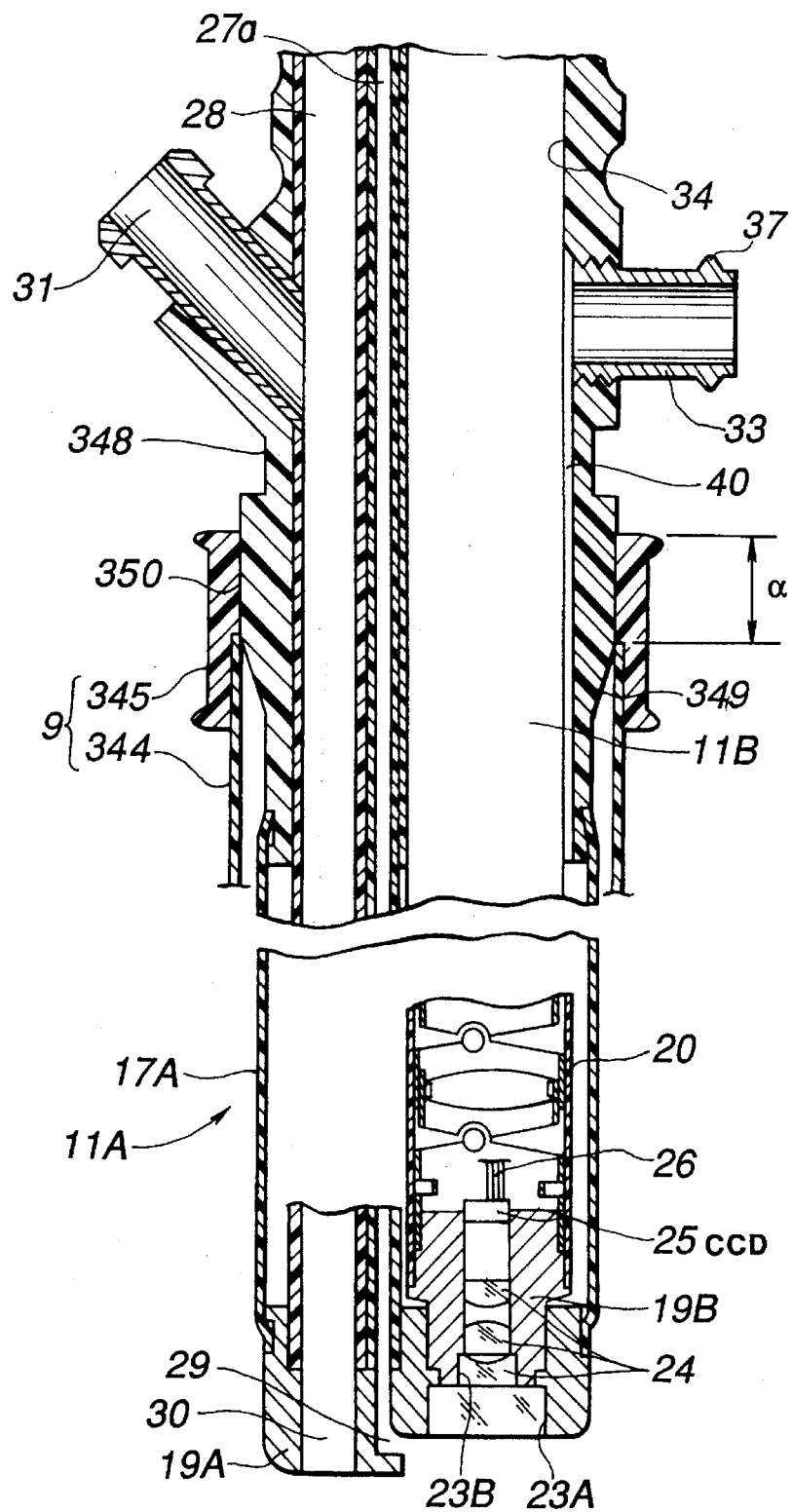
FIG. 42 is a cross-sectional view showing a structure of a covered endoscope of the fourth embodiment with an insertion aid attached.

Owing to the foregoing shape, when the insertion aid 9 is moved toward the operational part locking cap 348 along the axis of the insertional part cover 11A, the grip 345 moves along the tapered section 349 to the cylindrical section 350. The insertion aid 9 is then attached and immobilized. Since the insertion aid 9 is thus attached, the length of attachment, α, can be made longer as shown in FIG. 42. This means that the insertion aid 9 can be secured stably and reliably.

Figure 43:
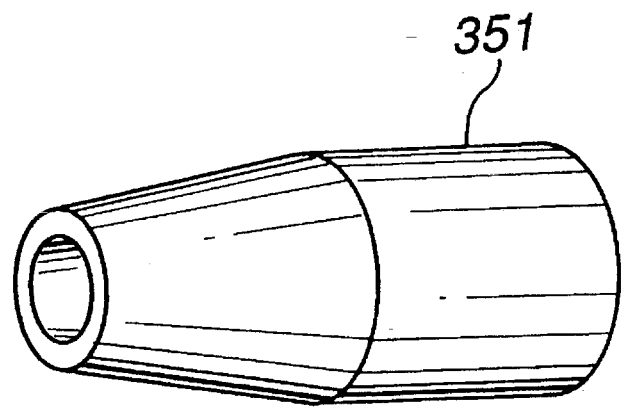
FIG. 43 is an oblique view showing a tapered member in a variant of the fourth embodiment of the present invention.
Figure 44:
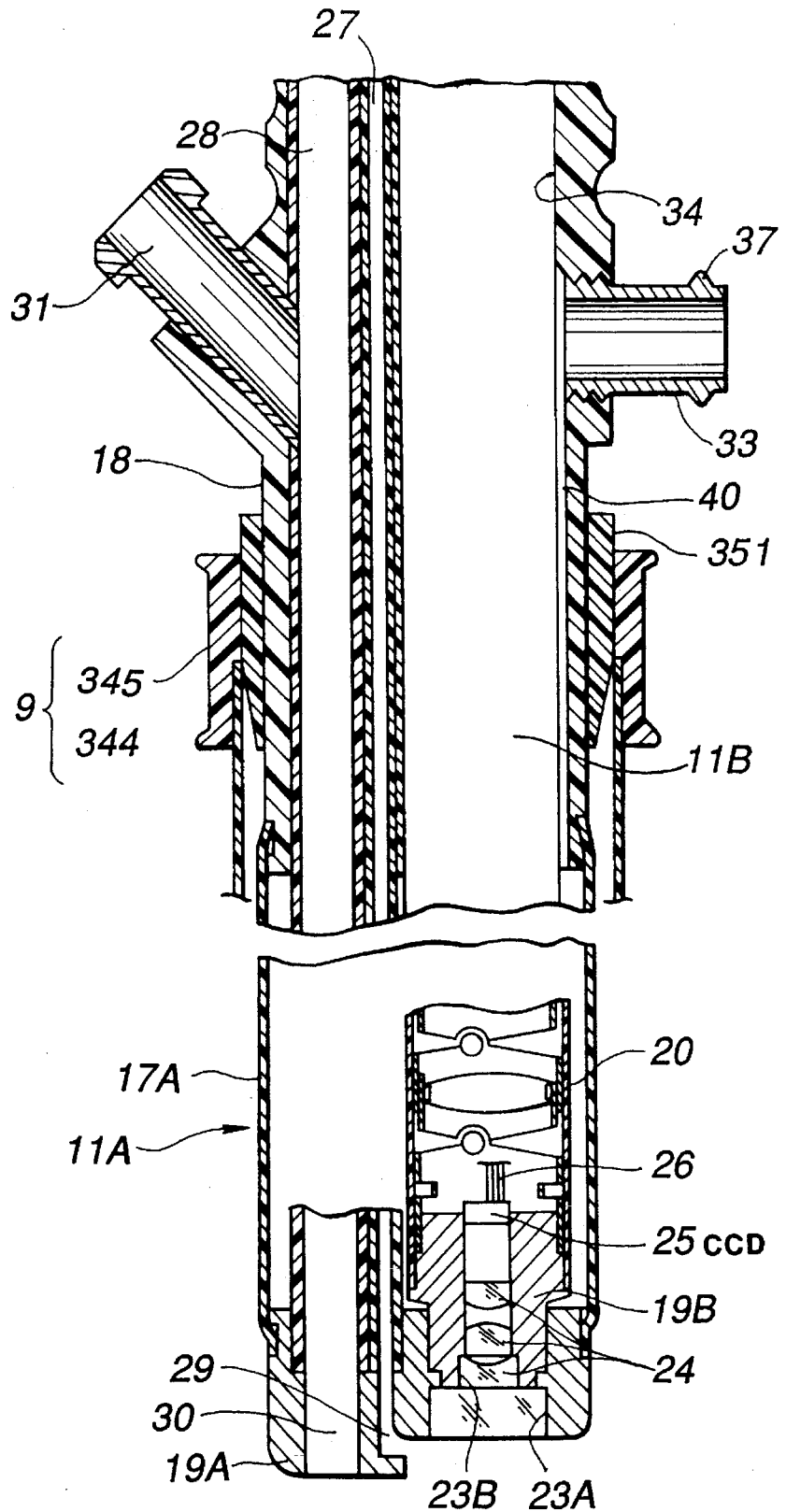
FIG. 44 is a cross-sectional view showing a structure of a covered endoscope with an insertion aid attached using the tapered member shown in FIG. 43.

In this embodiment similarly to the third embodiment, an insertion aid immobilization area made up of the tapered section 349 and cylindrical section 350 is provided as part of the operational part locking cap 348. An immobilization member 351 which is shown in FIG. 43 made up of a tapered section and a cylindrical section may be attached to the operational part locking cap 348 by applying adhesive or pressure, thus immobilizing the insertion aid 9 as shown in FIG. 44. Alternatively, multiple immobilization members 351 whose cylindrical sections have different outer diameters may be made available so that an optical one thereof can be used depending on the inner diameter of the grip 345 of the employed insertion aid 9.

Figure 45:
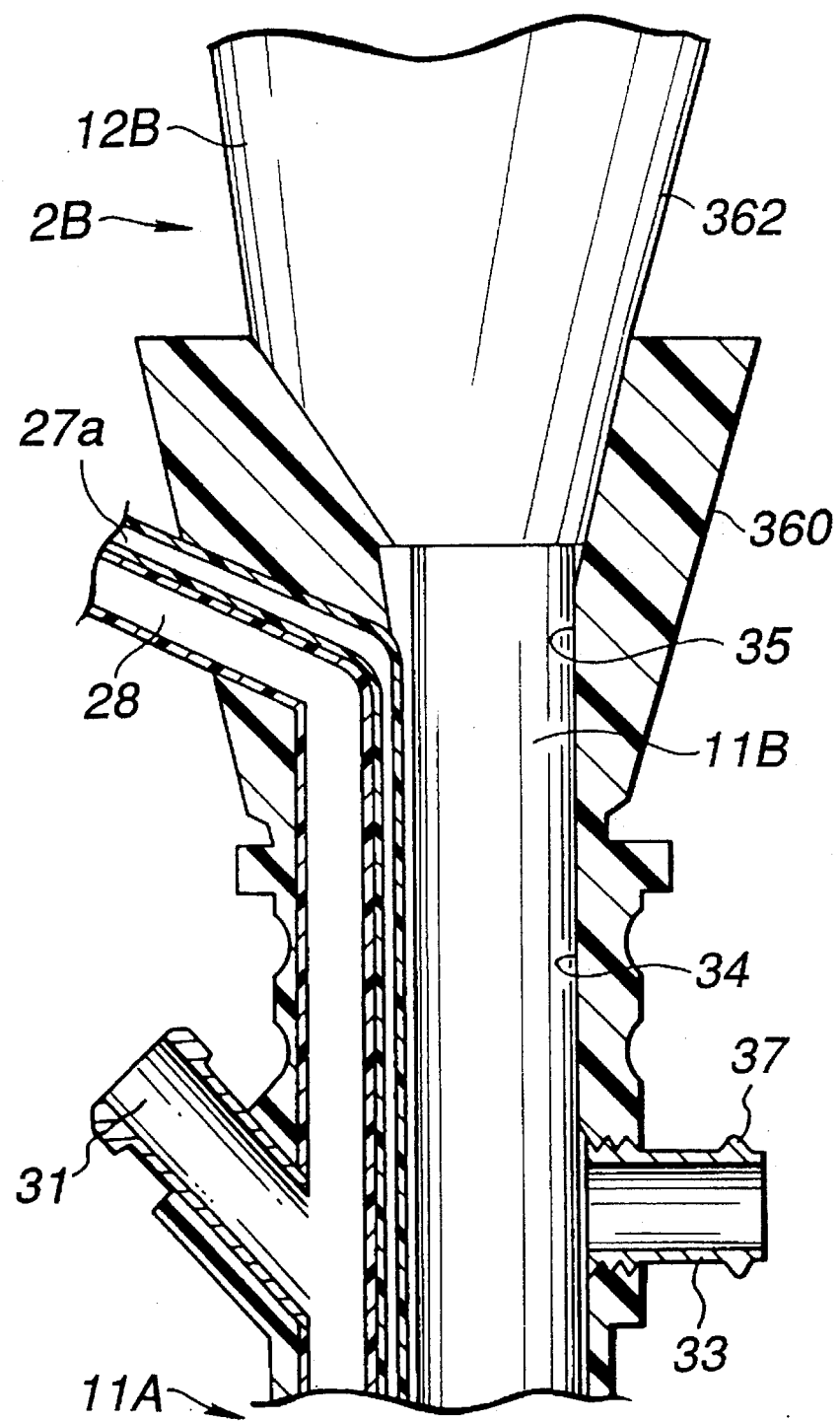
FIGS. 45 to 51 relate to the fifth embodiment of the present invention.

FIG. 45 shows a major portion of the cover 2A in the fifth embodiment of the present invention.

An operational part locking cap 360 formed in the proximal portion of an insertional part cover 11A has, as shown in FIG. 45, the proximal portion projected upward. The proximal portion is mated and secured with a receiver 362 formed in the operational part 12B of the coverable endoscope 2B. Owing to elastic deformation by which the operational part locking cap 360 is characterized, the proximal portion thereof is secured firmly.

The insertional part cover 11A is disposable or usable for each patient, while the coverable endoscope 2B is used repeatedly. The receiver 362 of the coverable endoscope 2B must be durable enough to withstand repeated attachment and detachment of the insertional part cover 11A.

From this viewpoint, the operational part locking cap 360 of the insertional part cover 11A is made of a material having a relatively low wear resistance; such as, polyester resin or phenolic resin, while the receiver 362 of the operational part 12B is made of a material having a relatively high wear resistance; such as, nylon resin, polycarbonate resin, polysulfone resin, denatured polyophenylene oxide resin, or metal. The receiver 362 will therefore not be worn out with repeated attachment and detachment of the insertional part cover 11A.

Endoscopic examination includes not only observation but also collection of tissues of a lesion, and treatment including resection of and recovery from a polyp. An endoscope having two channels or an endoscope having a channel with a large inner diameter is therefore used selectively.

If multiple types of covers having different channel diameters and different numbers of channels are made available, even a covered endoscope can cope with various kinds of treatment and examination.

When multiple types of covers, and multiple types coverable endoscopes associated with the multiple types of covers are used in combination, if a user uses an incorrect combination of a cover and a coverable endoscope, the cover may be torn, or the user may be unaware of the fact that the cover has been torn out and proceed with examination. Eventually, the coverable endoscope is contaminated. In attempts to root out this kind of accident, a cover and a coverable endoscope in the fifth embodiment of the present invention are constructed as described below.

Figure 46:
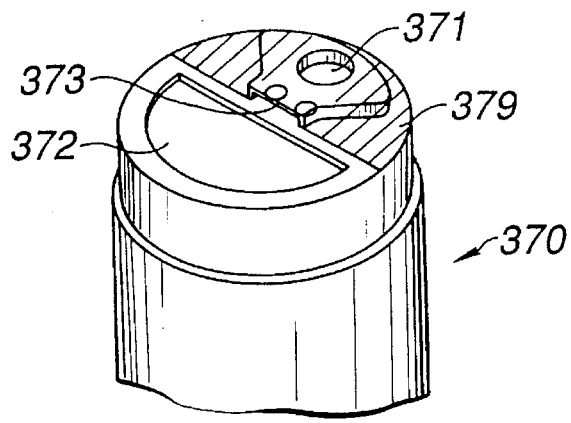

A first insertional part cover 370 shown in FIG. 46 includes a forceps channel 371, an endoscope insertion channel 372, and an air/water nozzle 373.

Figure 47:
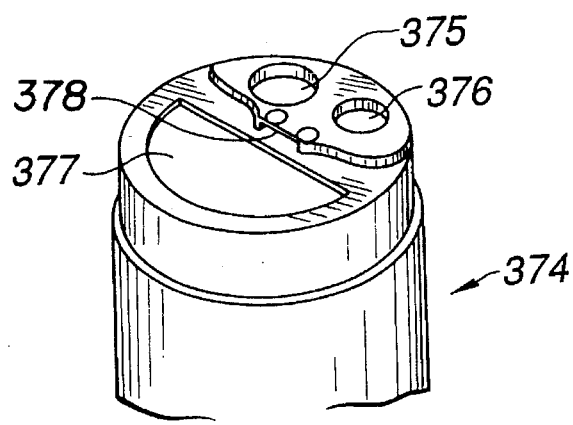

A second insertional part cover 374 shown in FIG. 47 has two forceps channels 375 and 376, an endoscope insertion channel 377, and an air/water nozzle 378. In FIGS. 46 and 47, illumination windows 22A are not shown (that is to say, the distal end of the endoscope insertion channels 372 and 377 are blocked actually but appears unblocked).

The two forceps channels 375 and 376 mounted in the insertional part cover 374 shown in FIG. 47 is realized by making the most of a dead space 379 hatched in FIG. 46.

Figure 49:
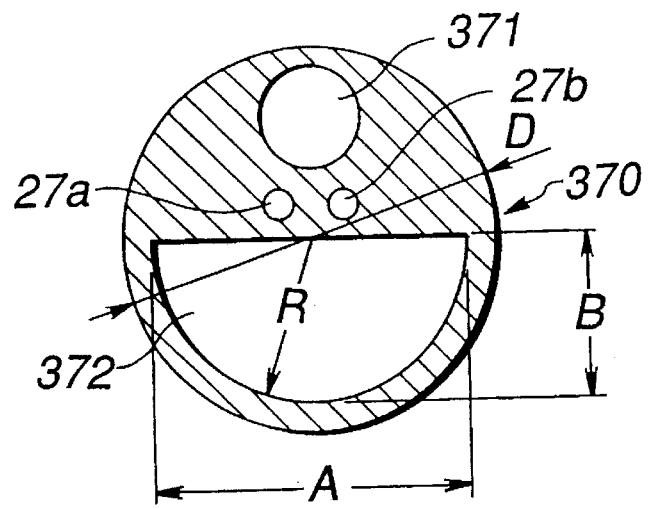
Figure 50:
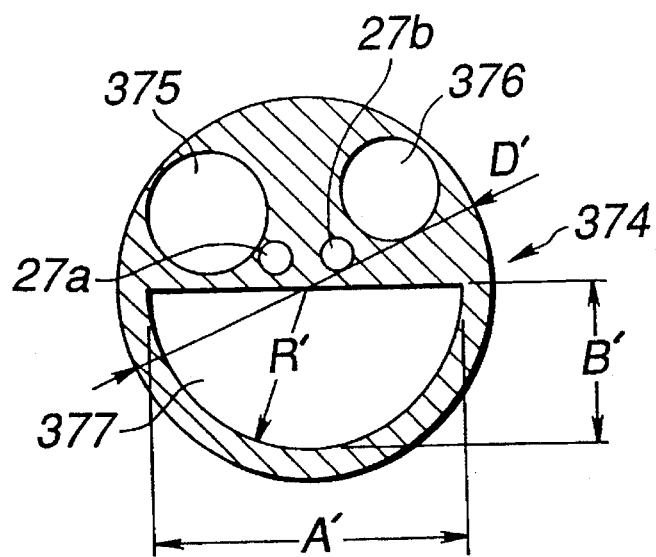

On the cross sections of the insertional part cover 370 and insertional part cover 374 shown in FIGS. 49 and 50, the outer diameters D and D', the widths A and A', and heights B and B' of the endoscope insertion channels 372 and 377 mounted in the respective insertional part covers, and the inner diameters R and R' of the arcs of the endoscope insertion channels 372 and 377 are the same respectively (D=D', A=A', B=B', and R=R'). Namely, the endoscope insertion channels 372 and 377 are congruent.

Figure 48:
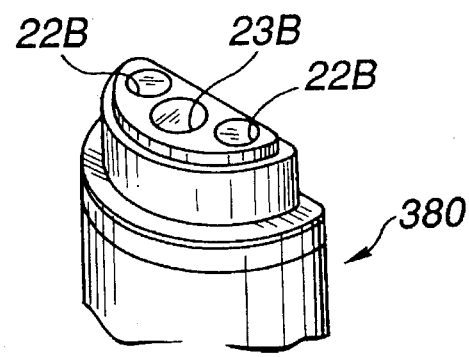
Figure 51:
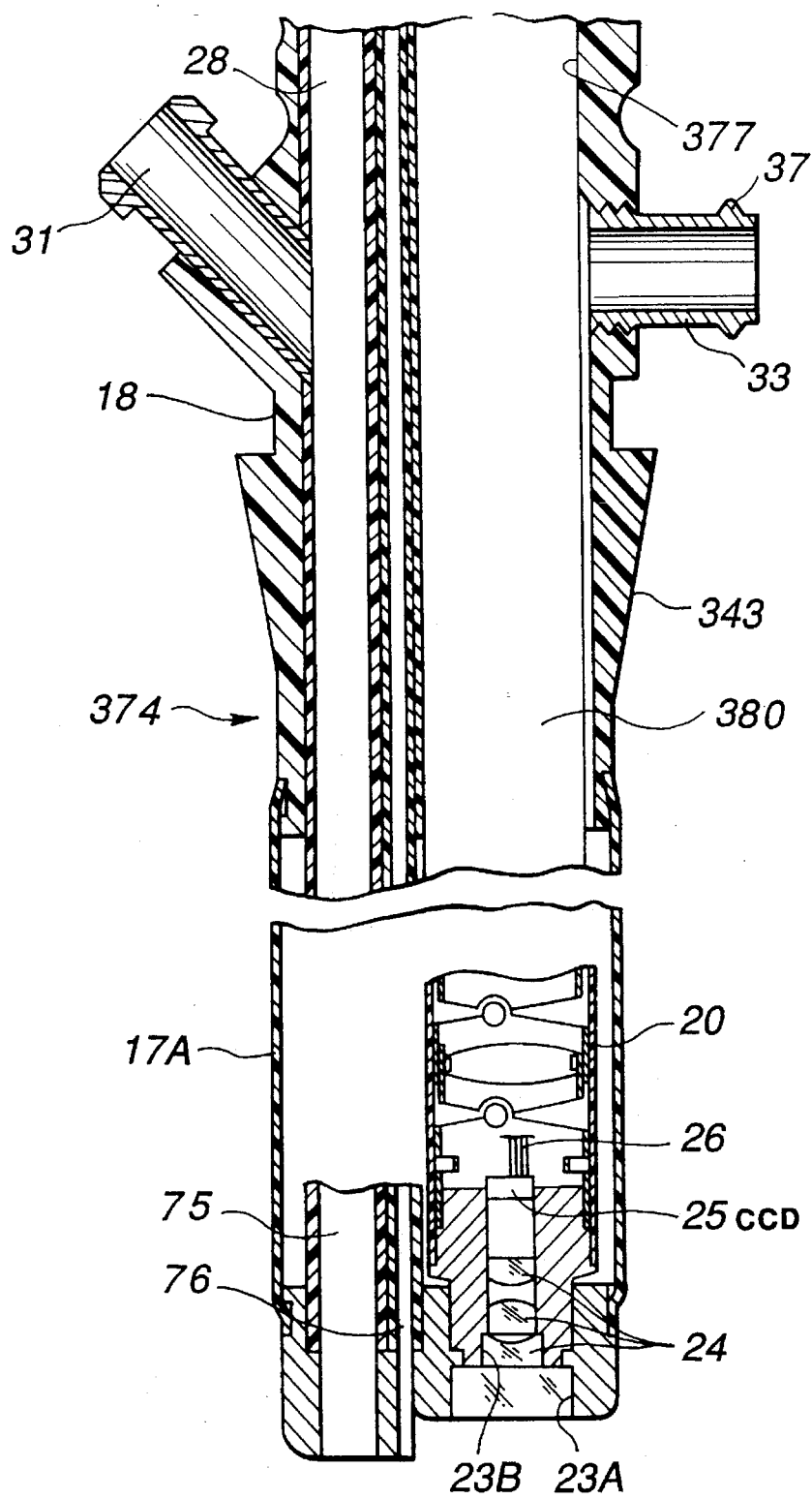

FIG. 51 shows a longitudinal cross section of the insertional part cover 374 with a coverable endoscope inserted. An insertional part 380 of a coverable endoscope shown in FIG. 48 can be inserted into either the endoscope insertion channel 372 or 377. As long as endoscope insertion channels have specified dimensions, coverable endoscopes having the same shape and dimensions are interchangeable among multiple kinds of covers having different channel diameters and different numbers of channels.

When a single covered endoscope is available, any one of covers having different channel diameters and different numbers of channels can be used selectively. It becomes therefore unnecessary to purchase multiple covered endoscopes having different specifications. Specifications; such as, the number of optical systems, a channel diameter, and the number of channels can be defined freely. Furthermore, such an accident that a cover is torn because of an incorrect combination of a cover and a coverable endoscope or that a coverable endoscope is contaminated can be prevented successfully.

The aforesaid fourth and fifth embodiments, and variant relate to a coverable endoscope that is an electronic endoscope. The present invention can apply in substantially the same manner to an optical coverable endoscope in which an image guide is used on behalf of an imaging device and an eyepiece is used for observation (that is, a coverable fiberscope).

An endoscope usable in conjunction with the cover 2A is not limited to the coverable endoscope 2B, but may be an endoscope that is used without the cover 2A; that is, with bare body.

Next, a channeled endoscope cover-sheathed endoscope of the sixth embodiment having a forceps raiser capable of raising forceps at a large angle will be described.

Figure 52:
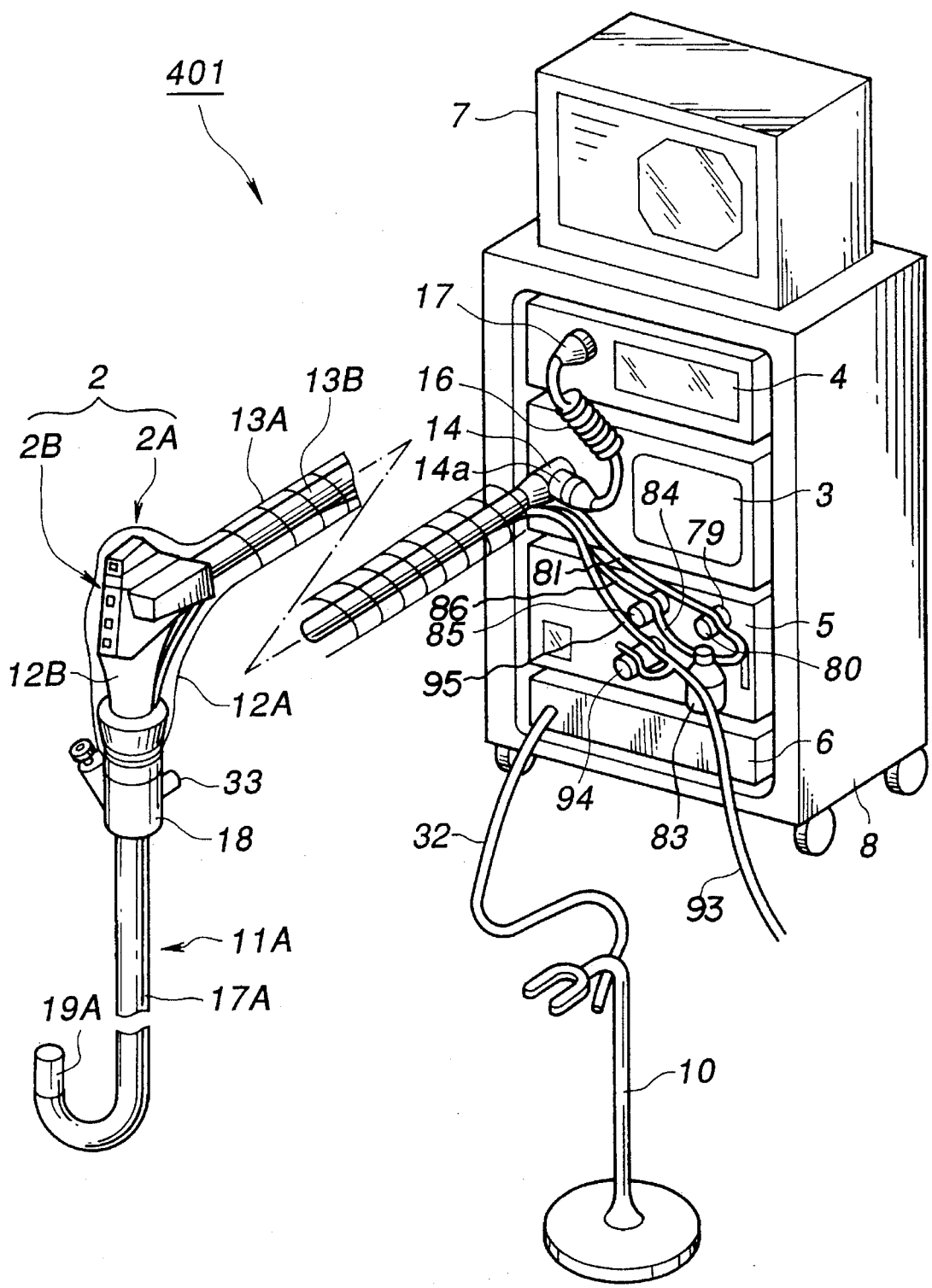
FIGS. 52 to 61 relate to the sixth embodiment.

As shown in FIG. 52, an endoscope cover-sheathed endoscope system 401 comprises a covered endoscope 2 of the sixth embodiment made up of a cover 2A and a coverable endoscope 2B to be sheathed with the cover 2A, a light source apparatus 3 for supplying illumination light to the coverable endoscope 2B, a video processor 4 for processing signals acquired by an imaging means incorporated in the coverable endoscope 2B, a fluid control apparatus 5 for supplying air or water through a tube in the cover 2A, a cover dilator 6 for use in sheathing the coverable endoscope 2B with the cover 2A, and a monitor 7 for displaying video signals processed by the video processor 4.

Figure 55:
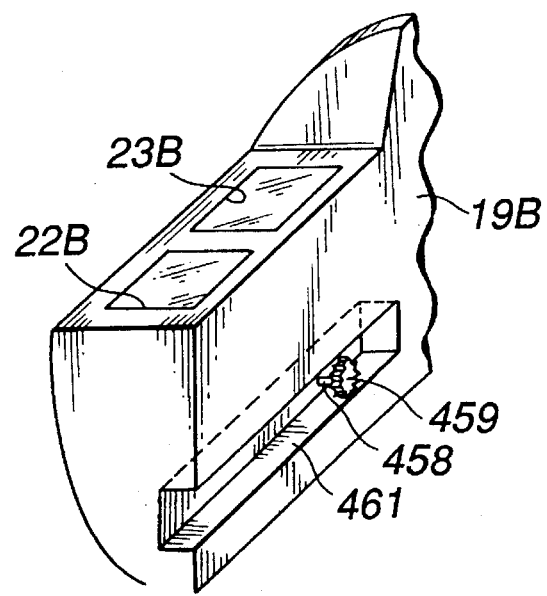
Figure 56:
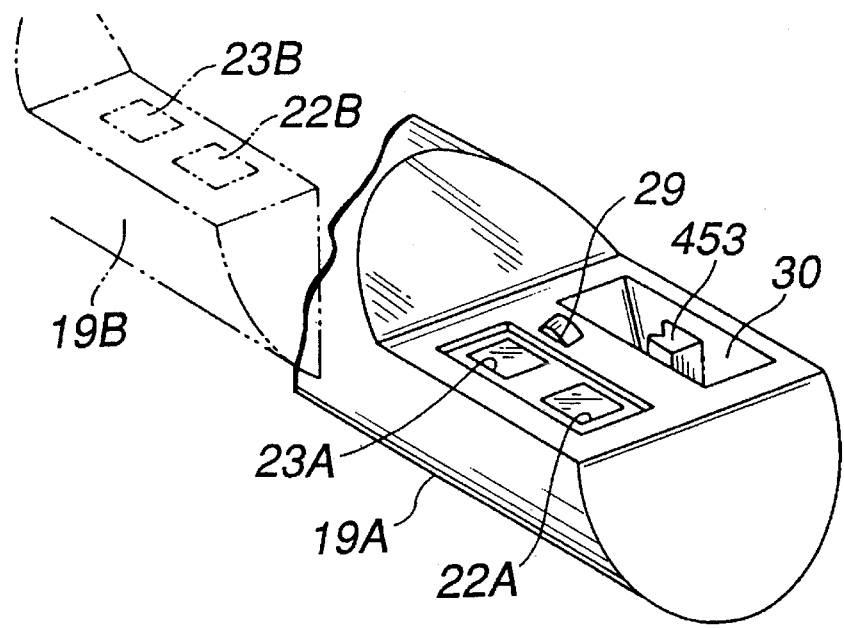

Component members identical to those in the first embodiment will bear the same numerals. The description will be omitted. The coverable endoscope 2B has, as shown in FIG. 55, an illumination window 22B for emitting illumination light and an observation window 23B on the side surface of the distal part 19B thereof. The cover 2B also has, as shown in FIG. 56, a cover illumination window 22A and a cover observation window 23A on the side surface thereof.

Figure 53:
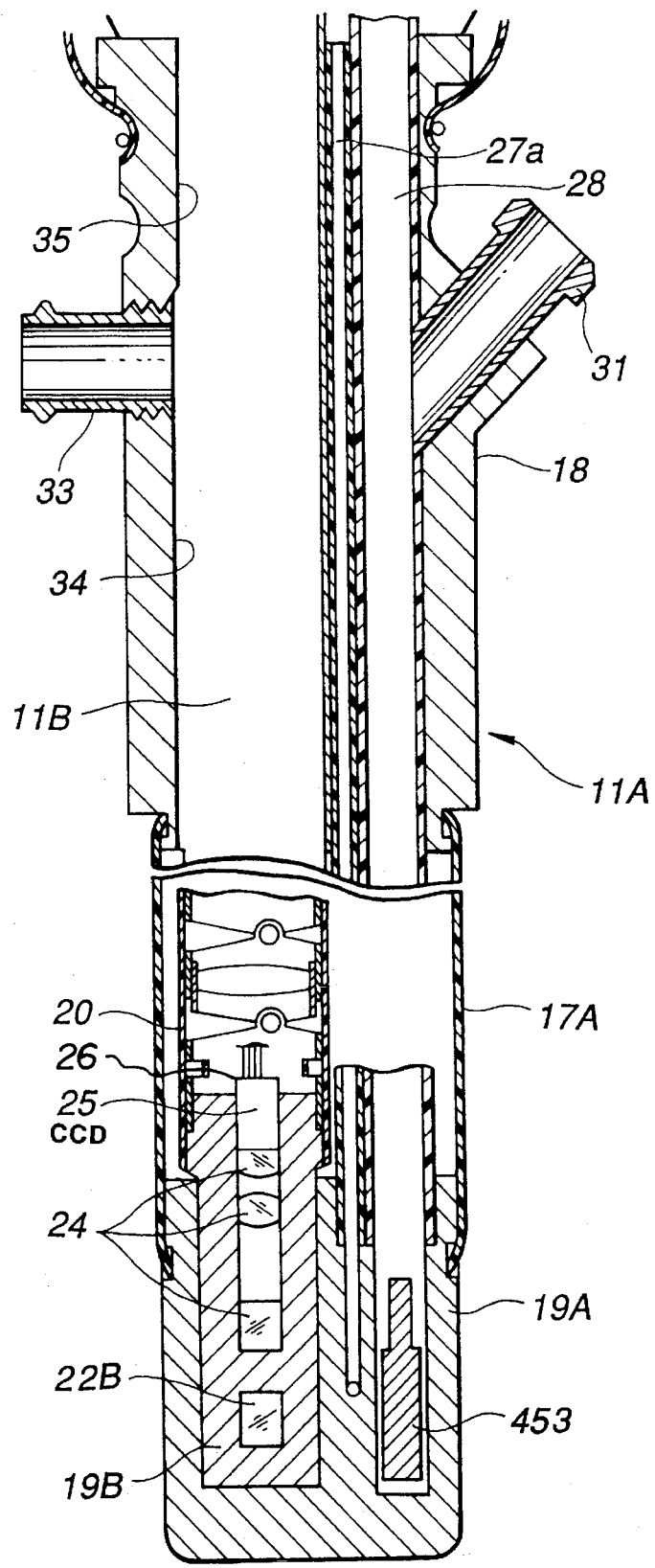
Figure 57:
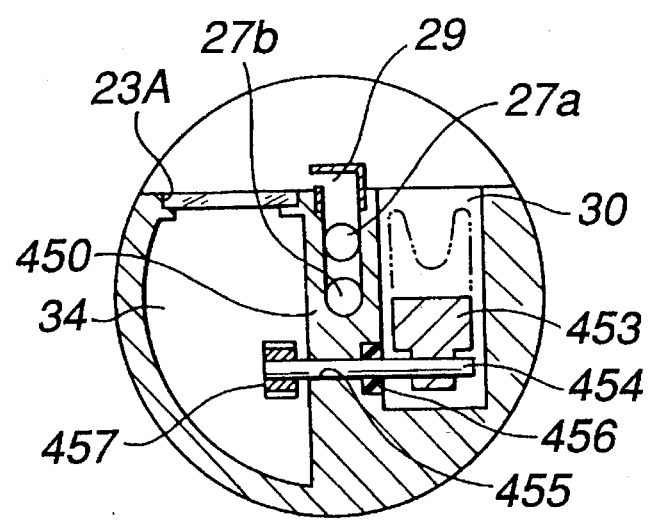

As shown in FIG. 53, an air supply tube, a water supply tube (not shown), and a suction tube are mounted in the insertional part cover 11A, forming an air supply channel 27a, a water supply channel 27b (See FIG. 57), and a suction channel 28. As shown in FIG. 57, the distal ends of the air supply channel 27a and water supply channel 27b communicates with a nozzle 29 in the distal cover part 19A. The distal opening of the nozzle 29 is located on the outer surface of the cover observation window 23A.

Figure 54:
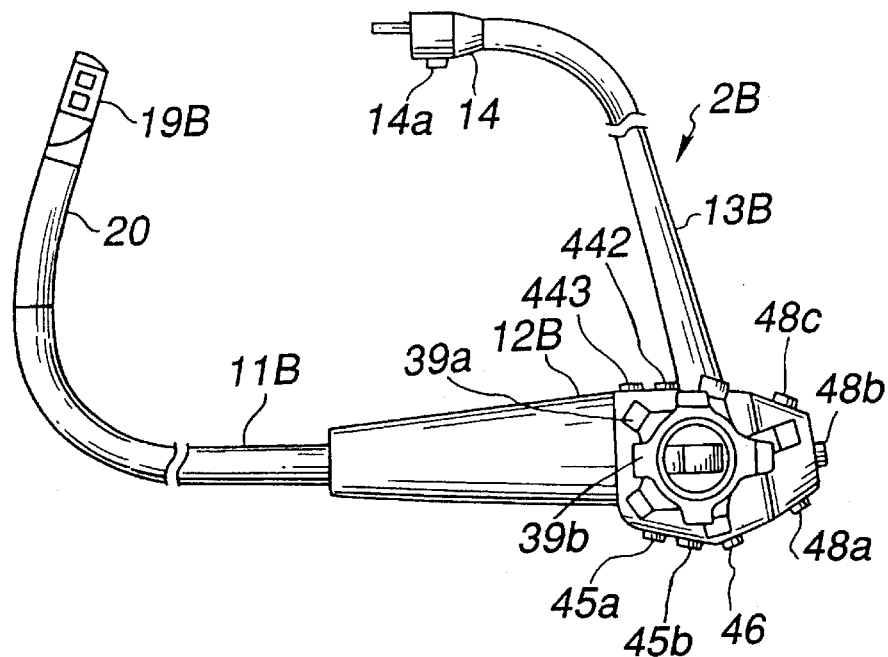

FIG. 54 shows the coverable endoscope 2B. The operational part 12B has angulation knobs 39a and 39b for angling the bending section 20 formed in the distal portion of the insertional part 11B. The bending section 20 can be angled vertically and laterally by operating the angulation knobs 39a and 39b.

The operational part 12B also includes an air switch 45a, a water switch 45b, a suction switch 46, and photographic function switches 48a, 48b and 48c. Air supply, water supply, suction, and photography can be executed by operating the respective switches.

Forceps raise switches 442 and 443 are formed on the opposite side of the air switch 45 and other switches on the operational part 12B. Depending on how the switches 442 and 443 are manipulated, a forceps raise base (hereinafter, raise base) 453 for defining the direction in which forceps are projected can be raised or swiveled in the opposite direction for resolving the raise.

The coverable endoscope 29 is structured to tightly shut out water similarly to that in the first embodiment.

In this embodiment, as described below, the raise base in the cover 2A and a swivel support mechanism by which the raise base 453 is supported so as to be able to swivel freely are coupled with a mechanism mounted in the coverable endoscope 2B for generating a rotation driving force by means of a coupling mechanism that is structured to tightly shut out water. Consequently, the forceps raise angle (angle in the direction in which forceps are projected with respect to the axis of the insertional part 11B) can be varied drastically. The formation of the raise base 453 in the cover 2A offers a structure that even when forceps are raised, the forceps channel is hardly damaged.

As shown in FIG. 56, the raise base 453 is mounted in a forceps outlet 30 formed in an area of the distal cover part 19A adjoining to the one thereof in which the distal part 19B is stored. As shown in FIG. 57, the raise base 453 is fixed to one end of a rotary axis 454 extending in a direction perpendicular to the axis of the insertional part (vertical to the surface of the drawing) by applying, for example, adhesive or solder.

The rotary axis 454 passes through a hole 455 penetrating through a partition 450 that isolates the forceps outlet 30 in the distal cover part 19A from the endoscope insertion channel 34 so as to tightly shut out water. The other end of the rotary axis 454 is projecting into the endoscope insertion channel 34 and engaged with a gear 457.

Water is tightly shut out from the rotary axis 454, which lies through the hole 455 so as to be freely rotatable and supports the raise base 453 so that the raise base 453 can swivel freely, due to a water shutout packing 456 embedded in a recess in the outlet 30. This prevents fluid from leaking out of the hole 455 into the endoscope insertion channel 34.

The recess on the partition 450 in contact with the water shutout packing 456 is entirely sealed with adhesive, so that water will not leak out of the hole 455 into the endoscope insertion channel 34.

An axis 458 (which transmits a rotation driving force) is projecting from the side of the distal part 19B of the coverable endoscope 2B facing the forceps outlet 30. A gear 459 is fixed to the distal end of the axis 458. The other end of the axis 458 is present in the distal part 19B and coupled with an electric motor 460 (See FIG. 58) for generating a driving force for driving the rotation of the raise base 453.

Figure 58:
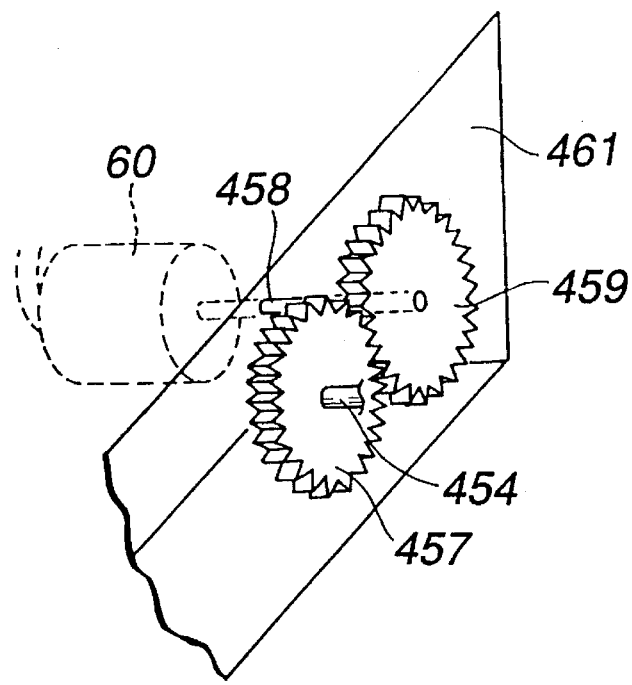

The axis 458 is, as shown in FIG. 58, projecting at a position at which a gear 457 will engage with the gear 459 when the coverable endoscope 2B is inserted into the insertional part cover 11A. The distal part 19B has a ditch 461 for avoiding the interference of the gear 457 with the distal part 19 occurring when the coverable endoscope 2B is inserted into the insertional part cover 11A.

Figure 59:
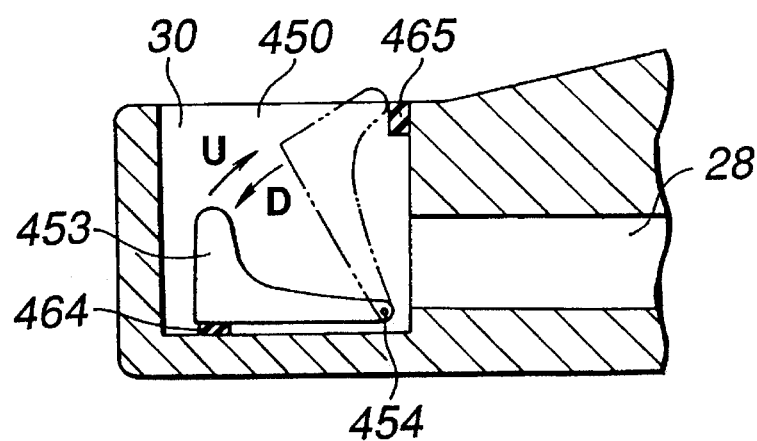

After the coverable endoscope 2B is inserted into the insertional part cover 11A, when an electric motor 460 is rotated, the raise base 453 swivels with the rotation axis 454 as a center as shown in FIG. 59.

Owing to the water shutout packing 456, dirt in the forceps outlet 30 will not invade into the endoscope insertion channel 34. The endoscope insertion channel 34 will not be contaminated.

Depending on how the forceps raise switches 443 and 443, which are shown in FIG. 54, formed on the operational part 12B are manipulated, the orientation of current applied from a drive circuit to the electric motor 460 varies and the direction of rotation differs (which will be described later).

The rotating force is transmitted to the gear 459 and gear 457 engaging with the gear 459 via the axis 458. The gears 459 and 457 then rotate. The rotating force passes through the axis 454 having the gear 457 and serves as a driving force for swiveling the raise base 453 (in the outlet 30) in the up direction (indicated with an arrow U in FIG. 59) or Down direction (indicated with an arrow D in FIG. 59).

Figure 60:
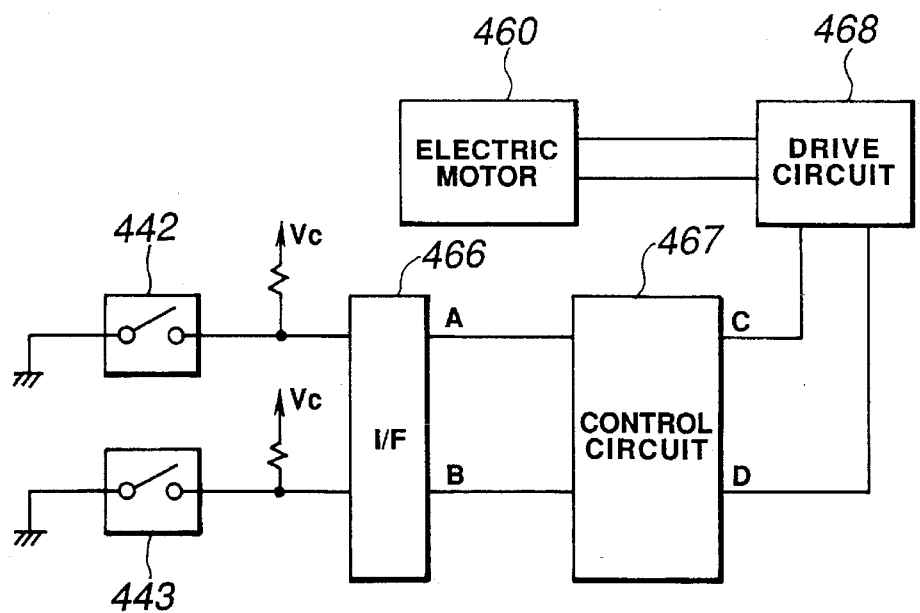

Stoppers 464 and 465 are mounted in the forceps outlet 30 as shown in FIG. 59. The raise base 453 abuts on the stoppers 464 and 465, and thus has its rotation angle restricted. The control sequence of the electric motor 460 will be described in conjunction with FIGS. 60 and 61.

The forceps raise switches 442 and 443 formed on the operational part 12B are connected to an interface 466. The interface 466 is connected to a control circuit 467. The control circuit 467 is connected to a drive circuit 468. The electric motor 460 is connected to the drive circuit 468.

Figure 61:
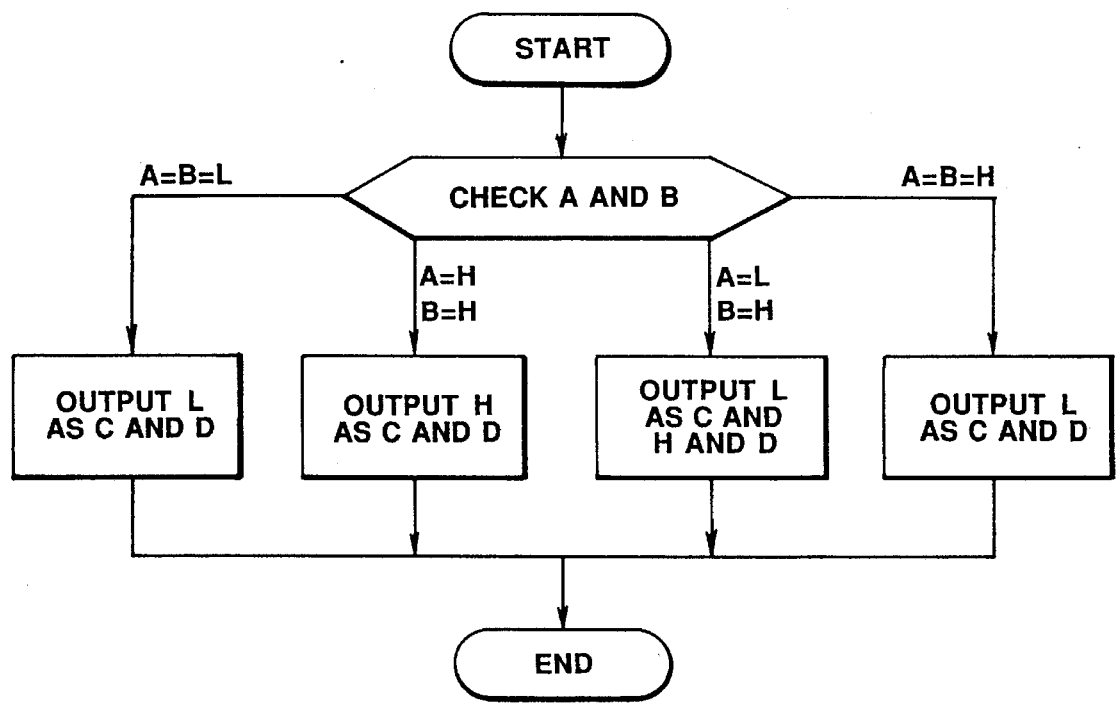

The interface 466 provides two outputs A and B which vary depending on how the switches 442 and 443 are manipulated. The outputs A and B assume high or low levels. Depending on the levels of A and B, the control circuit 467 provides, as shown in FIG. 61, low or high-level outputs via terminals C and D thereof. At this time, the output of C is a signal defining the direction of rotation; that is, rotation or reversion, while the output of D is a signal defining an on or off state.

The drive circuit 468 drives the motor 460 in such a manner that:

when the outputs C and D are high, the motor 460 will rotate in the Up direction;

when the output C is low and the output D is high, the motor 460 will rotate in the Down direction; and when the outputs C and D are low, the motor 460 will stop.

The direction of rotation is changed by, for example, varying the orientation of driving current supplied from the drive circuit 468 to the motor 460. The motor 460 is stopped by cutting off the driving current for the motor 460.

In the aforesaid embodiment, the motor 460 for raising forceps is stored in the coverable endoscope 2B. The rotation driving force supplied by the motor 460 is transmitted to the raise base 453 in the cover 2A via the axis 454 that penetrates through the partition 450 which isolates the endoscope insertion channel 34 from the forceps outlet 30 so as to tightly shut out water, and that can rotate freely.

When the covered endoscope of this embodiment is used for endoscopic examination, the raise 453 raises forceps. A forceps raiser thus realized provides a sufficient forceps raise angle and is less likely to damage the forceps channel during forceps raise.

When the covered endoscope of this embodiment is used for endoscopic examination, even if dirt adheres to the raise base 453, since the raise base 453 is disposed of together with the cover 2A, the coverable endoscope 2 which is isolated to tightly shut out water will be unaffected by contamination.

When the coverable endoscope 2B is to be cleaned, since the forceps raise mechanism does not include the raise base 453 to which dirt is likely to adhere, cleaning can be done easily. The coverable endoscope 2B can thus be kept clean effortlessly.

Figure 62:
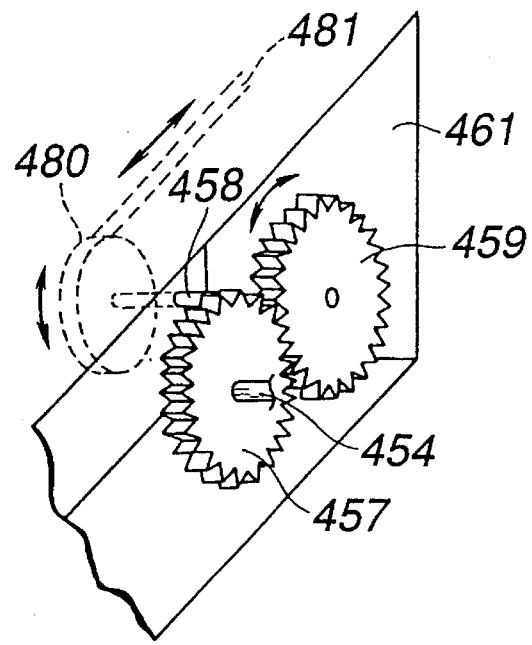
FIG. 62 is an oblique view showing a major portion of a variant of the sixth embodiment.

FIG. 62 shows a major portion of a variant of the sixth embodiment of the present invention.

The variant differs from the sixth embodiment only in a driving means for swiveling the raise base 453. Component members identical to those in the sixth embodiment will bear the same numerals. The description will be omitted.

As shown in FIG. 62, a pulley 480 is fixed instead of the motor 460 to the proximal end of the axis 458 that is extending from the inside of the distal part 19B and has the gear 459 fixed to the distal end thereof.

A forceps raise wire 481 is fixed at a position deviated radially from the center of the pulley 480. The forceps raise wire 481 is routed through the insertional part 11B and linked with a forceps raising means installed in the operational part which is not shown. When the raising means is rotated, the forceps raise wire 481 advances or withdraws along the axis of the distal part 19. The forceps raising means is realized with, for example, the same structure as the angulation mechanism shown in FIG. 35. The mechanism in FIG. 35 is designed for up, down, right, and left bending. Since forceps raising is concerned with up and down movement, only the angulation mechanism relating to either up and down bending or right and left bending is necessary.

When the forceps raising means is manipulated to advance or withdraw the forceps raise wire 481, the pulley 480 rotates. The gear 459 then rotates via the axis 458 (in an arrow direction in FIG. 62). Consequently, the raise base 453 swivels with the rotation axis 454 as a center as shown in FIG. 59.

The advantages of this embodiment are substantially the same as those of the sixth embodiment.

Referring to FIGS. 63 to 67, the seventh embodiment of the present invention will be described.

This embodiment partly differs from the sixth embodiment in the shapes of a cover and a coverable endoscope. Components identical to those of the sixth embodiment will bear the same numerals. The description will be omitted.

Figure 63:
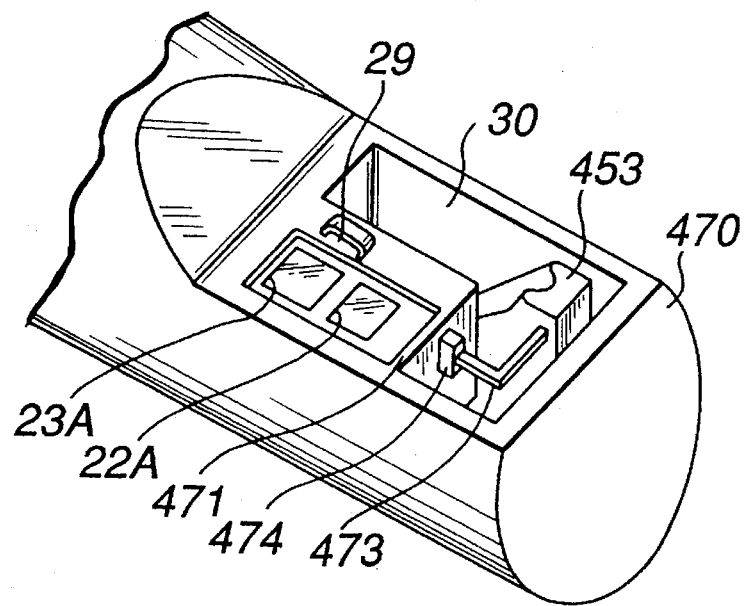
FIGS. 63 to 66 relate to the seventh embodiment of the present invention.

FIG. 63 shows a distal cover part 470 of the cover 2A in this embodiment.

In the distal cover part 470, as shown in FIG. 63, the forceps outlet 30 is extending toward the distal end beyond the distal end of the endoscope insertion channel 34. The distal (terminal) surface of the endoscope insertion channel 34 is isolated from the forceps outlet 30 via a partition 471 that is made of a thin stretchable high polymer material; such as, urethane and that is characteristic of tightly shutting out water.

Figure 64:
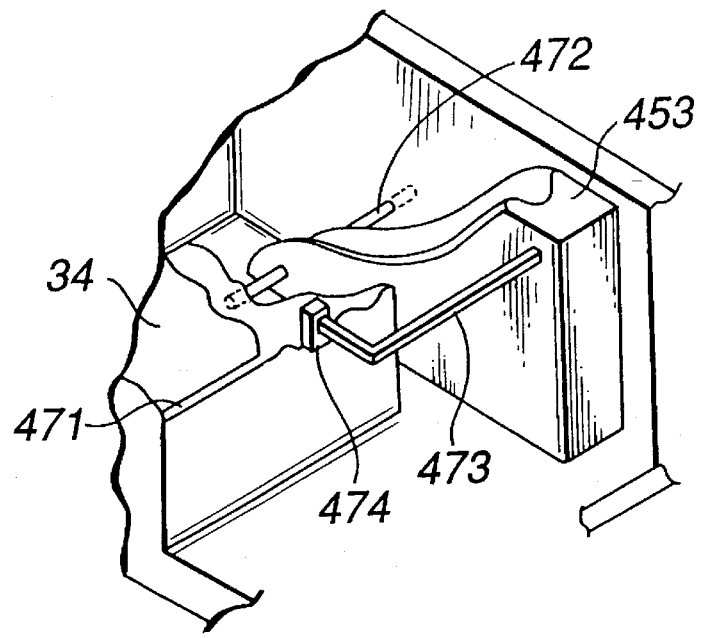

As apparent from the enlarged view of FIG. 64, the raise base 453 is mounted in the distal cover part 470 so as to be able to swivel freely with respect to a rotation axis 472. In addition, a raise base operating member 473 is attached to the raise base 453 so as to be freely rotatable by performing, for example, caulking. A magnet 474 is fixed to the distal end of the raise base operating member 473. The magnet 474 is usually located in the vicinity of the partition 471.

Figure 65:
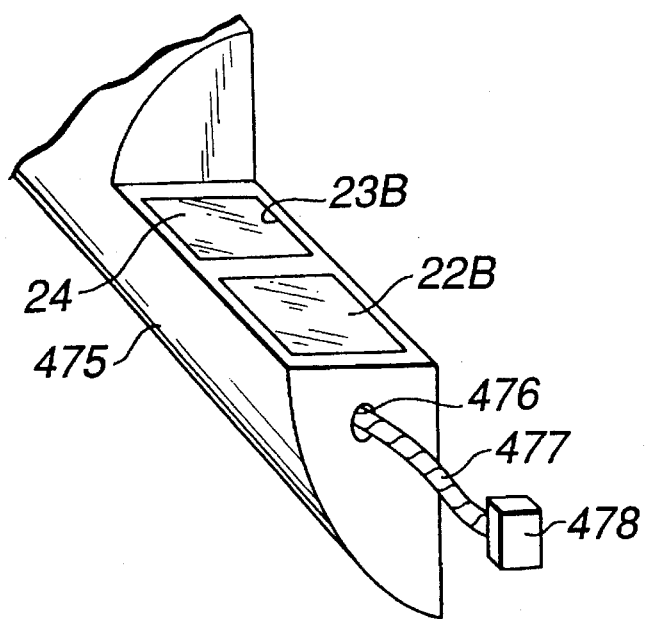

FIG. 65 shows a distal part 475 of the coverable endoscope 2B.

The distal part 475 has a hole 476 through which a forceps raise wire 477 is extending. The forceps raise wire 477 passes through an insertional part, and is connected to a forceps raising means made up of a forceps raise knob and a forceps raise link formed on an operational part. When the raising means is manipulated, the forceps raise wire 477 advances or withdraws along the axis of the distal part 475. A magnet 478 is fixed to the distal end of the wire 477. The polarity of the magnet 478 is reverse to that of the magnet 474 fixed to the distal end of the raise base operating member 473 (for example, if 474 is the South, 478 is the North).

When the distal part 475 of the coverable endoscope 2B having the foregoing structure is inserted into the aforesaid distal cover part 470, the forceps raise wire 474 is coupled with the raise base operating member 473 due to the mutual attraction between the magnets 478 and 474 which are placed in the distal part of the coverable endoscope and in the distal cover part respectively.

Figure 66:
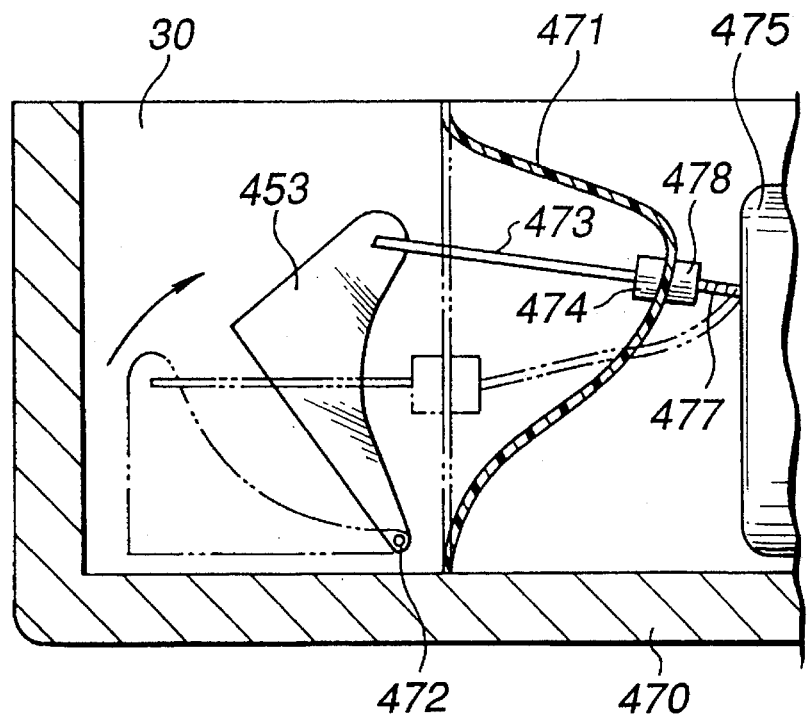

When the forceps raising means formed on the operating part is manipulated to advance or withdraw the forceps raise wire 477, the raise base 453 swivels with the rotation axis 472 as a center as shown in FIG. 66.

In this case, the partition 471 is made of a thin stretchable high polymer material of, for example, 0.1 to 2 mm thick. Even when the wire 477 is advanced or withdrawn, the partition 471 will not be torn out. Dirt will therefore not flow into the endoscope insertion channel 34 through the forceps outlet 30. The endoscope insertion channel 34 will not be contaminated. The seventh embodiment has substantially the same advantages as the sixth embodiment.

Figure 67:
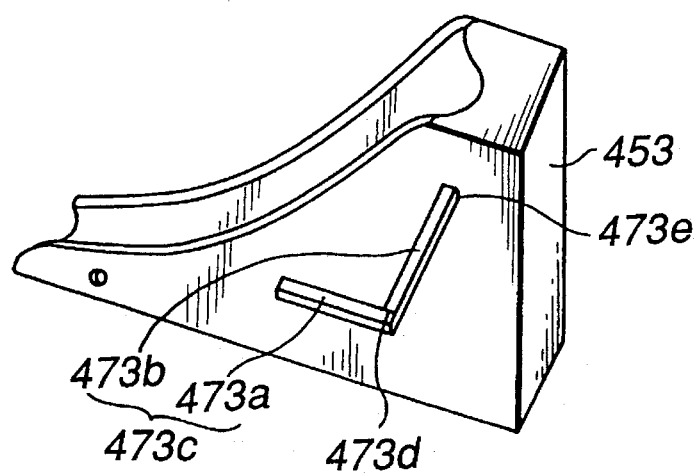
FIG. 67 is an oblique view showing a forceps base operating member in a variant of the seventh embodiment.

In the above description, the raise base operating member 473 is realized with a single part. In FIG. 67, an operation member 473c is made of two parts: a bar-like first member 473a and a second member 473b. If either a joint 473d between the first member 473a and second member 473b or a joint 473e between the operating member 473b and raise base 453 is fixed so as to be freely rotatable, the other portions may be immobilized by applying, for example, adhesive or solder. Both the joints 473d and 473e may be fixed so as to be freely rotatable.

In the above description, two members are used to realize a means for coupling the coverable endoscope 2B with the cover 2A so as to transmit a driving force for raising the raise base 453 via the partition 471, which are the magnets 474 and 478 whose polarities are reverse to each other. One of the members may be a magnet, and the other one may be made of a material attracted by a magnetic force; such as, iron. This variant will also have the same operation and advantages.

Next, the eighth embodiment of the present invention will be described with reference to FIGS. 68 to 72.

This embodiment differs from the seventh embodiment only in a method of coupling the raise base operating member 473 with the forceps raise wire 477. Components identical to those in the seventh embodiment will bear the same numerals. The description will be omitted.

Figure 68:
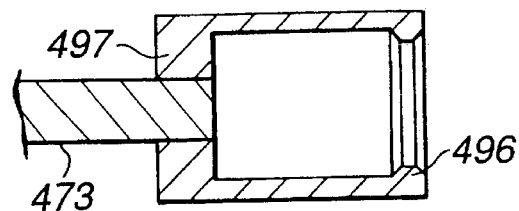
FIG. 68 is a cross-sectional view showing a distal part of a forceps base operating member in the eighth embodiment of the present invention.
Figure 69:
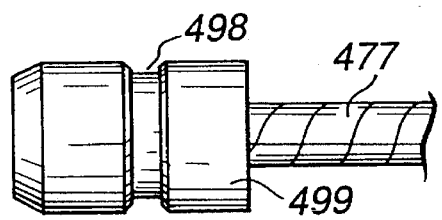
FIG. 69 is a side view showing a distal part of a forceps raise wire.
Figure 70:
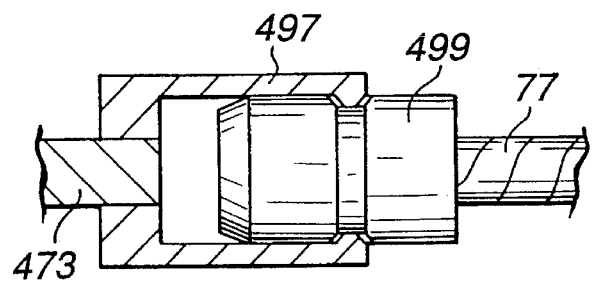
FIG. 70 is a cross-sectional view showing a state that a distal part of a forceps base operating member is coupled with a distal part of a forceps raise wire.

FIG. 68 shows the distal portion of the raise base operating member 473. The distal portion has a projection 496 on the inner surface thereof. A cylindrical coupling member 497 having elasticity is fixed to the distal portion by applying adhesive or other means. FIG. 69 shows the distal portion of the forceps raise wire 477.

The distal portion of the forceps raise wire 477 has a ditch 498 in which the projection 496 formed on the inner surface of the coupling member 497 is embedded. A cylindrical coupling member 499 is fixed to the outer circumference of the ditch 498 by applying adhesive, solder, or other means.

The coupling members 497 and 499 have the aforesaid structures. Thanks to the elasticity of the coupling member 497, the coupling member 499 can be mated with the coupling member 497 so as to be freely detachable.

Figure 71:
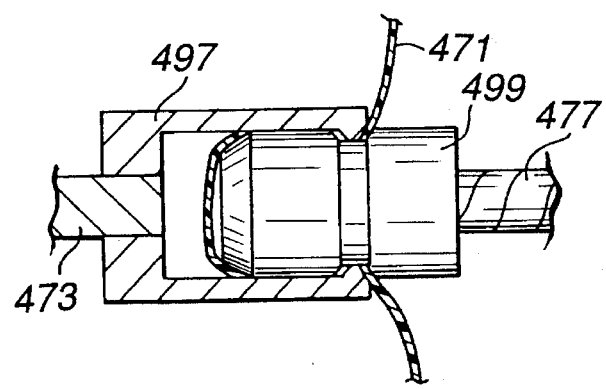
FIG. 71 is a cross-sectional view showing a state that a distal part of a forceps base operating member is coupled with a distal part of a forceps raise wire with a partition between them.

The partition 471 formed in the distal cover part is thin and elastic. Therefore, as shown in FIG. 71, the coupling members 497 and 499 can be mated with each other with the partition 471 between them and are still detachable. The coupling member 497 formed in a disposable cover, which is usable for each patient, may be destroyed when decoupled from the coupling member 499.

Using the coupling members 497 and 499 having the aforesaid structures, the raise base operating member 473 and forceps raise wire 477 are coupled with each other.

This embodiment have the same operation and advantages as the seventh embodiment.

Figure 72:
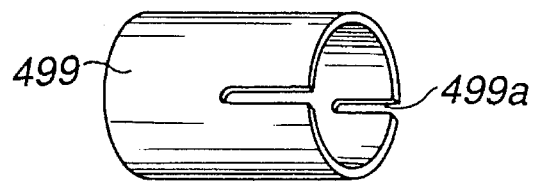
FIG. 72 is an oblique view showing a coupling member with slits.

When at least one slit 499a as that shown in FIG. 72 is formed on the coupling member 499 attached to the distal end of the raise base operating member, the coupling member 499 can deform more easily. The detachability improves.

Figure 73:
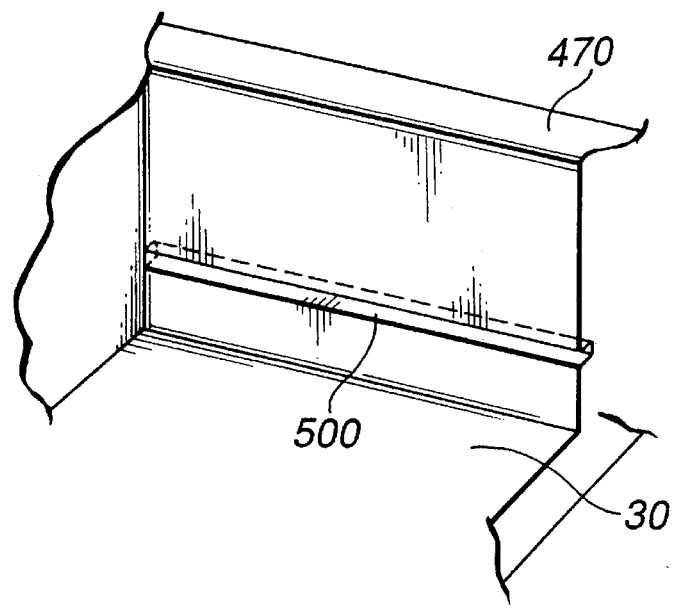
FIG. 73 is an oblique view showing a distal cover part with a guide ditch.
Figure 74:
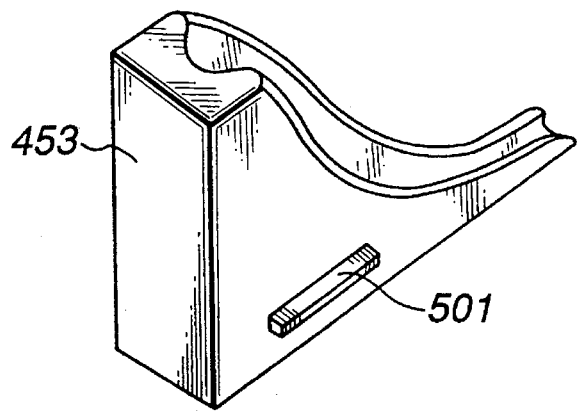
FIG. 74 is an oblique view showing a forceps base with a projection formed.
Figure 75:
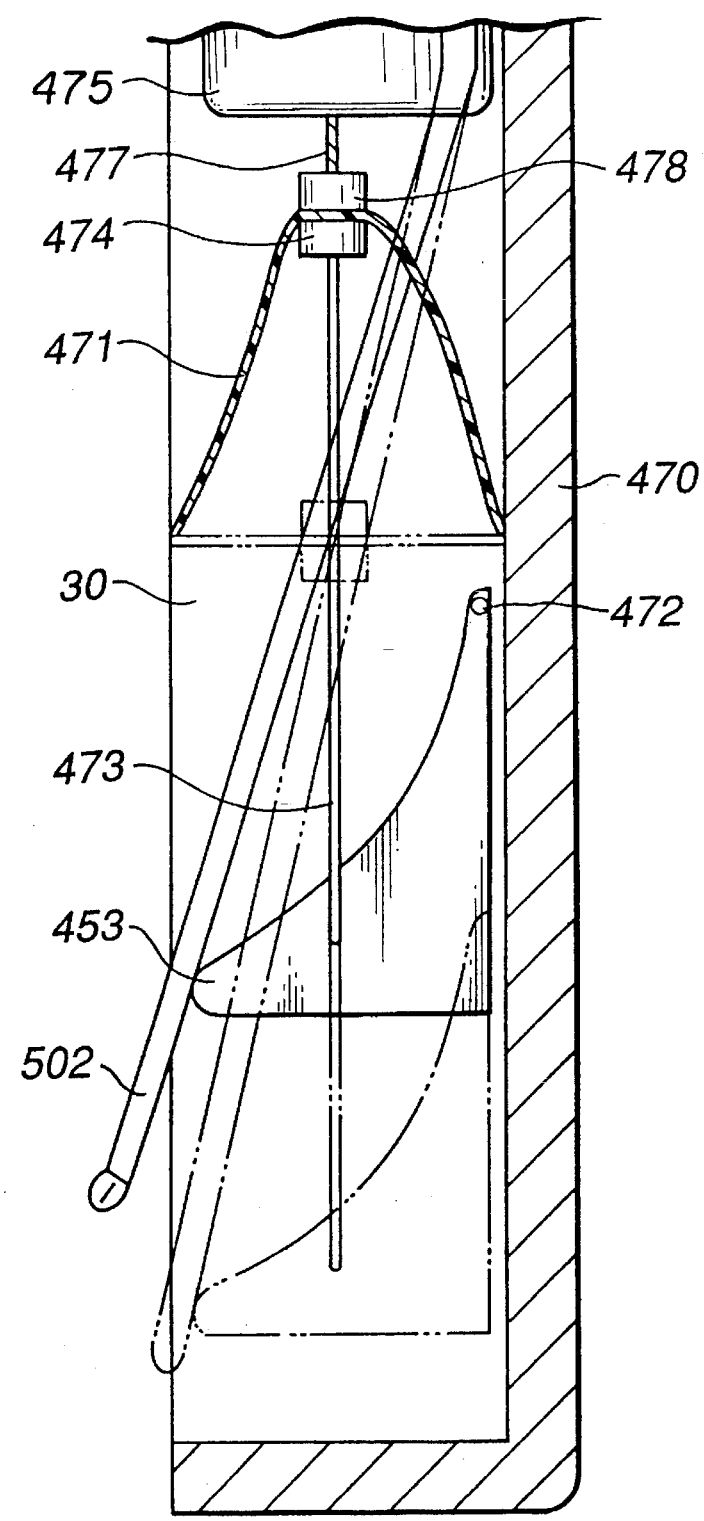
FIG. 75 is an explanatory diagram explaining that a forceps base can be raised by advancing or withdrawing a forceps raise wire.

The raise base 453 may be structured as shown in FIGS. 73 to 75 for easy mounting in the cover 2A.

As shown in FIG. 73, a guide ditch 500 is formed on the inner wall of a distal cover part 470 along the axis of the insertional part cover 11A. As shown in FIG. 74, on the raise base 453, a projection 501 to be embedded in the guide ditch 500 is formed at a specified position on the raise base 453 at which when the raise base 453 is mounted, the projection 501 will coincide with the guide ditch 500. When the raise base 453 is mounted in the forceps outlet 30 using the elasticity of the insertional part cover 11A, the raise base 453 can move over the guide ditch 500 smoothly along the axis of the insertional part cover 11A.

When the raise base operating member 473 attached to the raise base 453 and the forceps raise wire 477 coupled with the raise base operating member 473 are advanced or withdrawn along the axis of the insertional part cover 11A by manipulating the forceps raising means formed on the operational part, the raise base 453 advances or withdraws. This advancement and withdrawal makes it possible to freely vary the raise angle of a treatment adaptor (or forceps) 502 projecting from the forceps outlet 30 as shown in FIG. 75 with respect to the axis of the insertional part cover 11A.

In the variant of the seventh embodiment and in the eighth embodiment, the raise base operating member is coupled with the forceps raise wire via the coupling member, and the operating means coupled with the forceps raise wire is manipulated. An alternative method will be described below.

A rod is coupled with the raise base operating member via the coupling member. The rod is connected to an electric motor mounted in the coverable endoscope and structured to advance or withdraw along the axis of the insertional part cover depending on how the control switches, which are not shown, formed on the operational part are manipulated. The electric motor is controlled by the control unit, which is not shown, so that the electric motor will rotate within the functionally-required quantity of movement of the raise base depending on how the switches are manipulated.

In endoscopic examination, a tube is inserted along an endoscope channel into, for example, the bile duct, and then contrast medium is injected through the tube into the bile duct. Alternatively, a tube is inserted along the endoscope channel into a body cavity, and then a dye such as methylene blue is dispersed into the body cavity. This kind of examination can be conducted even using an endoscope cover-sheathed endoscope.

For the above examination, a fluid supply tube employed must be disinfected and sterilized thoroughly in order to prevent infection.

In efforts to provide an endoscope cover-sheathed endoscope permitting use of a clean fluid supply tube all the time, a cover of the present invention is structured as described below.

Figure 76:
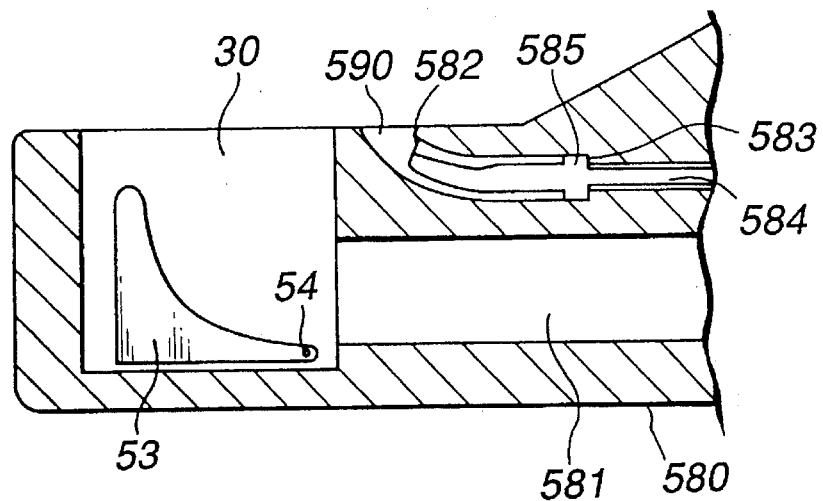
FIG. 76 is a cross-sectional view showing an insertional part cover with a fluid supply tube channel mounted.

An insertional part cover 580 shown in FIG. 76 has a forceps channel 581 and a fluid supply tube insertion channel 582.

The fluid supply tube insertion channel 582 has a step 583 to provide a large-diameter distal portion.

A sterilized fluid supply tube 584 running through the channel 582 includes a flange 585 abutting on the step 583.

Figure 77:
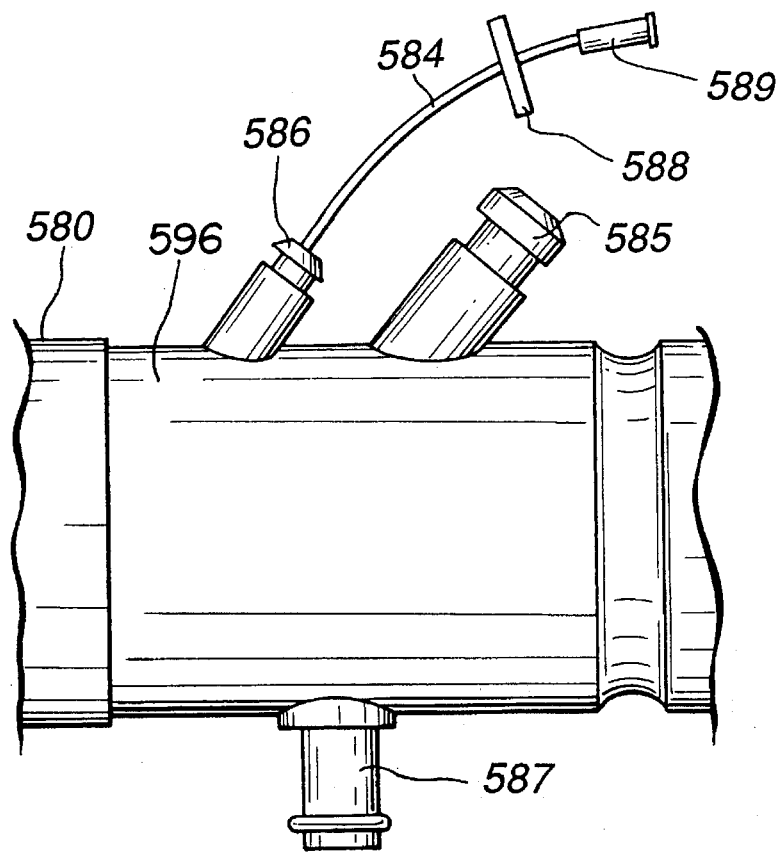
FIG. 77 is a side view showing the configuration of the proximal portion of FIG. 76.

As shown in FIG. 77, the proximal portion of the insertional part cover 580 includes an operational part locking cap 596. The locking cap 596 has a forceps insertion port 585, a fluid supply tube insertion port 586, and a dilation tube cap 587.

The proximal portion of the fluid supply tube 584 includes a flange having a larger diameter than the fluid supply tube insertion port 586, and a fluid injection cap 589.

The flange 588 is distanced from the fluid supply tube insertion port 586. The distance is longer than a length of advancing or withdrawing the fluid supply tube (at least 30 mm).

The fluid supply tube 584 is inserted through a fluid tube outlet 590 formed in the distal portion of the insertional part cover 580. Thereafter, the flange 588 and fluid injection cap 589 are attached to the proximal portion of the fluid supply tube 584 using adhesive or the like. FIG. 77 shows the assembled state.

The aforesaid structure enables the fluid supply tube 584 to advance or withdraw a distance necessary for examination. After assembled, the flanges 585 and 588 attached to the fluid supply tube abut on the step 583 and fluid supply tube insertion port 586 respectively. Since the movement of the fluid supply tube is thus restricted, the fluid supply tube will not come off from the fluid supply tube insertion channel 582.

The fluid supply tube 584 is disposable or usable for each patient similarly to the insertional part cover 580, which will therefore not be contaminated. This means that the fluid supply tube 584 employed is always clean.

In the above description, the flange 588 is provided to abut on the fluid supply tube insertion port 586 and restrict the movement of the fluid supply tube. If the fluid injection cap 589 is structured to abut on the fluid supply tube insertion port 586 and restrict the movement of the fluid supply tube, the flange 588 becomes unnecessary. This variant has the same operation and advantages.

Figure 78:
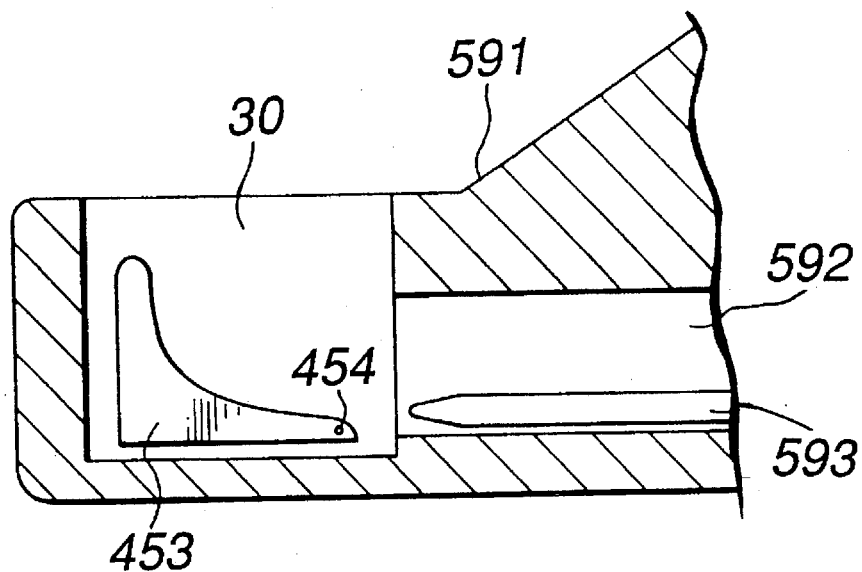
FIG. 78 is a cross-sectional view showing an insertional part cover with a fluid supply tube lying through a forceps channel thereof.

If a sterilized fluid supply tube 593 is mounted in a forceps channel 592 in an insertional part cover 591 as shown in FIG. 78, the fluid supply tube 593 becomes disposable for each patient similarly to the insertional part cover 591. This provides the same advantages as those described above. Furthermore, since a flange need not be attached to the fluid supply tube 593, production becomes simpler. Eventually, the prime cost decreases.

Figure 79:
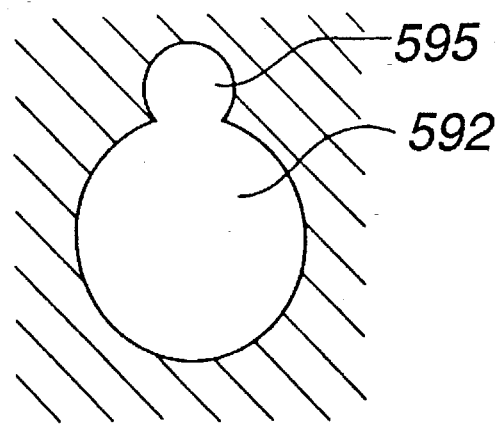
FIG. 79 is a cross-sectional view of the forceps channel of FIG. 78.

When the forceps channel 592 is shaped to have a cross section shown in FIG. 79, if the fluid supply tube 593 is embedded in a small-diameter section 595 whose diameter is substantially the same as the outer diameter of the fluid supply tube 593, the fluid supply tube 593 can be advanced or withdrawn smoothly. The advancement or withdrawal will not interfere with the insertion of other forceps.

Figure 80A:
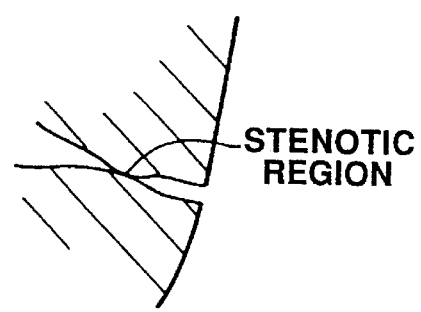
FIGS. 80a and 80b are explanatory diagrams showing a stenotic region and a guide tube placed in the stenotic region.
Figure 80B:
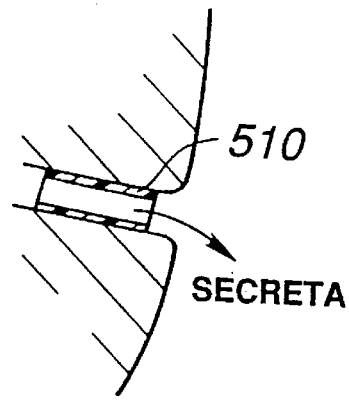
Figure 82:
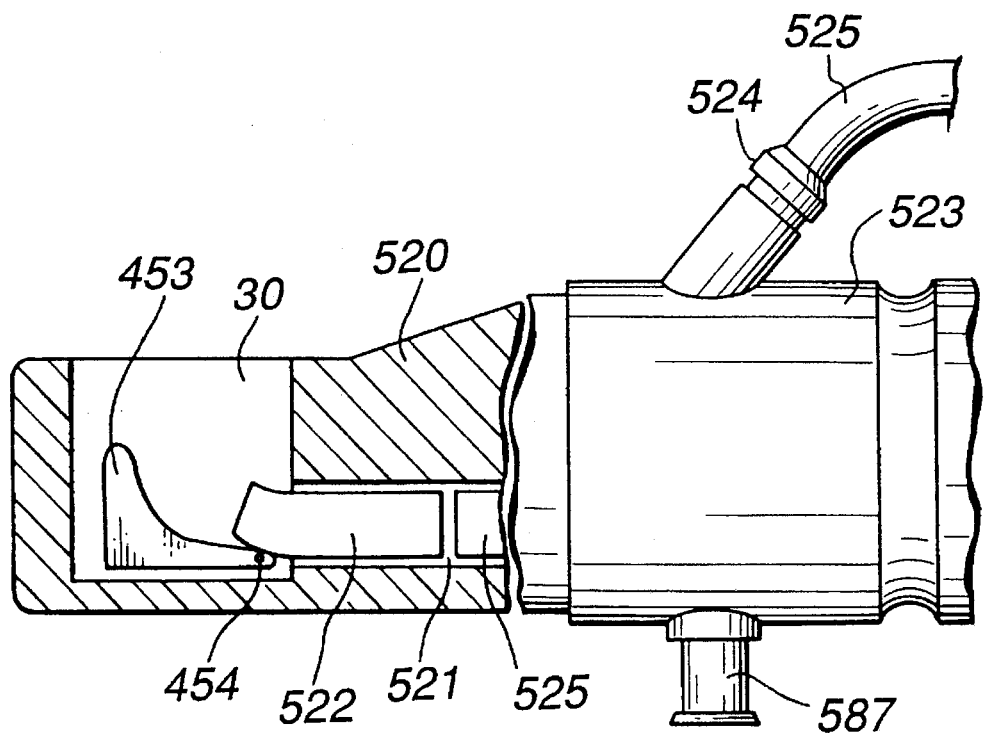
FIG. 82 is an explanatory diagram explaining an operation of implanting a guide tube using a pusher tube.

Treatment using an endoscope has been widely adopted in recent years. One of therapeutic procedures is that an endoscope channel is routed into a stenotic lumen (for example, the bile duct), a guide tube 510 of several ten millimeters long is inserted to canalize the stenotic region, and then secreta accumulated in the lumen is drained (FIGS. 80a and 80b). This procedure is adopted even in treatment using an endoscope cover-sheathed endoscope.

Figure 81A:
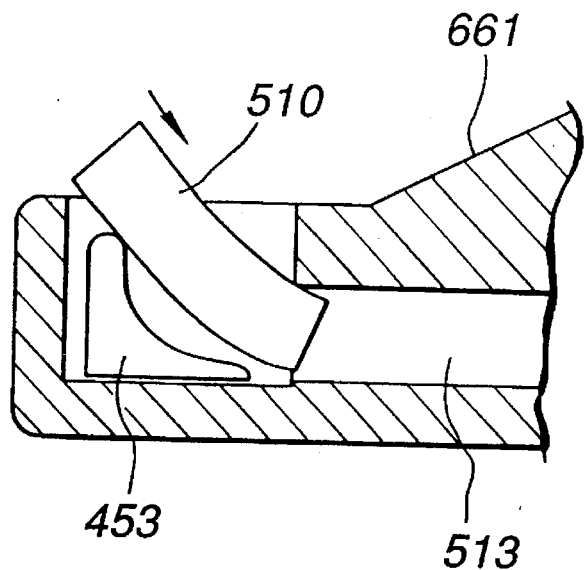
FIGS. 81a and 81b are explanatory diagrams explaining an operation of implanting a guide tube.
Figure 81B:
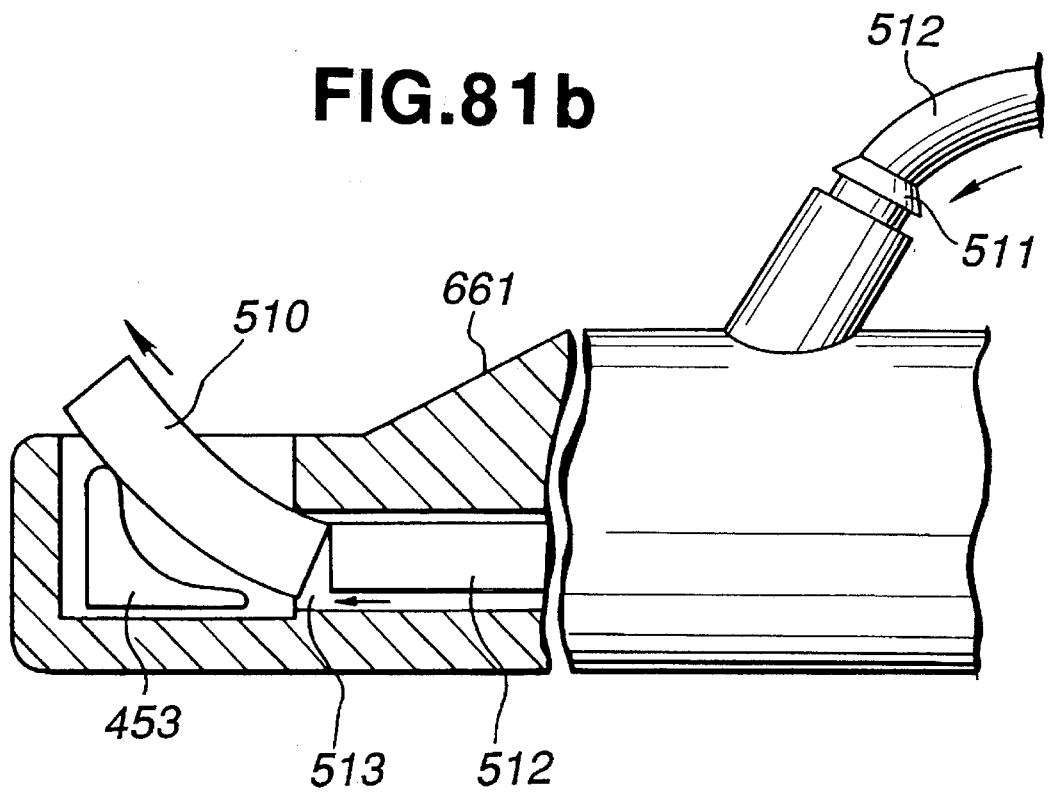

When the above procedure is adopted, as shown in FIG. 81a, before an endoscope is inserted into a body cavity, the guide tube 510 is inserted into the forceps channel 513 through, for example, the forceps outlet 30 that is formed in the distal portion of an endoscope and in which the raise base 453 is mounted. When the endoscope reaches an intended region, as shown in FIG. 81b, the guide tube 510 is pushed out using a pusher tube 512 which has been inserted into the forceps channel 513 through the forceps insertion port 511 formed in the proximal portion of the endoscope. In FIG. 81b, 661 denotes an insertional part cover.

In the aforesaid procedure, sterilized gloves are used to insert the guide tube into the forceps channel, thus preventing infection. It takes much time to make the preparations.

Figure 83:
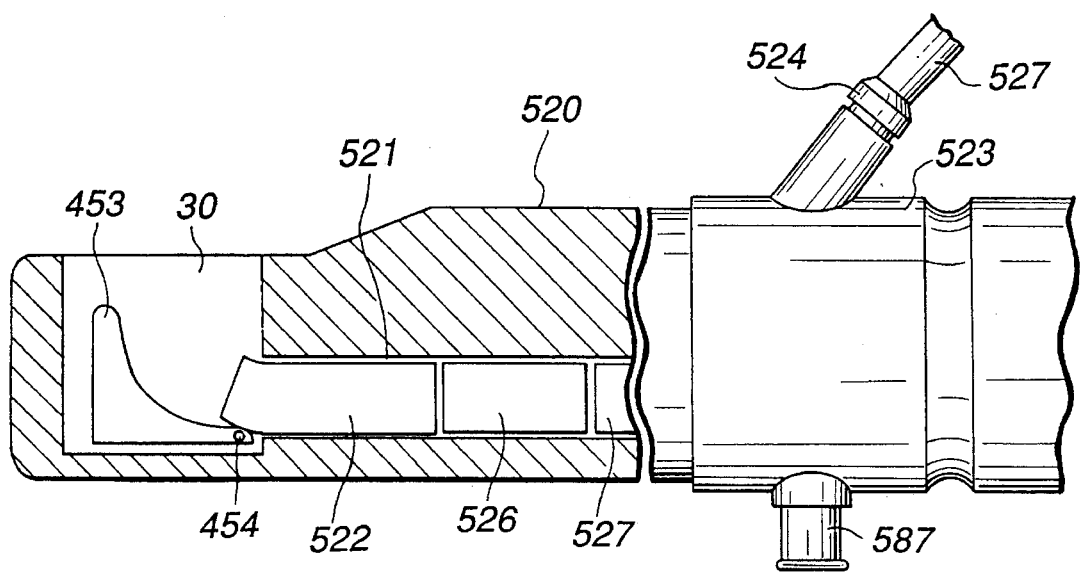
FIG. 83 is an explanatory diagram explaining an operation of implanting a guide tube using a sterilized tube.

The following structure is conceivable in attempts to achieve an object of providing an endoscope cover-sheathed endoscope realizing simple preparation and permitting use of a clean guide tube all the time:

A sterilized guide tube 522 is placed, as shown in FIG. 83, at the distal end of a forceps channel 521 mounted in an insertional part cover 520. A sterilized pusher tube 526 is lying in the proximal portion of the forceps channel 521 beyond the guide tube 522 and emerging from the insertional part cover 520 through a forceps insertion port 524 formed in an operational part locking cap 523. This structure enables use of a clean guide tube all the time. Pre-treatment preparations can be made easily without sterilized gloves.

The sterilized guide tube 522 may be embedded in the distal portion of the forceps channel 521, and a sterilized tube 526 may be placed at the proximal end of the guide tube 522. In this structure, even when a dirty pusher tube 527 is used to push out the guide tube 522 into a patient's body cavity, since the guide tube 522 will not touch the dirt, the guide tube 522 can be kept clean all the time. Pre-treatment preparations can be made easily without sterilized gloves.

The aforesaid embodiments are concerned with a covered endoscope that is an electronic endoscope. The present invention can apply to an optical coverable endoscope (namely, a coverable fiberscope) in which an image guide may be used instead of an imaging device and an eyepiece is employed for observation.

An endoscope used in conjunction with the aforesaid cover is not limited to a coverable endoscope but may be an endoscope designed to be used without a cover; that is, with bare body. The aforesaid embodiments may be combined partly to form different embodiments which also belong to the present invention.

What is claimed is:

1. An endoscope cover-sheathed endoscope comprising:

an endoscope cover; and an endoscope-cover coverable endoscope that is to be sheathed with said endoscope cover having an elongated insertional part, wherein said endoscope-cover coverable endoscope is structured to tightly shut out water, and wherein an outer surface of said endoscope-cover coverable endoscope includes a chemical-proof material; and a water shutout checking means for checking if water is tightly shut out of said endoscope-cover coverable endoscope wherein said water shutout checking means includes a water leakage sensor base.

2. An endoscope cover-sheathed endoscope, comprising:

an endoscope cover including a forceps channel into which forceps are insertable and a raise mechanism serving as a guide for changing the direction in which the terminal of said forceps is projected through an opening at the terminal of said forceps channel; and an endoscope-cover coverable endoscope adaptable to be sheathed with said endoscope cover, including an insertional part and a structure for tightly shutting out water, wherein an outer surface of said endoscope-cover coverable endoscope is coated with a chemical-proof material.

3. An endoscope cover-sheathed endoscope according to claim 2, wherein said endoscope-cover coverable endoscope has a direction operating means for changing the direction in which the terminal of said forceps is projected.

4. An endoscope cover-sheathed endoscope according to claim 3, wherein said endoscope-cover coverable endoscope has a driving force generating mechanism that generates a driving force for raising said raise mechanism depending on how said direction operating means is manipulated, and said driving force generating means moves said raise mechanism by rotating or translating it using a driving force transmission mechanism for transmitting a driving force.

5. An endoscope cover-sheathed endoscope according to claim 4, further comprising a partition for isolating said endoscope cover from said endoscope-cover coverable endoscope so as to tightly shut out water; said driving force transmission mechanism coupling said driving force generating mechanism with said raise base via said partition, while retaining a capacity for shutting out water tightly.

6. A channeled endoscope cover-sheathed endoscope, comprising:

an endoscope having an elongated insertional part;

a channeled endoscope cover having an endoscope channel into which said insertional part of said endoscope is inserted, a forceps channel into which forceps are inserted, and a raise mechanism that is embedded in an opening at the terminal of said forceps channel and changes the direction in which said forceps are projected;

a forceps raising means formed on said endoscope and used for raising said forceps;

a driving force generating mechanism that is mounted in said endoscope and generates a driving force depending on how said forceps raising means is manipulated;

a first driving force transmission member mounted in said endoscope and driven by said driving force generating mechanism;

a second driving force transmission member that is mounted in said channeled endoscope cover and with which said raise mechanism embedded in said opening is coupled so as to be freely movable; and a coupling means that couples said first driving force transmission member with said second driving force transmission member via a partition, which is formed between said opening and said endoscope channel, so as to tightly shut out water, while retaining a capacity for tightly shutting out water.

7. An endoscope cover-sheathed endoscope according to claim 6, wherein said coupling means is united with said second driving force transmission member.

8. An endoscope cover-sheathed endoscope according to claim 6, wherein said forceps raising means includes switches for actuating said driving force generating means.

9. An endoscope cover-sheathed endoscope according to claim 6, wherein said driving force generating mechanism includes a motor.

10. An endoscope cover-sheathed endoscope according to claim 6, wherein said forceps raising means also has a capability of said driving force generating mechanism.

11. A channeled endoscope cover-sheathed endoscope, comprising:

an endoscope having an elongated insertional part;

a channeled endoscope cover having an endoscope channel into which said insertional part of said endoscope is inserted, a forceps channel into which forceps are inserted, and a raise mechanism that is embedded in an opening at the terminal of said forceps channel and changes the direction in which said forceps are projected;

a forceps raising means formed on said endoscope and used for raising said forceps;

a driving force generating mechanism that is mounted in said endoscope and generates a driving force depending on how said forceps raising means is manipulated;

a raise mechanism moving member that is mounted in said channeled endoscope cover and with which said raise mechanism embedded in said opening is coupled so as to be freely movable; and a coupling means that couples said driving force generating mechanism with said raise mechanism moving member.

12. An endoscope cover-sheathed endoscope according to claim 11, wherein said forceps raising means also has a capability of said driving force generating mechanism.

13. An endoscope cover-sheathed endoscope according to claim 11, further comprising a partition for isolating said raise mechanism moving member from said driving force generating mechanism so as to tightly shut out water; said coupling means including a water shutout coupling mechanism that couples said driving force generating mechanism with said raise mechanism moving member via said partition so as to tightly shut out water.

14. An endoscope cover-sheathed endoscope according to claim 13, wherein said water shutout coupling mechanism is realized with magnetic forces of magnets.

15. An endoscope cover-sheathed endoscope system an endoscope cover-sheathed endoscope system, comprising:

an endoscope cover-sheathed endoscope made up of an endoscope cover and an endoscope-cover coverable endoscope to be sheathed with said endoscope cover;

an insertion aid including a tube slidably moveable over the surface of an insertional part cover of said endoscope cover and used for assisting in insertion; and an immobilization mechanism formed on an operational endoscope part locking section of said endoscope cover for restricting the movement of said insertion aid as said insertion part and for locking an operational part of said endoscope-cover coverable endoscope.

16. An endoscope cover-sheathed endoscope, comprising:

an endoscope having an elongated insertional part;

an endoscope cover having an endoscope channel into which said insertional part of said endoscope is inserted, and an endoscope locking section for locking the proximal portion of said insertional part; and a locked section formed in the proximal portion of said insertional part and locked in said endoscope locking section when brought into contact with said endoscope locking section;

said locked section having a higher wear resistance than said endoscope locking section.

* * * * *